United States Patent
Chaiworapongsa et al.

(10) Patent No.: US 12,298,315 B2
(45) Date of Patent: *May 13, 2025

(54) SYSTEMS AND METHODS TO IDENTIFY AND TREAT SUBJECTS AT RISK FOR OBSTETRICAL COMPLICATIONS

(71) Applicants: Wayne State University, Detroit, MI (US); The United States of America as Represented by the Secretary, Department of Health and Human Services, Bethesda, MD (US)

(72) Inventors: Tinnakorn Chaiworapongsa, Grosse Pointe Park, MI (US); Roberto Romero, Grosse Pointe, MI (US); Sonia S. Hassan, Novi, MI (US)

(73) Assignees: Wayne State University, Detroit, MI (US); The United States of America as Represented by the Secretary, Dept. of Health and Human Services, Bethesda, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/315,230

(22) Filed: May 10, 2023

(65) Prior Publication Data

US 2023/0341414 A1    Oct. 26, 2023

Related U.S. Application Data

(60) Continuation of application No. 16/387,486, filed on Apr. 17, 2019, now Pat. No. 11,686,735, which is a division of application No. 15/129,771, filed as application No. PCT/US2015/023117 on Mar. 27, 2015, now Pat. No. 10,281,475.

(60) Provisional application No. 61/971,486, filed on Mar. 27, 2014.

(51) Int. Cl.
| | |
|---|---|
| *G01N 33/53* | (2006.01) |
| *A61K 31/22* | (2006.01) |
| *A61K 31/616* | (2006.01) |
| *A61K 31/727* | (2006.01) |
| *C12Q 1/6883* | (2018.01) |
| *G01N 33/68* | (2006.01) |
| *G16H 10/40* | (2018.01) |
| *G16H 20/10* | (2018.01) |
| *G16H 50/30* | (2018.01) |

(52) U.S. Cl.
CPC .......... *G01N 33/689* (2013.01); *A61K 31/22* (2013.01); *A61K 31/616* (2013.01); *A61K 31/727* (2013.01); *C12Q 1/6883* (2013.01); *G01N 33/6872* (2013.01); *G16H 10/40* (2018.01); *G16H 20/10* (2018.01); *G16H 50/30* (2018.01); *C12Q 2600/158* (2013.01); *G01N 2333/475* (2013.01); *G01N 2333/912* (2013.01); *G01N 2800/368* (2013.01); *G01N 2800/50* (2013.01)

(58) Field of Classification Search
None
See application file for complete search history.

(56) References Cited

U.S. PATENT DOCUMENTS

| | | | |
|---|---|---|---|
| 10,281,475 | B2 | 5/2019 | Chaiworapongsa et al. |
| 11,686,735 | B2 * | 6/2023 | Chaiworapongsa ......... G01N 33/689 514/56 |
| 2009/0176247 | A1 | 7/2009 | Bashirians et al. |
| 2010/0304412 | A1 | 12/2010 | Cuckle et al. |
| 2012/0201746 | A1 | 8/2012 | Liu et al. |
| 2017/0242021 | A1 | 8/2017 | Chaiworapongsa et al. |

OTHER PUBLICATIONS

Agarwal, et al., "Preeclampsia and the Anti-Angiogenic State", Pregnancy Hypertens, Jan. 2011, 1 (1), 2011, pp. 17-21.
Ahmed and Cudmore, "Can the biology of VEGF and haem oxygenases help solve pre-eclampsia?" Biochem. Soc. Trans., vol. 37, Part 6, 2009, pp. 1237-1242.
Alahakoon, et al., "Discordant Clinical Presentations of Preeclampsia and Intrauterine Fetal Growth Restriction With Similar Pro and Anti-Angiogenic Profiles," J. Matern. Fetal Neonatal Med., vol. 27, No. 18, 2014, pp. 1854-1859.
Asvold, et al., "Angiogenic Factors in Maternal Circulation and the Risk of Severe Fetal Growth Restriction," Am. J. Epidemiol., vol. 173, No. 6, 2011, pp. 630-639.
Bauer, et al., "Pravastatin Attenuates Hypertension, Oxidative Stress, and Angiogenic Imbalance in Rat Model of Placental Ischemia-Induced Hypertension," Hypertension, vol. 61, No. 5, 2013, pp. 1103-1110.
Bujold, et al., "Evidence Supporting That the Excess of the sVEGFR-1 Concentration in Maternal Plasma in Preeclampsia Has a Uterine Origin," J. Matern. Fetal Neonatal Med., vol. 18, No. 1, 2005, pp. 9-16.
Carver, et al., "Maternal Pravastatin Prevents Altered Fetal Brain Development in a Preeclamptic CD-1 Mouse Model," PLoS One, vol. 9, e100873, 2014, 9 pages.
Carver, et al., "The Effect of Maternal Pravastatin Therapy on Adverse Sensorimotor Outcomes of the Offspring in a Murine Model of Preeclampsia," Int. J. Dev. Neurosci., vol. 33, 2014, pp. 33-40.
Chaiworapongsa, et al. "Unexplained Fetal Death is Associated With Increased Concentrations of Anti-Angiogenic Factors in Amniotic Fluid", J. Matern. Fetal Neonatal Med., vol. 23, No. 8, 2010, pp. 794-805.

(Continued)

*Primary Examiner* — Gary Counts
(74) *Attorney, Agent, or Firm* — Lee & Hayes, P.C.

(57) ABSTRACT

Provided are systems and methods for assessing the presence or risk of obstetrical complications, particularly those related to an angiogenic and anti-angiogenic imbalance. Also provided are methods of treating an angiogenic and anti-angiogenic imbalance with water-soluble statins, such as pravastatin.

14 Claims, 20 Drawing Sheets

Specification includes a Sequence Listing.

(56) References Cited

OTHER PUBLICATIONS

Chaiworapongsa, et al., "A Subset of Patients Destined to Develop Spontaneous Preterm Labor Has an Abnormal Angiogenic/Anti-Angiogenic Profile in Maternal Plasma: Evidence in Support of Pathophysiologic Heterogeneity of Preterm Labor Derived From a Longitudinal Study," J. Matern. Fetal Neonatal Med., vol. 22, No. 12, 2009, pp. 1122-1139.
Chaiworapongsa, et al., "Fetal Death : A Condition With a Dissociation in the Concentrations of Soluble Vascular Endothelial Growth Factor Receptor-2 Between the Maternal and Fetal Compartments", J. Matern. Fetal Neonatal Med., vol. 23, No. 9, 2010, pp. 960-972.
Chaiworapongsa, et al., "Maternal Plasma Concentrations of Angiogenic/Anti-Angiogenic Factors Are of Prognostic Value in Patients Presenting to the Obstetrical Triage Area With the Suspicion of Preeclampsia," J. Maternal-Fetal Neonatal Med., vol. 24, No. 10, 2011, pp. 1187-1207.
Chaiworapongsa, et al., "Maternal Plasma Concentrations of Angiogenic/Antiangiogenic Factors in the Third Trimester of Pregnancy to Identify the Patient at Risk for Stillbirth at or Near Term and Severe Late Preeclampsia", Am. J. Obstet. Gynecol., vol. 208, No. 4, 2013, pp. 287.e1-287.e15.
Chaiworapongsa, et al., "Plasma Soluble Vascular Endothelial Growth Factor Receptor-1 Concentration Is Elevated Prior to the Clinical Diagnosis of Pre-Eclampsia," J. Matern. Fetal Neonatal Med., vol. 17, No. 1, 2005, pp. 3-18.
Chaiworapongsa, et al., "The Maternal Plasma Soluble Vascular Endothelial Growth Factor Receptor-1 Concentration Is Elevated in SGA and the Magnitude of the Increase Relates to Doppler Abnormalities in the Maternal and Fetal Circulation," J. Matern. Fetal Neonatal Med., vol. 21, No. 1, 2008, pp. 25-40.
Clinical Trials, "View of NCT01717586 on Jan. 21, 2014", retrieved on Jun. 11, 2015 at <<https://clinicaltrials.gov/archive/NCT01717586/2014_01_21>>, ClinicalTrials.gov, pp. 1-8 2015.
Costantine, et al., "Pravastatin for the Prevention of Preeclampsia in High-Risk Pregnant Women", Obstet. Gynecol., vol. 121, No. 2 0 1, 2013, pp. 1-7.
Costantine, et al., "Using Pravastatin to Improve the Vascular Reactivity in a Mouse Model of Soluble Fms-Like Tyrosine Kinase-1-Induced Preeclampsia," Obstet. Gynecol., vol. 116, No. 1, 2010, pp. 114-120.
Crispi, et al., "Predictive Value of Angiogenic Factors and Uterine Artery Doppler for Early- Versus Late-Onset Pre-Eclampsia and Intrauterine Growth Restriction," Ultrasound Obstet. Gynecol., vol. 31, 2008, pp. 303-309.
Edison and Muenke, "Mechanistic and Epidemiologic Considerations in the Evaluation of Adverse Birth Outcomes Following Gestational Exposure to Statins," Am. J. Med. Genet. A., vol. 131, No. 3, 2004, pp. 287-298.
Elahi, et al., "Long-Term Statin Administration to Dams on High-Fat Diet Protects Not Only Them but Also Their Offspring From Cardiovascular Risk," Ann. Nutr. Metab., vol. 62, 2013, pp. 250-256.
Elahi, et al., "Statin Treatment in Hypercholesterolemic Pregnant Mice Reduced Cardiovascular Risk Factors in Their Offspring," Hypertension, vol. 51, 2008, pp. 939-944.
Erez, et al., "The Change in Concentrations of Angiogenic and Anti-Angiogenic Factors in Maternal Plasma Between the First and Second Trimesters in Risk Assessment for the Subsequent Development of Preeclampsia and Small-For-Gestational Age," J. Matern. Fetal Neonatal Med., vol. 21, No. 5, 2008, pp. 279-287.
Espinoza, et al., "A Role of the Anti-Angiogenic Factor sVEGFR-1 in the "Mirror Syndrome" (Ballantyne's Syndrome)," J. Matern. Fetal. Neonatal. Med., vol. 19, No. 10, 2006, pp. 607-613.
Espinoza, et al., "Unexplained Fetal Death: Another Anti-Angiogenic State", J. Matern. Fetal Neonatal. Med., vol. 20, No. 7, 2007, pp. 495-507.
Fox, et al., "Effects of Pravastatin on Mediators of Vascular Function in a Mouse Model of Soluble Fms-Like Tyrosine Kinase-1-Induced Preeclampsia," Am. J. Obstet. Gynecol., vol. 205, 2011, pp. 366-367.
Frick, et al., "Statins Differentially Regulate Vascular Endothelial Growth Factor Synthesis in Endothelial and Vascular Smooth Muscle Cells," Atherosclerosis, vol. 170, 2003, pp. 229-236.
Garovic, "The Role of Angiogenic Factors in the Prediction and Diagnosis of Preeclampsia Superimposed on Chronic Hypertension," Hypertension, vol. 59, 2012, pp. 555-557.
Girardi G., "Pravastatin Prevents Miscarriages in Antiphospholipid Antibody-Treated Mice," J. Reprod. Immunol., vol. 82, 2009, pp. 126-131.
Gu, et al., "Placental Productions and Expressions of Soluble Endoglin, Soluble Fms-Like Tyrosine Kinase Receptor-1, and Placental Growth Factor in Normal and Preeclamptic Pregnancies," J. Clin. Endocrinol. Metab., vol. 93, No. 1, 2008, pp. 260-266.
Hagmann, et al., "The Promise of Angiogenic Markers for the Early Diagnosis and Prediction of Preeclampsia," Clinical Chem., vol. 58, No. 5, 2012, pp. 837-845.
International Preliminary Report on Patentability for International Application No. PCT/US2015/023117, mailed on Oct. 6, 2016, 9 pgs.
Kumasawa, et al., "Pravastatin Induces Placental Growth Factor (PGF) and Ameliorates Preeclampsia in a Mouse Model," Proc. Natl. Acad. Sci. U.S.A., vol. 108, No. 4, 2011, pp. 1451-1455.
Kusanovic, et al., "A Prospective Cohort Study of the Value of Maternal Plasma Concentrations of Angiogenic and Anti-Angiogenic Factors in Early Pregnancy and Midtrimester in the Identification of Patients Destined to Develop Preeclampsia," J. Matern. Fetal Neonatal Med., vol. 22, No. 11, 2009, pp. 1021-1038.
Kusters, et al., "Statin Use During Pregnancy: A Systematic Review and Meta-Analysis," Expert Rev. Cardiovasc. Ther., vol. 10, No. 3, 2012, pp. 363-378.
Lam, et al., "Circulating Angiogenic Factors in the Pathogenesis and Prediction of Preeclampsia," Hypertension, vol. 46, 2005, pp. 1077-1085.
Levine, et al., "Circulating Angiogenic Factors and the Risk of Preeclampsia," N. Engl. J. Med., vol. 350, No. 7, 2004, pp. 672-683.
Levine, et al., "Soluble Endoglin and Other Circulating Antiangiogenic Factors in Preeclampsia," N. Engl. J. Med., vol. 355, No. 10, 2006, pp. 992-1005.
Li, et al., "Recombinant Vascular Endothelial Growth Factor 121 Attenuates Hypertension and Improves Kidney Damage in a Rat Model of Preeclampsia," Hypertension, vol. 50, 2007, pp. 686-692.
Llurba, et al., "Angiogenic and Antiangiogenic Factors Before and After Resolution of Maternal Mirror Syndrome," Ultrasound Obstet. Gynecol., vol. 40, 2012, pp. 367-369.
Luttun and Carmeliet, "Soluble VEGF Receptor Flt1: the Elusive Preeclampsia Factor Discovered?" J. Clin. Invest., vol. 111, No. 5, 2003, pp. 600-602.
Maxwell, "The Dose Response Relationship and Clinical Trials", Dose-response relationships in clinical pharmacology, 1989, pp. 131-143.
Maynard and Karumanchi, "Angiogenic Factors and Preeclampsia," Semin. Nephrol., vol. 31, No. 1, 2011, pp. 33-46.
McDonnold, et al., "The Effect of Prenatal Pravastatin Treatment on Altered Fetal Programming of Postnatal Growth and Metabolic Function in a Preeclampsia-Like Murine Model," Am. J. Obstet. Gynecol., vol. 210, 2014, pp. 542.e1-542.e7.
McElrath, et al., "Longitudinal Evaluation of Predictive Value for Preeclampsia of Circulating Angiogenic Factors Through Pregnancy," Am. J. Obstet. Gynecol., vol. 207, 2012, pp. 407.e1-407.e7.
Myatt, et al., "Can Changes in Angiogenic Biomarkers Between the First and Second Trimesters of Pregnancy Predict Development of Pre-Eclampsia in a Low-Risk Nulliparous Patient Population?" BJOG, vol. 120, No. 10, 2013, pp. 1183-1191.
Myers, et al., "Angiogenic Factors Combined With Clinical Risk Factors to Predict Preterm Pre-Eclampsia in Nulliparous Women: A Predictive Test Accuracy Study," BJOG, vol. 120, 2013, pp. 1215-1223.
Office Action for U.S. Appl. No. 16/387,486, mailed on Dec. 23, 2022, Chaiworapongsa, "Systems and Methods to Identify and Treat Subjects at Risk for Obstetrical Complications", 9 Pages 2022.
Office action for U.S. Appl. No. 15/129,771, mailed on Jul. 20, 2018, Chaiworapongsa, "Systems and Methods to Identify and Treat Subjects at Risk for Obstetrical Complications", 15 pages, 2018.

(56) References Cited

OTHER PUBLICATIONS

Office Action for U.S. Appl. No. 16/387,486, mailed on Jul. 6, 2022, Chaiworapongsa, "Systems and Methods to Identify and Treat Subjects at Risk for Obstetrical Complications", 17 Pages 2022.

Powers, et al., "Soluble fms-Like Tyrosine Kinase 1 (sFlt1), Endoglin and Placental Growth Factor (PlGF) in Preeclampsia among High risk Pregnancies", PloS ONE, Oct. 2010, vol. 5, Issue 10, 2010, pp. 1-12.

Ramma and Ahmed, "Therapeutic Potential of Statins and the Induction of Heme Oxygenase-1 in Preeclampsia," J. Reprod. Immunol., vol. 101-102, No. 100, 2014, pp. 153-160.

Rana, et al., "Angiogenic Factors and the Risk of Adverse Outcomes in Women With Suspected Preeclampsia," Circulation, vol. 125, 2012, pp. 911-919.

Rana, et al., "Sequential Changes in Antiangiogenic Factors in Early Pregnancy and Risk of Developing Preeclampsia," Hypertension, vol. 50, 2007, pp. 137-142.

Redecha, et al., "Pravastatin Prevents Miscarriages in Mice: Role of Tissue Factor in Placental and Fetal Injury," Blood, vol. 113, No. 17, 2009, pp. 4101-4109.

Romero, et al., "A Longitudinal Study of Angiogenic (Placental Growth Factor) and Anti-Angiogenic (Soluble Endoglin and Soluble Vascular Endothelial Growth Factor Receptor-1) Factors in Normal Pregnancy and Patients Destined to Develop Preeclampsia and Deliver a Small for Gestational Age Neonate," J. Matern. Fetal Neonatal Med., vol. 21, No. 1, 2008, pp. 9-23.

Romero, et al., "An Imbalance Between Angiogenic and Anti-Angiogenic Factors Precedes Fetal Death in a Subset of Patients: Results of a Longitudinal Study", J. Matern. Fetal Neonatal Med., vol. 23, No. 12, 2010, pp. 1384-1399.

Romero, et al., "Maternal Floor Infarction/Massive Perivillous Fibrin Deposition: A Manifestation of Maternal Antifetal Rejection," Am. J. Reprod. Immunol., vol. 70, No. 4, 2013, pp. 285-298.

Saad, et al., "Effects of Pravastatin on Angiogenic and Placental Hypoxic Imbalance in a Mouse Model of Preeclampsia," Reprod. Sci., vol. 21, No. 1, 2014, pp. 138-145.

Sergio, et al., "Prophylaxis of Recurrent Preeclampsia: Low-Molecular-Weight Heparin Plus Low-Dose Aspirin Versus Low-Dose Aspirin Alone", Hypertens Pregnancy, 2006, vol. 25, No. 2, pp. 115-127.

Simas, et al., "Angiogenic Biomarkers for Prediction of Early Preeclampsia Onset in High-Risk Women," J. Matern. Fetal Neonatal Med., vol. 27, No. 10, 2013, pp. 1038-1048.

Soto, et al., "Late-Onset Preeclampsia is Associated With an Imbalance of Angiogenic and Anti-Angiogenic Factors in Patients With and Without Placental Lesions Consistent With Maternal Underperfusion," J. Matern. Fetal Neonatal Med., vol. 25, No. 5, 2012, pp. 498-507.

PCT Search Report and Written Opinion for International Application No. PCT/US2015/023117, mailed Jul. 10, 2015, 11pgs.

Stepan, et al., "Predictive Value of Maternal Angiogenic Factors in Second Trimester Pregnancies With Abnormal Uterine Perfusion," Hypertension, vol. 49, 2007, pp. 818-824.

Tannetta, et al., "Characterisation of Syncytiotrophoblast Vesicles in Normal Pregnancy and Pre-Eclampsia: Expression of Flt-1 and Endoglin," PLoS One, vol. 8, No. 2, 2013, 13 pages.

Thadhani, et al., "Pilot Study of Extracorporeal Removal of Soluble Fms-Like Tyrosine Kinase 1 in Preeclampsia," Circulation, vol. 124, 2011, pp. 940-950.

Therapeutics Initiative Evidence Based Drug Therapy, Statins benefit for secondary prevention confirmed, Therapeutics letter, Jul.-Sep. 2003, 2 pgs.

Torzewski, et al, "Animal Models of C-Reactive Protein", Hindawl Publishing Corporation, Mediators of Inflammation, vol. 2014, Article ID 683598, 2014, pp. 1-7.

Van Der Vekens, et.al, "Human and Equine Cardiovascular Endocrinology: Beware to Compare", Cardiovascular Endocrinology, vol. 2, No. 4, 2013, pp. 67-76.

Verlohren, et al., "Angiogenic Growth Factors in the Diagnosis and Prediction of Pre-Eclampsia," Clinical Science, vol. 122, 2012, pp. 43-52.

Whitten, et al., "Evidence of an Imbalance of Angiogenic/Antiangiogenic Factors in Massive Perivillous Fibrin Deposition (Maternal Floor Infarction): A Placental Lesion Associated With Recurrent Miscarriage and Fetal Death," Am. J. Obstet. Gynecol., vol. 208, No. 4, 2013, 22 pages.

Wong, et al., "A Deficiency in Haem Oxygenase-1 Induces Foetal Growth Restriction by Placental Vasculature Defects," Acta Paediatr., vol. 101, 2012, pp. 827-834.

Zhao, et al., "Maternal Heme Oxygenase 1 Regulates Placental Vasculature Development Via Angiogenic Factors in Mice," Biol. Reprod., vol. 85, No. 5, 2011, pp. 1005-1012.

\* cited by examiner sEng (SEQ ID NO:1)
MDRGTLPLAVALLLASCSLSPTSLAETVHCDLQPVGPERGEVTYTTSQVSKGCV
AQAPNAILEVHVLFLEFPTGPSQLELTLQASKQNGTWPREVLLVLSVNSSVFLHL
QALGIPLHLAYNSSLVTFQEPPGVNTTELPSFPKTQILEWAAERGPITSAAELNDP
QSILLRLGQAQGSLSFCMLEASQDMGRTLEWRPRTPALVRGCHLEGVAGHKEA
HILRVLPGHSAGPRTVTVKVELSCAPGDLDAVLILQGPPYVSWLIDANHNMQIWT
TGEYSFKIFPEKNIRGFKLPDTPQGLLGEARMLNASIVASFVELPLASIVSLHASS
CGGRLQTSPAPIQTTPPKDTCSPELLMSLIQTKCADDAMTLVLKKELVAHLKCTIT
GLTFWDPSCEAEDRGDKFVLRSAYSSCGMQVSASMISNEAVVNILSSSSPQR

PIGF (SEQ ID NO:2)
MPVMRLFPCFLQLLAGLALPAVPPQQWALSAGNGSSEVEVVPFQEVWGRSYC
RALERLVDVVSEYPSEVEHMFSPSCVSLLRCTGCCGDENLHCVPVETANVTMQ
LLKIRSGDRPSYVELTFSQHVRCECRPLREKMKPERRRPKGRGKRRREKQRPT
DCHLCGDAVPRR sVEGFR-1 (SEQ ID NO:3)
MVSYWDTGVLLCALLSCLLLTGSSSGSKLKDPELSLKGTQHIMQAGQTLHLQCR
GEAAHKWSLPEMVSKESERLSITKSACGRNGKQFCSTLTLNTAQANHTGFYSC
KYLAVPTSKKKETESAIYIFISDTGRPFVEMYSEIPEIIHMTEGRELVIPCRVTSPNI
TVTLKKFPLDTLIPDGKRIIWDSRKGFIISNATYKEIGLLTCEATVNGHLYKTNYLTH
RQTNTIIDVQISTPRPVKLLRGHTLVLNCTATTPLNTRVQMTWSYPDEKNKRASV
RRRIDQSNSHANIFYSVLTIDKMQNKDKGLYTCRVRSGPSFKSVNTSVHIYDKAFI
TVKHRKQQVLETVAGKRSYRLSMKVKAFPSPEVVWLKDGLPATEKSARYLTRGY
SLIIKDVTEEDAGNYTILLSIKQSNVFKNLTATLIVNVKPQIYEKAVSSFPDPALYPL
GSRQILTCTAYGIPQPTIKWFWHPCNHNHSEARCDFCSNNEESFILDADSNMGN
RIESITQRMAIIEGKNKMASTLVVADSRISGIYICIASNKVGTVGRNISFYITDVPNG
FHVNLEKMPTEGEDLKLSCTVNKFLYRDVTWILLRTVNNRTMHYSISKQKMAITK
EHSITLNLTIMNVSLQDSGTYACRARNVYTGEEILQKKEITIRGEHCNKKAVFSRIS
KFKSTRNDCTTQSNVKH

FIG. 14

SEQUENCE LISTING

```
Sequence total quantity: 3
SEQ ID NO: 1               moltype = AA  length = 437
FEATURE                    Location/Qualifiers
source                     1..437
                           mol_type = protein
                           organism = Homo sapiens
SEQUENCE: 1
MDRGTLPLAV ALLLASCSLS PTSLAETVHC DLQPVGPERG EVTYTTSQVS KGCVAQAPNA  60
ILEVHVLFLE FPTGPSQLEL TLQASKQNGT WPREVLLVLS VNSSVFLHLQ ALGIPLHLAY  120
NSSLVTFQEP PGVNTTELPS FPKTQILEWA AERGPITSAA ELNDPQSILL RLGQAQGSLS  180
FCMLEASQDM GRTLEWRPRT PALVRGCHLE GVAGHKEAHI LRVLPGHSAG PRTVTVKVEL  240
SCAPGDLDAV LILQGPPYVS WLIDANHNMQ IWTTGEYSFK IFPEKNIRGF KLPDTPQGLL  300
GEARMLNASI VASFVELPLA SIVSLHASSC GGRLQTSPAP IQTTPPKDTC SPELLMSLIQ  360
TKCADDAMTL VLKKELVAHL KCTITGLTFW DPSCEAEDRG DKFVLRSAYS SCGMQVSASM  420
ISNEAVVNIL SSSSPQR                                                437

SEQ ID NO: 2               moltype = AA  length = 170
FEATURE                    Location/Qualifiers
source                     1..170
                           mol_type = protein
                           organism = Homo sapiens
SEQUENCE: 2
MPVMRLFPCF LQLLAGLALP AVPPQQWALS AGNGSSEVEV VPFQEVWGRS YCRALERLVD  60
VVSEYPSEVE HMFSPSCVSL LRCTGCCGDE NLHCVPVETA NVTMQLLKIR SGDRPSYVEL  120
```

```
TFSQHVRCEC RPLREKMKPE RRRPKGRGKR RREKQRPTDC HLCGDAVPRR            170

SEQ ID NO: 3            moltype = AA  length = 687
FEATURE                 Location/Qualifiers
source                  1..687
                        mol_type = protein
                        organism = Homo sapiens
SEQUENCE: 3
MVSYWDTGVL LCALLSCLLL TGSSSGSKLK DPELSLKGTQ HIMQAGQTLH LQCRGEAAHK  60
WSLPEMVSKE SERLSITKSA CGRNGKQFCS TLTLNTAQAN HTGFYSCKYL AVPTSKKKET 120
ESAIYIFISD TGRPFVEMYS EIPEIIHMTE GRELVIPCRV TSPNITVTLK KFPLDTLIPD 180
GKRIIWDSRK GFIISNATYK EIGLLTCEAT VNGHLYKTNY LTHRQTNTII DVQISTPRPV 240
KLLRGHTLVL NCTATTPLNT RVQMTWSYPD EKNKRASVRR RIDQSNSHAN IFYSVLTIDK 300
MQNKDKGLYT CRVRSGPSFK SVNTSVHIYD KAFITVKHRK QQVLETVAGK RSYRLSMKVK 360
APPSPEVVWL KDGLPATEKS ARYLTRGYSL IIKDVTEEDA GNYTILLSIK QSNVFKNLTA 420
TLIVNVKPQI YEKAVSSFPD PALYPLGSRQ ILTCTAYGIP QPTIKWFWHP CNHNHSEARC 480
DFCSNNEESF ILDADSNMGN RIESITQRMA IIEGKNKMAS TLVVADSRIS GIYICIASNK 540
VGTVGRNISF YITDVPNGFH VNLEKMPTEG EDLKLSCTVN KFLYRDVTWI LLRTVNNRTM 600
HYSISKQKMA ITKEHSITLN LTIMNVSLQD SGTYACRARN VYTGEEILQK KEITIRGEHC 660
NKKAVFSRIS KFKSTRNDCT TQSNVKH                                    687
```

SYSTEMS AND METHODS TO IDENTIFY AND TREAT SUBJECTS AT RISK FOR OBSTETRICAL COMPLICATIONS

CROSS REFERENCE TO RELATED APPLICATION

This is a continuation of U.S. patent application Ser. No. 16/387,486, filed Apr. 17, 2019, now issued U.S. Pat. No. 11,686,735 on Jun. 27, 2023; which is a division of U.S. patent application Ser. No. 15/129,771, filed Sep. 27, 2016, now U.S. Pat. No. 10,281,475 issued on May 7, 2019, which is the U.S. National Phase of International Patent Application No. PCT/US2015/23117 filed on Mar. 27, 2015; which International Patent Application claims the benefit of U.S. Provisional Patent Application No. 61/971,486 filed on Mar. 27, 2014. Each of these prior applications is incorporated by reference herein in its entirety.

STATEMENT OF GOVERNMENT INTEREST

This invention was made with government support under N01 HD023342 awarded by the National Institutes of Health. The government has certain rights in the invention.

FIELD OF THE DISCLOSURE

The present disclosure relates to systems and methods to identify subjects having, or at risk of developing, obstetrical complications associated with angiogenic and anti-angiogenic balance. Methods of treating such obstetrical complications using water-soluble statins are also described.

REFERENCE TO SEQUENCE LISTING

The protein sequences described herein are shown using standard letter abbreviations for amino acids, as defined in 37 C.F.R. § 1.822. A computer readable XML file, entitled "W063-0024USC2_SeqList.XML" created on or about May 8, 2023, with a file size of ~5 KB, contains the Sequence Listing for this application and is hereby incorporated by reference in its entirety.

BACKGROUND OF THE DISCLOSURE

During pregnancy, both vasculogenesis and extensive angiogenesis are required for successful fetal and placental development. Vasculogenesis is a process in which endothelial cells differentiate and proliferate within a previously avascular tissue, while angiogenesis refers to the remodeling process that occurs after the initial vascular network is developed. A successful pregnancy requires an appropriate balance between angiogenic and anti-angiogenic processes, and several angiogenic and anti-angiogenic factors are important for successful reproductive function.

An imbalance in angiogenic and anti-angiogenic factors has been observed in several obstetrical complications including miscarriage, implantation failure, early preeclampsia (PE), a subset of late PE, small for gestational age (SGA) neonates, preterm labor, fetal death (FD), placenta-related causes of FD, fetal growth restriction, placental abruption, mirror syndrome (i.e. Ballantyne's syndrome), molar pregnancy, twin-to-twin transfusion syndrome, and placental findings suggestive of maternal floor infarction.

Several large epidemiological studies have found placental lesions in the majority of pregnancies resulting in FD, particularly lesions that are consistent with maternal vascular underperfusion. FD has also been associated with abnormal uterine artery Doppler velocimetry (UtADV) findings and abnormal concentrations of biochemical markers associated with placental function, each measured during the first two trimesters. There is currently no effective way to identify women at increased risk of FD.

SUMMARY OF THE DISCLOSURE

There is a need in the art for systems and methods to identify and treat subjects at risk for obstetrical complications. More particularly, there is a need in the art for systems and methods that assess the presence or risk of developing obstetrical complications, particularly those associated with angiogenic and anti-angiogenic balance, e.g. an imbalance of angiogenic and anti-angiogenic factors. The present disclosure provides systems and methods of assessing the presence or risk of obstetrical complications using concentrations of angiogenic factors and anti-angiogenic factors. In some embodiments, the obstetrical complications are associated with an angiogenic and anti-angiogenic imbalance. The present disclosure also includes methods of treating an angiogenic and anti-angiogenic imbalance and/or obstetrical complications associated with an angiogenic and anti-angiogenic imbalance using water-soluble statins, such as pravastatin.

BRIEF DESCRIPTION OF THE FIGURES

FIG. 6A shows the ROC curves for MoM plasma concentrations of each angiogenic and anti-angiogenic factor as well as the two ratios for the identification of women destined to have a $FD^{up}$. The ROC curves for the two biochemical marker ratios (PlGF/sVEGFR-1 and PlGF/ sEng) are shown contrasted against the ROC for a combination of selected clinical factors (age, smoking, nulliparity, body mass index) and, separately, against uterine artery (UtA) and umbilical artery (UA) Doppler velocimetry pulsatility index (PI) MoM in FIG. 6B and FIG. 6C, respectively.

Figure 7:
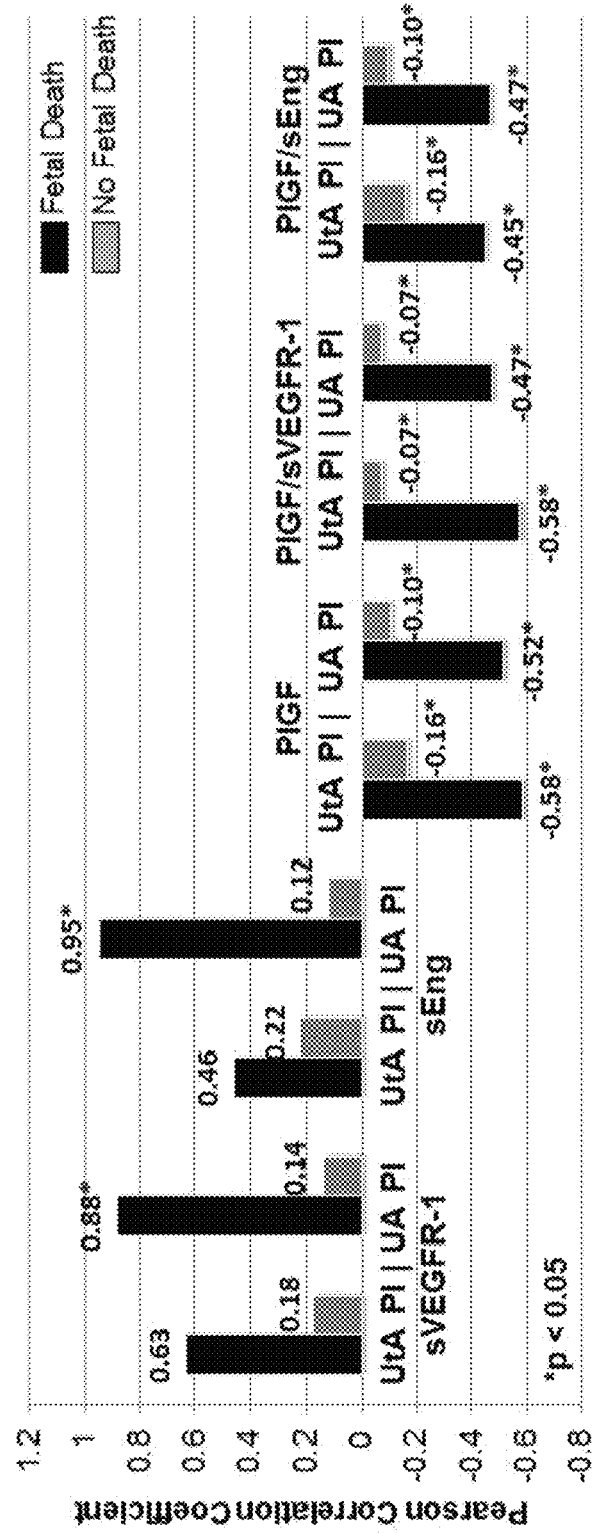
Figure 8A:
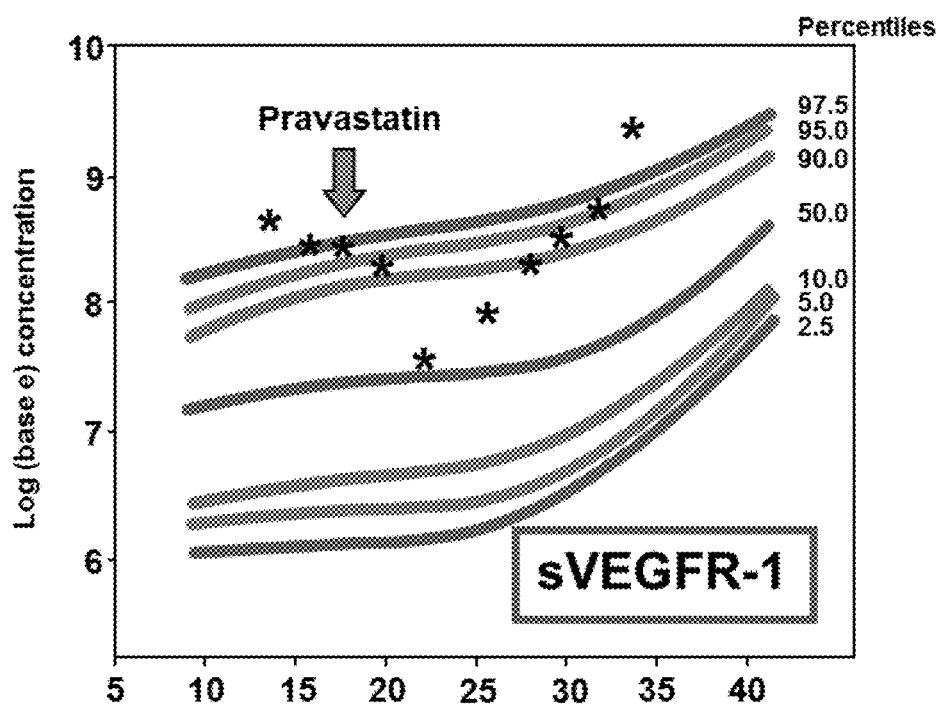
Figure 8B:
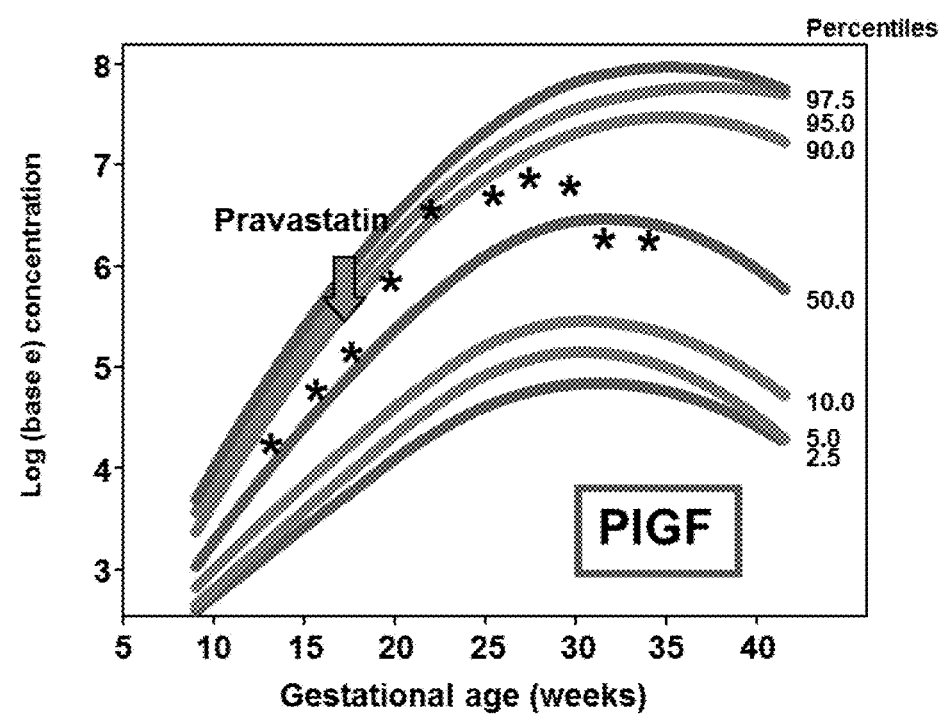
Figure 8C:
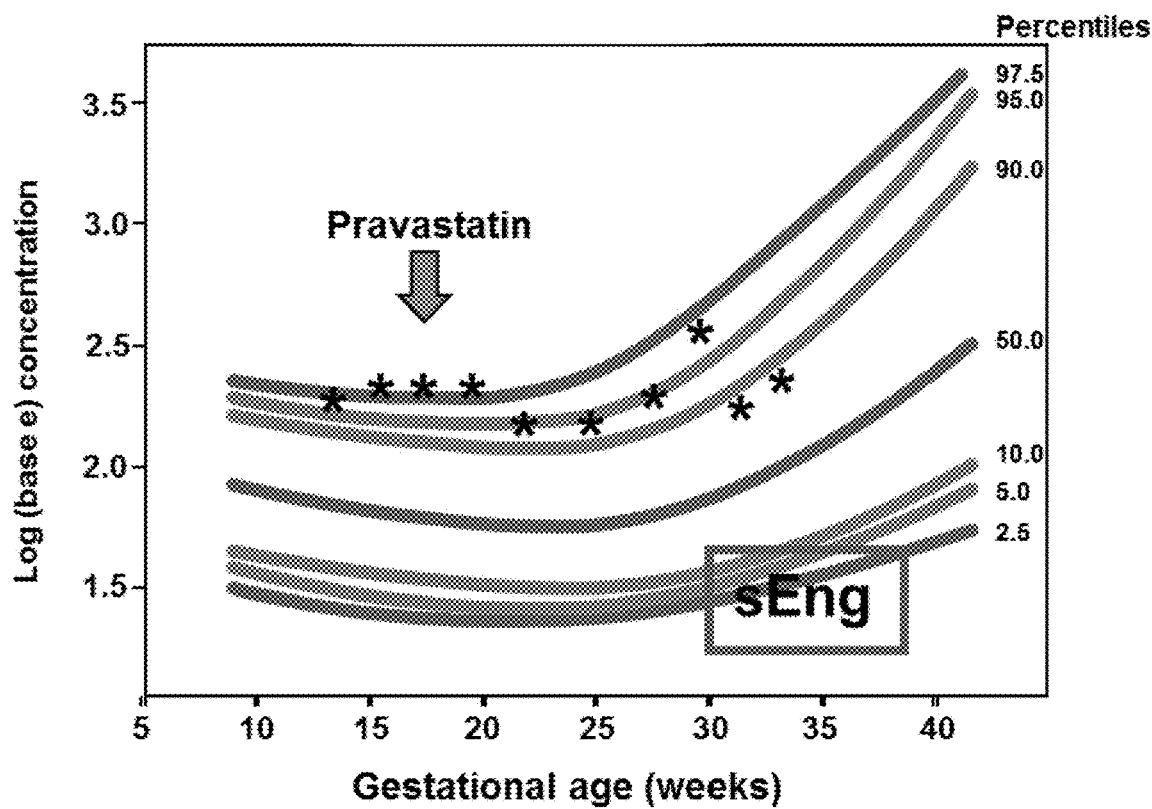
Figure 8D:
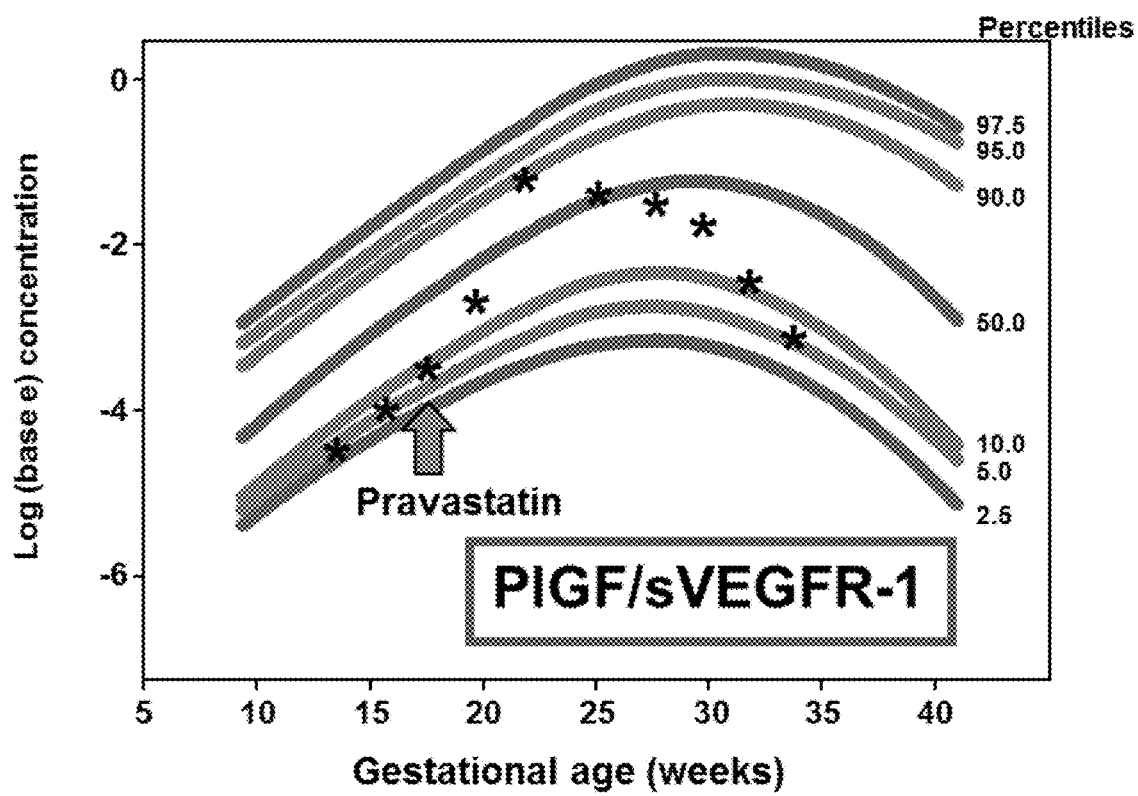

FIG. 7 shows Pearson correlation coefficients among MoM of the plasma concentrations of angiogenic and anti-angiogenic factors and UtA PI as well as UA PI MoMs separately for subjects who did (black) and did not (gray) subsequently have a $FD^{up}$. Eight women who subsequently had a $FD^{up}$ were examined by Doppler velocimetry at 24-<28 weeks of gestation, 821 who did not subsequently have $FD^{up}$ had UtA PI measured, and 830 had UA PI measured during this interval.

FIGS. 8A-8D show maternal plasma concentrations (log base e) of soluble vascular endothelial growth factor receptor-1 (sVEGFR-1) (FIG. 8A), placental growth factor (PlGF) (FIG. 8B), soluble endoglin (sEng) (FIG. 8C) and the ratio of PlGF/sVEGFR-1 (FIG. 8D) throughout pregnancy plotted against reference ranges at $2.5^{th}$ $5^{th}$, $10^{th}$, $50^{th}$, $90^{th}$, $95^{th}$, and $97.5^{th}$ percentile of uncomplicated pregnancies.

Figure 9A:
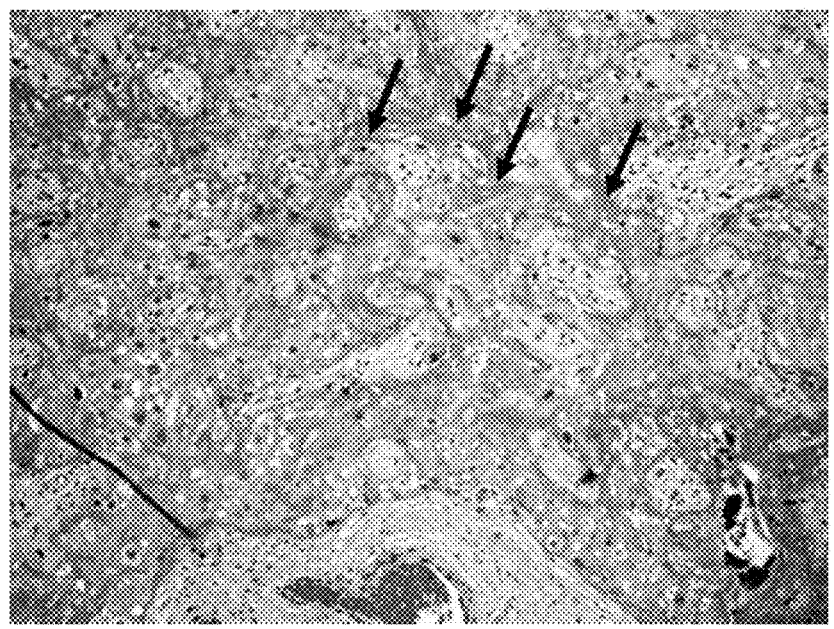
Figure 9B:
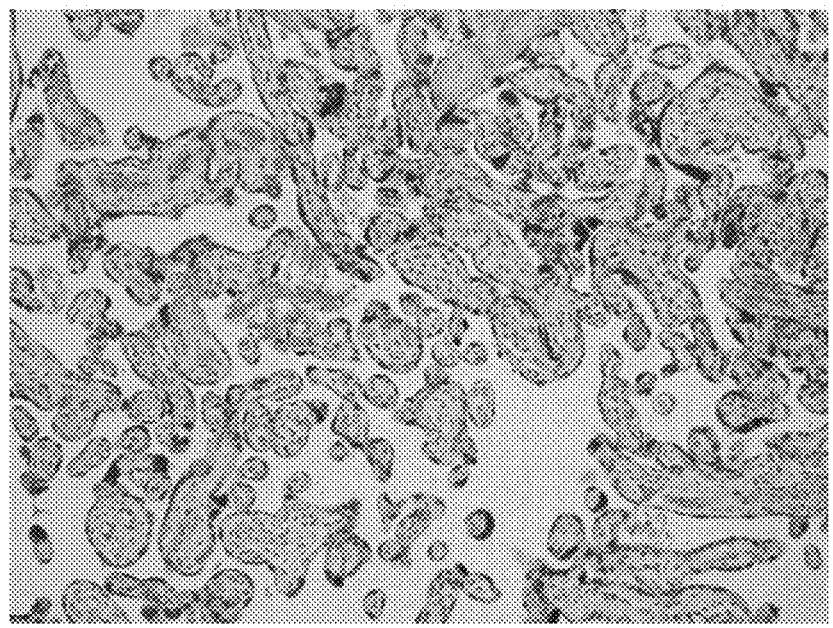
Figure 9C:
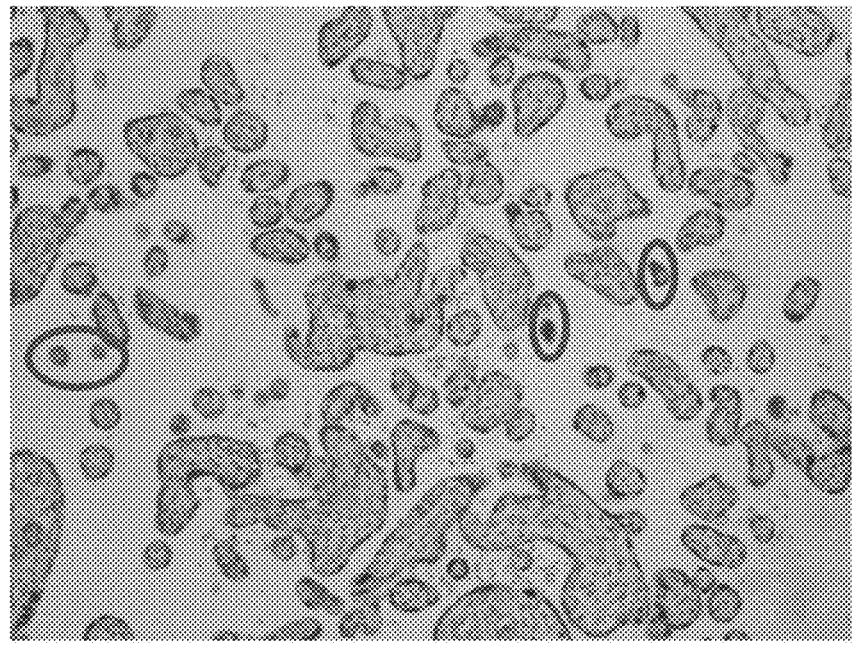
Figure 9D:
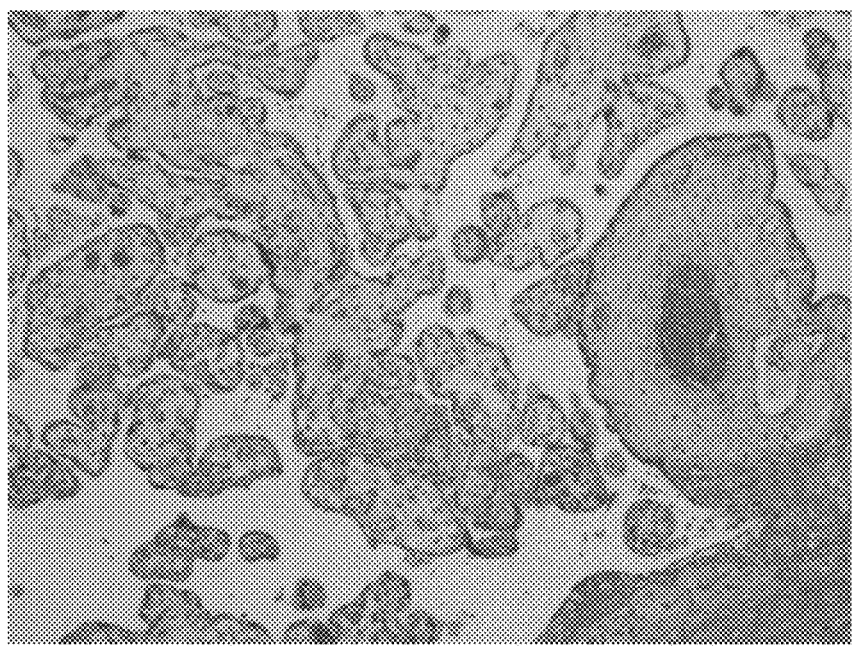

FIGS. 9A-9D show histopathological examination of the placenta from the current pregnancy reveals fibrinoid deposition (arrow) in the intervillous space, involving 20% of the villi (FIG. 9A) and areas with normal intervillous space (3B) (H&E×100). Small and poorly developed villi (circle; FIG. 9C) or distal villous hypoplasia (H&E, ×100) are shown in FIG. 9B. FIG. 9D shows well developed villi at 34 weeks of gestation (H&E, ×100).

Figure 10A:
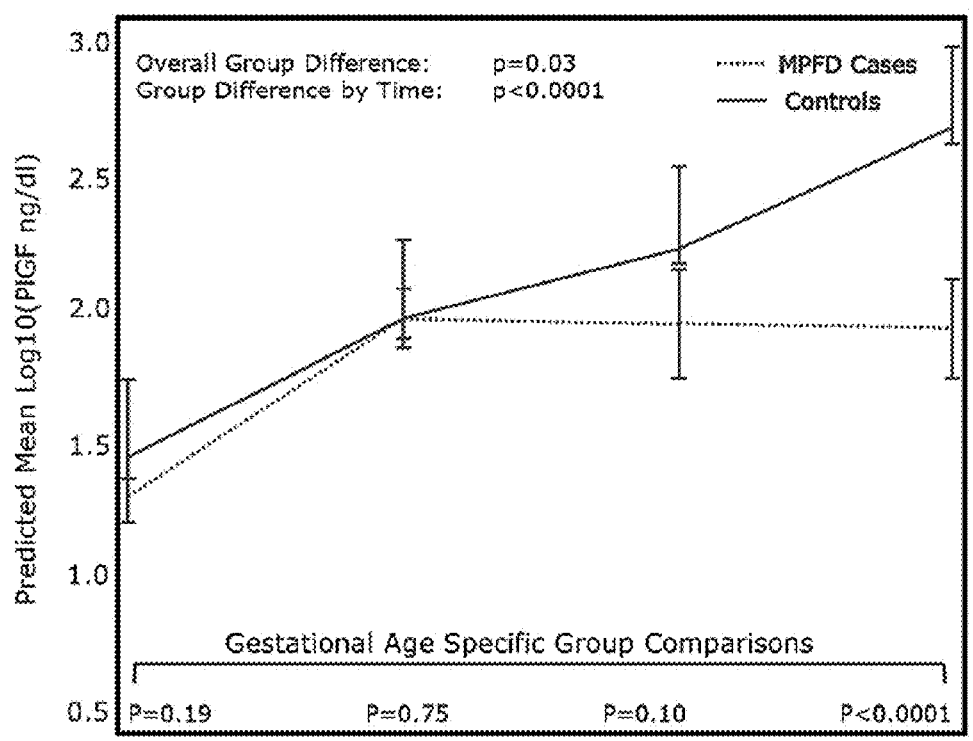
Figure 10B:
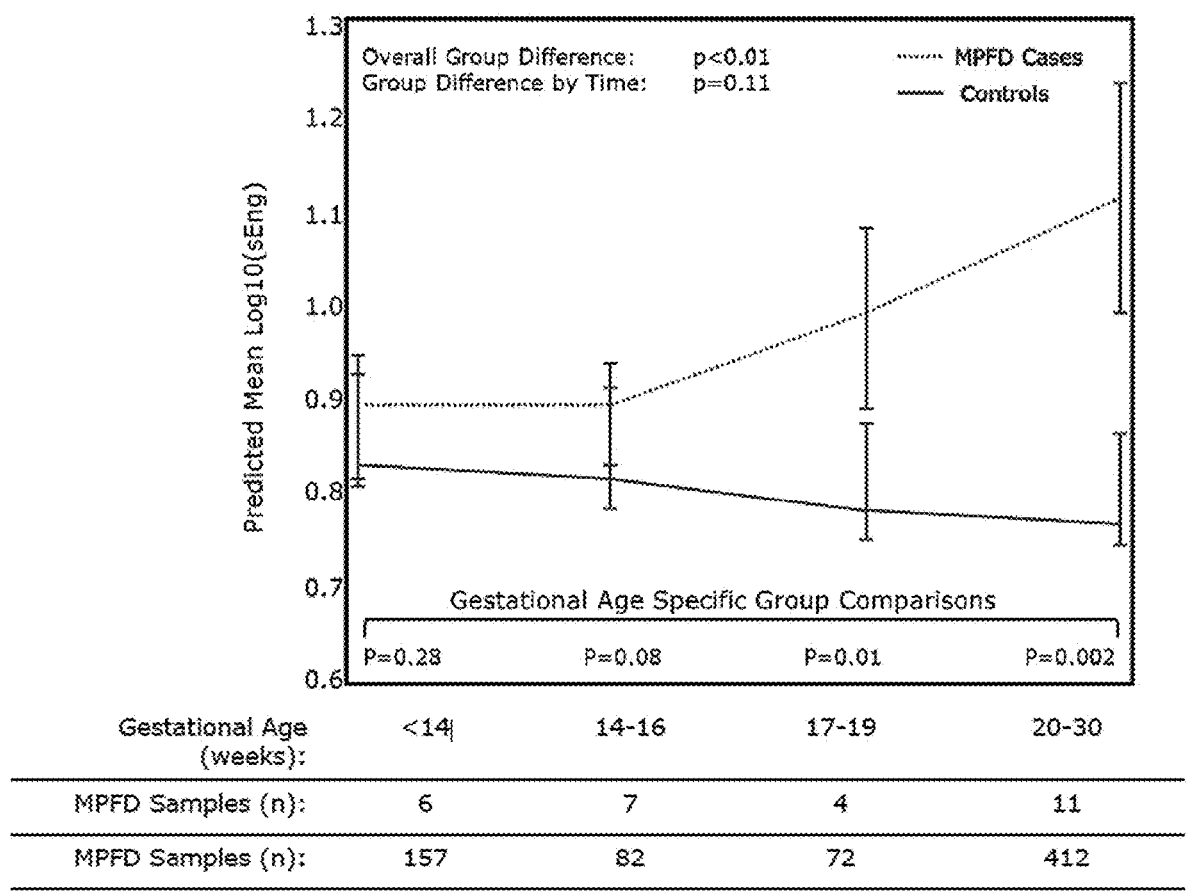

FIG. 10A and FIG. 10B show an estimated mean+/−standard error of plasma concentrations (log 10) of PlGF (FIG. 10A) and sEng (FIG. 10B) in Massive perivillous fibrin deposition of the placenta (MPFD) and uncomplicated pregnancies by gestational age (GA) interval. Estimated mean PlGF concentrations over time are adjusted by GA at venipuncture and body mass index; Estimated mean sEng concentrations over time are adjusted by GA at venipuncture, African American ethnicity and nulliparity; P-values reflect the group differences in estimated mean concentrations overall, as a function of GA interval, and at each GA interval determined by the linear mixed effects model.

Figure 11:
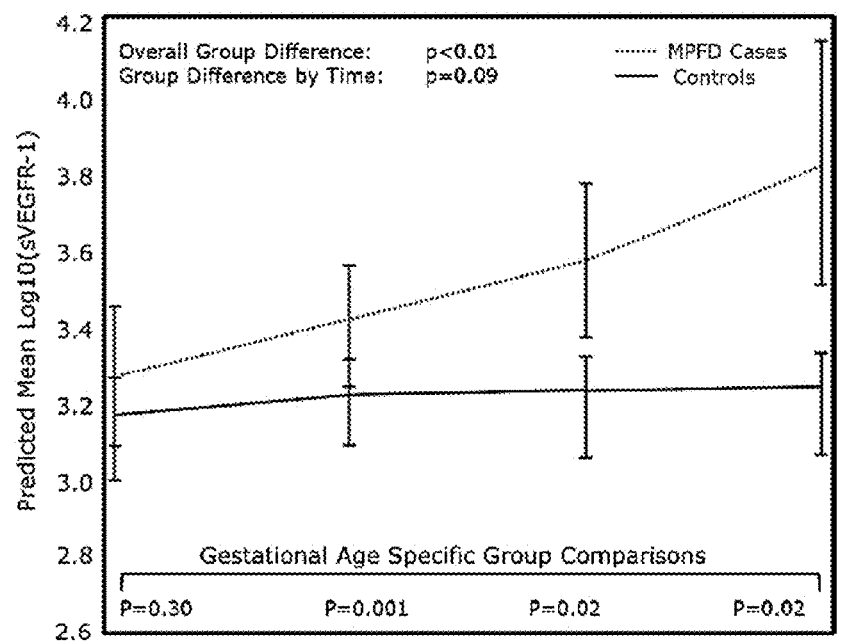

FIG. 11 shows an estimated mean+/−standard error of plasma concentrations (log 10) of sVEGFR-1 in MPFD and uncomplicated pregnancies by GA interval. Estimated mean sVEGFR-1 concentrations over time are adjusted by GA at venipuncture and maternal age; P-values reflect the group differences in estimated mean concentrations overall, as a function of GA interval, and at each GA interval determined by the linear mixed effects model.

Figure 12:
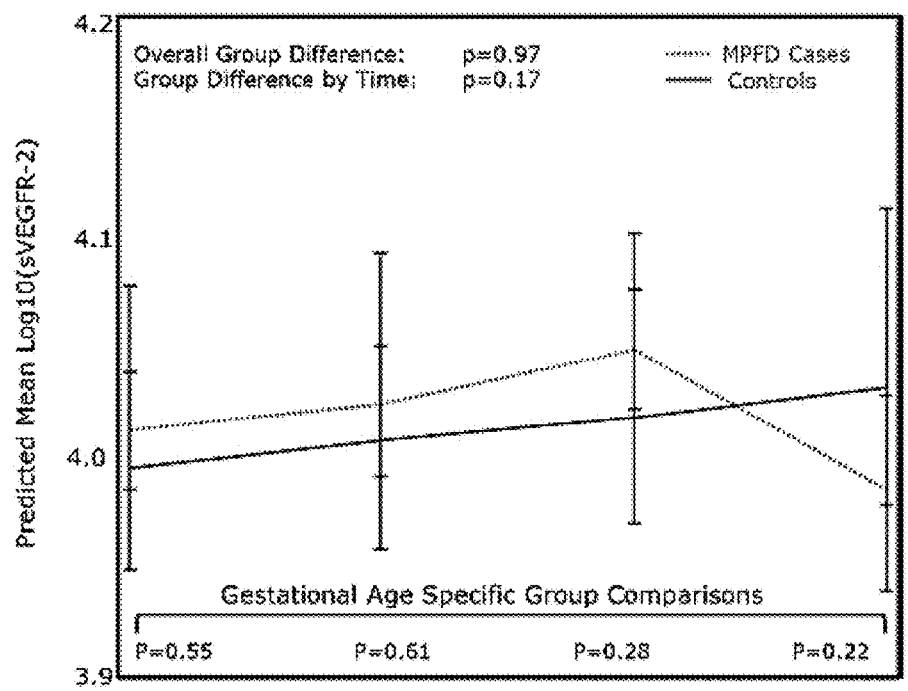

FIG. 12 shows an estimated mean+/−standard error of plasma concentrations (log 10) of sVEGFR-2 in MPFD and uncomplicated pregnancies by GA interval. Estimated mean sVEGFR-2 concentrations over time are adjusted for effects of GA at venipuncture, body mass index, and African American ethnicity; P-values reflect the group differences in estimated mean concentrations overall, as a function of G interval, and at each GA interval determined by the linear mixed effects model.

Figure 13A:
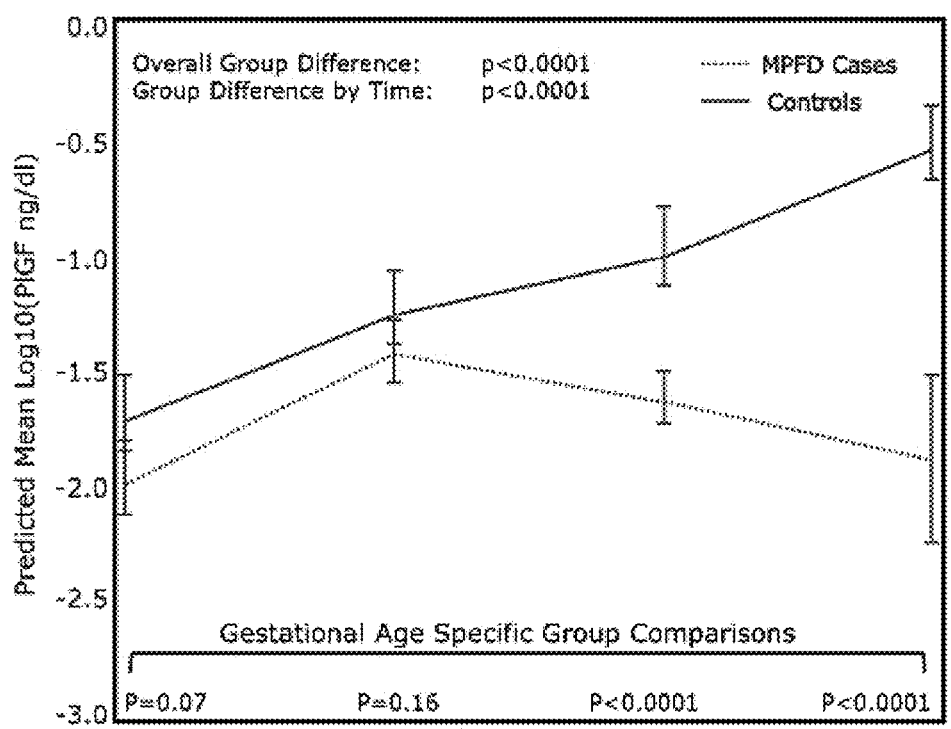
Figure 13B:
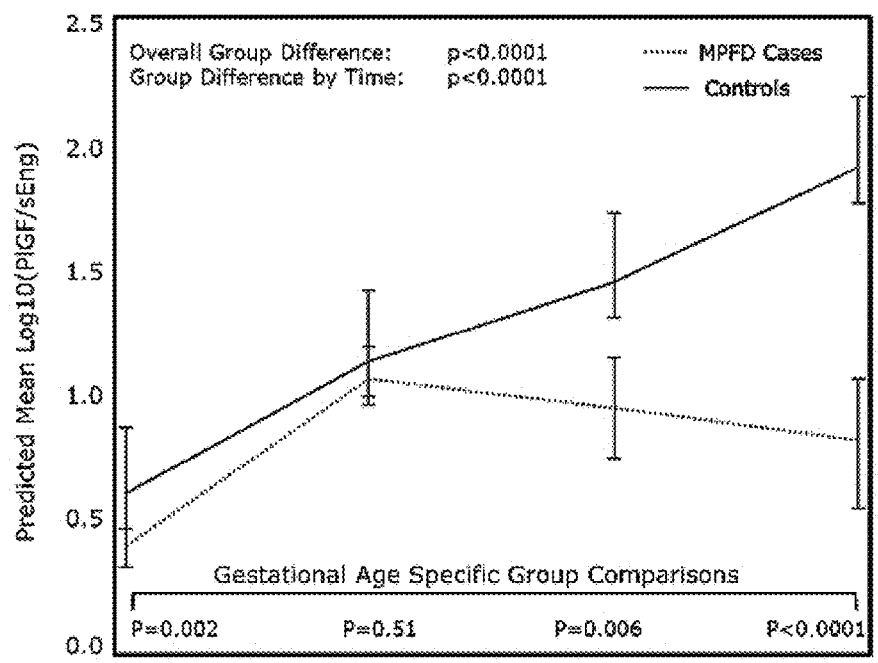

FIG. 13A and FIG. 13B show an estimated mean+/−standard error of plasma concentrations (log 10) in the Ratios of PlGF/sVEGFR-1 (FIG. 13A) and PLGF/sEng (FIG. 13B) in MPFD and uncomplicated pregnancies by GA interval. Estimated mean PlGF/sVEGFR-1 concentration ratios over time are adjusted for GA at venipuncture, body mass index, and nulliparity; Estimated mean PlGF/sVEGFR-1 concentration ratios over time are adjusted for GA at venipuncture, African American ethnicity, and body mass index; P-values reflect the difference in estimated mean concentrations at each GA interval determined by the linear mixed effects model.

FIG. 14 shows exemplary sequences for PlGF (SEQ ID NO: 2), sVEGFR-1 (SEQ ID NO: 3), and sEng (SEQ ID NO: 1).

DETAILED DESCRIPTION

An imbalance of angiogenic/anti-angiogenic factors has been implicated in the pathophysiology of some obstetrical complications, including preeclampsia (PE), pregnancies with small for gestational age (SGA) neonates, stillbirth, preterm labor, and placental lesions. Changes in the concentrations of the angiogenic factor placental growth factor (PlGF), and anti-angiogenic factors, including soluble vascular endothelial growth factor receptor (sVEGFR)-1 (i.e. soluble fms-like tyrosine kinase-1 (sflt-1)) and soluble endoglin (sEng), in maternal circulation, precede the clinical diagnosis of obstetrical complications. Most studies examining the value of these biomarkers, however, have focused on the prediction of PE and only on screening in the first or second trimesters. The results of such studies largely suggest that an imbalance between angiogenic and anti-angiogenic factors increases the likelihood of early PE at a higher magnitude than that in late PE, yet, not all studies have arrived at the same conclusion. Thus far, no cohort studies have evaluated the diagnostic performance of these biomarkers in the third trimester for identifying subjects at risk for stillbirth at or near term, or late PE.

Recently, a new approach for screening of adverse pregnancy outcomes has been proposed to focus on the prevention of pregnancy complications at term. Such an approach would identify the more prevalent disease (e.g. late PE) and predictive models could be applied to low-income settings, where the majority of maternal and perinatal death occurs.

The rationale for assaying biomarkers in the third trimester, in addition to the first or second trimesters, includes: 1) testing performed closer to the event of interest or diagnosis usually yields better results than those performed earlier in gestation. Several studies on screening tests in the first or second trimester for conditions related to placental dysfunction (e.g., PE, SGA, or fetal death (FD)) using either biochemical markers or uterine artery Doppler velocimetry (UtADV) indicate that both are strongly associated with complications which develop earlier in pregnancy and therefore, temporally close to the assessment of biomarkers. The findings disclosed herein that plasma concentrations of the ratio between angiogenic/anti-angiogenic factors outperformed those obtained in the first two trimesters for the identification of subjects with late PE strongly support this view; 2) the risk for a prospective stillbirth increases after 34 weeks of gestation and, similarly, the prevalence of late PE is much higher than that of early-onset disease; and 3) the strategy of testing at the beginning of the third trimester to assess the risk of disease or pregnancy complications could be considered for subjects who did not receive earlier prenatal care or undergo testing.

A previous disadvantage of performing a screening test in the third trimester was that it could be too late to implement therapeutic interventions that could reverse the pathophysiological process responsible for the disease. Although it has been suggested that the administration of aspirin before 16 weeks of gestation may prevent PE, this strategy is not effective to prevent late PE. Thus, a method to identify the subject at risk for late PE is needed, given that late PE accounts for the majority of severe maternal morbidity including eclampsia, especially in developing countries. Furthermore, studies which examined the diagnostic performance of biomarkers in the third trimester in a low-risk population are consistent with the recently proposed new approach for screening of adverse pregnancy outcomes that focuses on the prevention of pregnancy complications at term in low-risk, unselected populations. As described herein, once a subject has been identified as being at risk for pregnancy complications, water-soluble statins can be administered.

The first trimester of pregnancy refers to the 1st week to the 12th week of pregnancy. The second trimester of pregnancy refers to the 13th week to the 27th week of pregnancy. The third trimester of pregnancy refers to the 28th week of pregnancy until birth, which is the 40th week for a full-term pregnancy.

Obstetrical complications are diseases or conditions that arise during the course of pregnancy, childbirth, or the postnatal period. Obstetrical complications associated with an imbalance of angiogenic factors and anti-angiogenic factors include miscarriage, implantation failure, early PE, a subset of late PE, SGA neonates, preterm labor, FD, placenta-related causes of FD, fetal growth restriction, maternal vascular underperfusion, placental lesions, placental abruption, mirror syndrome, molar pregnancy, twin-to-twin transfusion syndrome, and placental findings suggestive of maternal floor infarction (MFI). Obstetrical complications can arise with fetal congenital abnormalities or without fetal congenital abnormalities.

Preeclampsia (PE) is a syndrome defined by pregnancy-induced hypertension and proteinuria, which can lead to eclampsia (convulsions), and other serious maternal and/or fetal complications. PE originating in early gestation is closely related to complications of pregnancy such as implantation failure, and threatened and spontaneous miscarriage. PE has a complex pathophysiology involving abnormal physiologic transformation of the spiral arteries, intravascular inflammation, endothelial cell dysfunction, excessive generation of thrombin, oxidative stress, and an angiogenic and anti-angiogenic imbalance. PE affects 2-8% of all pregnancies and is a major cause of maternal and perinatal mortality. Furthermore, women with PE have an 8-fold higher risk of cardiovascular death later in their life, and offspring born from pregnancies affected by PE have an increased risk of metabolic and cardiovascular disease, and mortality later in life.

The present diagnostic criteria for PE set by the United States National High Blood Pressure Education Program Working Group on High Blood Pressure in Pregnancy include new-onset hypertension coupled with proteinuria that develops after 20 weeks of gestation in women with previously normal blood pressures. These criteria further define PE as systolic or diastolic blood pressures of ≥140 and/or ≥90 mmHg, respectively, measured at two or more different time points, at least four hours but not more than one week apart, as well as proteinuria of ≥300 mg protein in a 24 hour urine sample, or two random urine specimens obtained at least four hours but not more than one week apart containing ≥1+ protein on a dipstick. PE is also associated with other signs and symptoms including edema, visual disturbances, headache, and epigastric pain. Laboratory abnormalities may include metholysis, elevated liver enzymes, and low platelet counts (HELLP syndrome).

Based on the timing of the clinical manifestation, PE has been historically classified into different sub-forms, such as "term" (≥37 weeks) and "preterm" (<37 weeks). PE may also be classified as "early" or "late" according to gestational age (GA) at diagnosis or delivery. Different studies have employed a range of GA cutoffs varying between 28 and 35 weeks for the distinction between early-onset and late PE, but the GA cut-off most frequently used is 34 weeks. Early PE is associated with multisystemic involvement, a higher frequency of SGA neonates, and placental vascular lesions of underperfusion. Because early PE is a frequent indication for preterm delivery, the condition is also associated with a higher rate of neonatal morbidity. In contrast, late PE is associated with better neonatal outcomes than early PE. Although much emphasis has been focused on early PE, most (75%) cases of PE are late PE. Consequently, late PE accounts for a substantial proportion of medically indicated preterm (34-36 weeks) births and severe maternal morbidity, including most cases of eclampsia, the form of the disease that accounts for most maternal deaths. Hence, identifying predictors of late PE is a health care priority. It is important to note that PE may occur intrapartum or postpartum; thus, monitoring and evaluating the symptoms of PE should be continued during the postpartum period.

The American College of Obstetricians and Gynecologists (ACOG) criteria for severe PE include the presence of one or more of: blood pressure of 160 mm Hg systolic or higher, or 110 mm Hg diastolic or higher on two occasions at least six hours apart while the subject is on bed rest; proteinuria of 5 g or higher in a 24-hour urine specimen, or 3+ or greater on two random urine samples collected at least four hours apart; oliguria of less than 500 mL in 24 hours; cerebral or visual disturbances; pulmonary edema or cyanosis; epigastric or right upper-quadrant pain; impaired liver function; thrombocytopenia; and fetal growth restriction. Severe late PE is severe PE, as defined by the ACOG, that occurs at 34 weeks or later in gestation, or at delivery.

Fetal death (FD; e.g. stillbirth), another obstetrical syndrome, affects three million pregnancies worldwide each year. These deaths are usually classified into early (20-28 weeks) and late (≥29 weeks) subtypes to distinguish those that might have been prevented by iatrogenic delivery from those that occur too early to benefit from such intervention. Early FD is most commonly associated with infection and congenital anomalies. Late FD is more frequently associated with fetal growth restriction, placental abruption, or is idiopathic. The circumstances surrounding FD also vary according to socioeconomic factors. In high-income countries, FD is associated with fetal growth restriction or placental insufficiency, although in nearly half of the cases, the etiology is unknown. Intrapartum complications, PE, and infection play a more important role in the etiology of FD in low-income countries. FD or stillbirth occurs when a fetus dies before delivery which was not a consequence of an induced termination of pregnancy. A miscarriage is a type of FD that occurs before the 20th week of pregnancy or before the fetus is viable.

Placenta-related causes of FD include placental abruption, placental lesions, and placental lesions suggestive of maternal vascular underperfusion. Examples of placental lesions include, persistent muscularization of basal plate arteries, increased syncytial knot, increased intervillous fibrin, prominent nucleated red blood cells, absence of physiologic change of the spiral arteries, hyalinized avascular villi, microscopic chorionic pseudo cysts in placental membranes, and villous infarction.

Massive perivillous fibrin deposition of the placenta (MPFD) or MFI is a serious condition associated with recurrent complications including FD and severe fetal growth restriction. MPFD or MFI is characterized by the extensive deposition of fibrinoid materials surrounding chorionic villi, hampering gas and nutrient exchange in the intervillous space. This condition is associated with recurrent serious adverse pregnancy outcomes including miscarriage, fetal growth restriction, and stillbirth. An imbalance of angiogenic/anti-angiogenic factors is present in subjects with MFI prior to diagnosis.

Risk assessment for severe late PE and stillbirth in the third trimester is possible with the determination of maternal plasma concentrations of angiogenic and anti-angiogenic factors at 30-34 weeks of gestation. Accordingly, biomarkers disclosed herein may be useful as an additional tool for risk stratification in future interventional trials for the prevention of stillbirth and/or severe late PE at or near term. A specific clinical example is that subjects at risk for stillbirth after being identified by the markers proposed herein can undergo intensive antepartum surveillance and deliver the fetus at or near term once the risks of prolonging pregnancy outweigh those of complications of prematurity.

The present disclosure provides for assessing the presence or risk of obstetrical complications and/or an angiogenic and anti-angiogenic imbalance in a subject by assaying the ratios of an angiogenic factor to an anti-angiogenic factor. The present disclosure also provides methods of assessing the risk of FD with placental lesions, for example, placental lesions associated with maternal vascular underperfusion, by assaying concentrations of angiogenic and anti-angiogenic factors.

In various embodiments, the presence or risk of obstetrical complications and/or an angiogenic and anti-angiogenic imbalance in a subject is assessed by determining the multiple of the median (MoM) of the maternal plasma concentration ratio of the angiogenic factor and anti-angiogenic factor in a biological sample. In some embodiments, the angiogenic factor is PIGF. In some embodiments, the anti-angiogenic factor is sVEGFR-1 and/or sEng.

Multiple of the median (MoM) is a measure of how far an individual test result deviates from a relevant median. A MoM can be calculated by dividing a particular subject's test result by an expected median value of uncomplicated pregnancy at the same GA (derived from median regression analysis of the same subject population). Use of MoM scores herein curtails some of the impacts that developmental regulation of angiogenic/anti-angiogenic factors has on distributional patterns and/or estimated prognostic performance. Thus, the findings generated and reported herein are inherently different from those of other reports because MoMs better describes each subject's analyte concentration in relation to the expected concentration for the unique GA at which venipuncture was performed. A major benefit of this approach is that the findings are easier to interpret, and are more generalizable to independent populations because results are expressed in relation to expectations given for the stage of gestation at venipuncture, rather than in relation to more extreme thresholds which are more difficult to estimate.

In some embodiments, the obstetrical complications are associated with an angiogenic and anti-angiogenic imbalance. In various embodiments, the obstetrical complications are present without the presence of fetal congenital abnormalities. In various embodiments, the obstetrical complications are not related to infection. In some embodiments, the methods disclosed herein assess the presence or risk of the obstetrical complications of FD at or near term, severe PE, and/or severe late PE.

In some embodiments, the FD is associated with placental abruption, fetal growth restriction, or is idiopathic. In some embodiments, the FD is not associated with congenital abnormalities or infection.

In some embodiments, the biological sample is plasma or serum. In various embodiments, the biological sample may be obtained in the third trimester of pregnancy. In one embodiment the biological sample is obtained between 30th week of pregnancy and 34th week of pregnancy.

In one embodiment, the biological sample is obtained in the late second trimester. In another embodiment, the biological sample is obtained between the 24th week of pregnancy and the 28th week of pregnancy.

In various embodiments, the biological sample is obtained after the 25th week of pregnancy, after the 26th week of pregnancy, after the 27th week of pregnancy, after the 28th week of pregnancy, after the 29th week of pregnancy, after the 30th week of pregnancy, after the 31st week of pregnancy, after the 32nd week of pregnancy, after the 33rd week of pregnancy, after the 34th week of pregnancy, after the 35th week of pregnancy, after the 36th week of pregnancy, after the 37th week of pregnancy, after the 38th week of pregnancy, after the 39th week of pregnancy, or after the 40th week of pregnancy.

In various embodiments, the biological sample is obtained between the 30th week of pregnancy and the 31st week, the 32nd week, the 33rd week, the 34th week, the 35th week, the 36th week, the 37th week, the 38th week, the 39th week, the 40th week of pregnancy, or birth. In various embodiments, the biological sample is obtained between the 25th week of pregnancy and the 26th week, the 27th week, or the 28th week of pregnancy.

In various embodiments, the methods assess the presence or risk of an obstetrical complication with a specificity of 80% or greater, 81% or greater, 82% or greater, 83% or greater, 84% or greater, 85% or greater, 86% or greater, 87% or greater, 88% or greater, 89% or greater, 90% or greater, 91% or greater, 92% or greater, 93% or greater, 94% or greater, 95% or greater, 96% or greater, 97% or greater, 97% or greater, 98% or greater or 99% or greater.

In various embodiments, the methods assess the presence or risk of an obstetrical complication with a sensitivity of 40% or greater, 45% or greater, 50% or greater, 55% or greater, 58% or greater, 60% or greater, 65% or greater, 70% or greater, 75% or greater, 80% or greater, 85% or greater, 87.5%% or greater, 90% or greater, or 95% or greater, 99%% or greater, and/or 100%.

One embodiment includes a method for assessing the presence or risk of obstetrical complications in a subject by determining the MoM of the maternal plasma concentration ratio of PIGF/sVEGFR-1 and/or the MoM of the maternal plasma concentration ratio of PIGF/sEng in a biological sample; and comparing the MoM of the maternal plasma concentration ratio to a threshold to assess the presence or risk of obstetrical complications. In one embodiment, a MoM of the maternal plasma concentration ratio below the threshold of 0.4 indicates the presence or risk of obstetrical complications. In various embodiments, a MoM of the maternal plasma concentration ratio below a threshold of 0.025, 0.05, 0.075, 0.1, 0.12, 0.125, 0.15, 0.175, 0.196, 0.2, 0.225, 0.25, 0.275, 0.3, 0.325, 0.326, 0.336, 0.35, 0.375, 0.3989, 0.4, 0.425, 0.45, 0.475, 0.5, 0.6, 0.7, or 0.8, indicates the presence or risk of obstetrical complications.

One embodiment includes a method for assessing the presence or risk of obstetrical complications in a subject by determining the MoM of the maternal plasma concentration ratio of PIGF/sVEGFR-1 and/or the MoM of the maternal plasma concentration ratio of PlGF/sEng in a biological sample; comparing the MoM of the maternal plasma concentration ratio to a threshold of 0.3, wherein a MoM of the maternal plasma concentration ratio of PlGF/sVEGFR-1 and/or a MoM of the maternal plasma concentration ratio of PlGF/sEng of <0.3 indicates the presence or risk of one or more obstetrical complications selected from PE, severe PE, severe late PE, and SGA. In one embodiment, a MoM of the maternal plasma concentration ratio of PlGF/sVEGFR-1<0.12 indicates the presence or risk of obstetrical complications of FD or placental lesions. In another embodiment, a MoM of the maternal plasma concentration ratio of PlGF/sEng<0.2 indicates the presence or risk of obstetrical complications of FD and/or placental lesion suggestive of maternal vascular underperfusion.

One embodiment includes a method for assessing the presence or risk of obstetrical complications in a subject by determining the MoM of the maternal plasma concentration ratio of PlGF/sVEGFR-1 and/or the MoM of the maternal plasma concentration ratio of PlGF/sEng in a biological sample and comparing the MoM of the maternal plasma concentration ratio to a threshold, wherein a MoM of the maternal plasma concentration ratio of PlGF/sVEGFR-1 of <0.375 indicates the presence or risk of obstetrical complications of FD and/or placental lesion suggestive of maternal vascular underperfusion. In another embodiment, a MoM of the maternal plasma concentration ratio of PlGF/sEng of <0.3989 indicates the presence or risk of obstetrical complications of FD and/or placental lesion suggestive of maternal vascular underperfusion.

In various embodiments, the biomarkers described herein can be assayed using any suitable method, such as enzyme-linked immunosorbent assay (ELISA), a radioimmunoassay (RIA), gene expression assays, a Western blot, an immuno-precipitation, an immunohistochemical staining, flow cytometry, a Northern blot, magnetic immunoassay, RT-qPCR, hybridization microarray, fluorescence-activated cell sorting (FACS), an enzyme substrate color method, and/or an antigen-antibody agglutination.

Systems disclosed herein include kits to assay the biomarkers disclosed herein. Also disclosed herein are kits including one or more antibodies, binding proteins, primers and/or probes to assay the biomarkers described herein. In various embodiments, the kits may include one or more containers containing one or more antibodies, binding proteins, primers and/or probes to be used to assay the biomarkers described herein. Associated with such container(s) can be a safety notice. In particular embodiments, kits disclosed herein include antibodies, binding proteins, primers, probes, and amplification and detection reagents, detectable labels or subsets thereof.

In various embodiments, the kits may include instructions for using the kit in the methods disclosed herein. In various embodiments, the kit may include instructions regarding preparation of the antibodies, binding proteins, primers and/or probes, use of the antibodies, binding proteins, primers and/or probes, proper disposal of the related waste, and the like. The instructions can be in the form of printed instructions provided inside a carton containing the kit. The instructions can also be printed on the carton and/or on other portions of the kit. Instructions may be in the form of a sheet, pamphlet, brochure, CD-ROM, or computer-readable device, or can provide directions to instructions at a remote location, such as a website. The instructions may be in English and/or in any national or regional language.

In various embodiments, the kits described herein include some or all of the necessary supplies needed to use the kit, thereby eliminating the need to locate and gather such supplies. The supplies can include pipettes, pipette tips, buffers, reagents, plates, films, tubes, thermocyclers, tube racks, gloves, sterilizing liquids, and the like.

In various embodiments, the packaging, antibodies, binding proteins, primers and/or probes, and instructions are combined into a small, compact kit with printed instructions for use of each of the antibodies, binding proteins, primers and/or probes. In various embodiments in which more than antibody, binding protein, pair of primers and/or probes is provided, the sequencing of use of the antibodies, binding proteins, primers and/or probes can be labeled in the kit. Variations in contents of any of the kits described herein can be made.

When an obstetrical complication is detected, the systems and methods disclosed herein provide effective interventions.

In various embodiments, treating a pregnant subject includes delivering a therapeutically effective amount of a water-soluble statin. Also provided is treatment for obstetrical complications by administration of a therapeutically effective amount of a statin. Additional embodiments disclosed herein include methods of treating an angiogenic and anti-angiogenic imbalance in a pregnant subject including administering a therapeutically effective amount of a water-soluble statin to the subject thereby treating the angiogenic and anti-angiogenic imbalance. Exemplary water-soluble statins include pravastatin and rosuvastatin.

Methods disclosed herein include treating subjects (humans, veterinary animals (dogs, cats, reptiles, birds, etc.) livestock (horses, cattle, goats, pigs, chickens, etc.) and research animals (monkeys, rats, mice, fish, etc.) with water-soluble statins as disclosed herein including salts and prodrugs thereof. Treating subjects includes delivering therapeutically effective amounts. Therapeutically effective amounts include those that provide effective amounts, prophylactic treatments, and/or therapeutic treatments.

An "effective amount" is the amount of a statin necessary to result in a desired physiological change in the subject. Effective amounts are often administered for research purposes. Effective amounts disclosed herein reduce, control, or eliminate the presence or side effects of an angiogenic and anti-angiogenic imbalance or an obstetrical complication.

A "prophylactic treatment" includes a treatment administered to a subject who does not display signs or symptoms of an angiogenic and anti-angiogenic imbalance or an obstetrical complication, displays only early signs or symptoms of the angiogenic and anti-angiogenic imbalance or the obstetrical complication, or displayed signs or symptoms of an angiogenic and anti-angiogenic imbalance or an obstetrical complication in a previous pregnancy, such that treatment is administered for the purpose of diminishing, preventing, or decreasing the risk of developing the angiogenic and anti-angiogenic imbalance or the obstetrical complication further. Thus, a prophylactic treatment functions as a preventative treatment against an angiogenic and anti-angiogenic imbalance or an obstetrical complication.

A "therapeutic treatment" includes a treatment administered to a subject who displays symptoms or signs of an angiogenic and anti-angiogenic imbalance or an obstetrical complication and is administered to the subject for the purpose of diminishing or eliminating those signs or symptoms of the angiogenic and anti-angiogenic imbalance or the obstetrical complication. The therapeutic treatment can reduce, control, or eliminate the presence of an angiogenic and anti-angiogenic imbalance or an obstetrical complication and/or reduce control or eliminate side effects of an angiogenic and anti-angiogenic imbalance or an obstetrical complication.

For administration, therapeutically effective amounts (also referred to herein as doses) can be initially estimated based on results from in vitro assays and/or animal model studies. Such information can be used to more accurately determine useful doses in subjects of interest. Therapeutically effective amounts need not fully prevent or cure an angiogenic and anti-angiogenic imbalance or an obstetrical complication but can also provide a partial benefit, such as delay of onset or alleviation or improvement of at least one symptom of the angiogenic and anti-angiogenic imbalance or the obstetrical complication.

The actual dose amount administered to a particular subject can be determined by a physician, veterinarian or researcher taking into account parameters such as physical and physiological factors including target, body weight, severity of condition, type of obstetrical complication, previous or concurrent therapeutic interventions, idiopathy of the subject, and route of administration.

The amount and concentration of statin in a pharmaceutical composition, as well as the quantity of the pharmaceutical composition administered to a subject, can be selected based on clinically relevant factors, the solubility of the statin in the pharmaceutical composition, the potency and activity of the statin, and the manner of administration of the pharmaceutical composition. A pharmaceutical composition including a therapeutically effective amount of a statin, or a pharmaceutically acceptable salt or prodrug thereof, can be administered intravenously to a subject for treatment of an obstetrical complication in a clinically safe and effective manner, including one or more separate administrations of the composition. For example, 0.05 mg/kg to 5.0 mg/kg can be administered to a subject per day in one or more doses (e.g., doses of 0.05 mg/kg QD, 0.10 mg/kg QD, 0.50 mg/kg QD, 1.0 mg/kg QD, 1.5 mg/kg QD, 2.0 mg/kg QD, 2.5 mg/kg QD, 3.0 mg/kg QD, 0.75 mg/kg BID, 1.5 mg/kg BID or 2.0 mg/kg BID). For certain antiviral indications, the total daily dose of a statin can be 0.05 mg/kg to 3.0 mg/kg administered intravenously to a subject one to three times a day, including administration of total daily doses of 0.05-3.0, 0.1-3.0, 0.5-3.0, 1.0-3.0, 1.5-3.0, 2.0-3.0, 2.5-3.0, and 0.5-3.0 mg/kg/day using 60-minute QD, BID or TID intravenous infusion dosing. In one particular example statins can be intravenously administered QD or BID to a subject with, e.g., total daily doses of 1.5 mg/kg, 3.0 mg/kg, 4.0 mg/kg. The amount per administered dose and the total amount administered will depend on factors such as the nature and severity of the infection, the age and general health of the subject, the tolerance of the subject to the statin.

Useful doses can often range from 0.1 to 5 µg/kg or from 0.5 to 1 µg/kg. In other examples, a dose can include 1 µg/kg, 5 µg/kg, 10 µg/kg, 15 µg/kg, 20 µg/kg, 25 µg/kg, 30 µg/kg, 35 µg/kg, 40 µg/kg, 45 µg/kg, 50 µg/kg, 55 µg/kg, 60 µg/kg, 65 µg/kg, 70 µg/kg, 75 µg/kg, 80 µg/kg, 85 µg/kg, 90 µg/kg, 95 µg/kg, 100 µg/kg, 150 µg/kg, 200 µg/kg, 250 µg/kg, 350 µg/kg, 400 µg/kg, 450 µg/kg, 500 µg/kg, 550 µg/kg, 600 µg/kg, 650 µg/kg, 700 µg/kg, 750 µg/kg, 800 µg/kg, 850 µg/kg, 900 µg/kg, 950 µg/kg, 1000 µg/kg, 0.1 to 5 mg/kg or from 0.5 to 1 mg/kg. In other examples, a dose can include 1 mg/kg, 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 55 mg/kg, 60 mg/kg, 65 mg/kg, 70 mg/kg, 75 mg/kg, 80 mg/kg, 85 mg/kg, 90 mg/kg, 95 mg/kg, 100 mg/kg, 150 mg/kg, 200 mg/kg, 250 mg/kg, 350 mg/kg, 400 mg/kg, 450 mg/kg, 500 mg/kg, 550 mg/kg, 600 mg/kg, 650 mg/kg, 700 mg/kg, 750 mg/kg, 800 mg/kg, 850 mg/kg, 900 mg/kg, 950 mg/kg, 1000 mg/kg or more.

Therapeutically effective amounts can be achieved by administering single or multiple doses during the course of a treatment regimen (e.g., daily, every other day, every 3 days, every 4 days, every 5 days, every 6 days, weekly, every 2 weeks, every 3 weeks, monthly, every 2 months, every 3 months, every 4 months, every 5 months, every 6 months, every 7 months, every 8 months, every 9 months, every 10 months, every 11 months, or yearly.

A desired physiological change in a subject includes the reversal of an angiogenic and anti-angiogenic imbalance and/or the reduction, reversal or prevention of an obstetrical complication selected from one or more of miscarriage, implantation failure, PE, late PE, severe PE, severe late PE, SGA neonates, preterm labor, FD, placenta-related causes of FD, fetal growth restriction, maternal vascular underperfusion, placental lesions, placental abruption, premature rupture of the membranes, preterm premature rupture of the membranes, mirror syndrome, molar pregnancy, twin-to-twin transfusion syndrome, anhydramnios, placental perivillous fibrin deposition, and placental findings suggestive of MF.

Statins have the potential to reverse the abnormalities in angiogenic/anti-angiogenic factors demonstrated in stillbirths of unknown etiology, and therefore, may represent an intervention with subjects identified with the approach herein. Other proposed therapeutic interventions to reverse an angiogenic and anti-angiogenic imbalance during pregnancy include the administration of VEGF 121 or extracorporeal removal of sVEGFR-1.

Although statins are pregnancy category X drugs, there are only a few reports of teratogenic effects in humans despite the theoretical concern that inhibition of cholesterol synthesis during embryonic development can interfere with sonic hedgehog signal transduction. The reported congenital anomalies included isolated anomalies such as central nervous system or limbs defects and the VACTERL association (especially for lipophilic statins). However, abnormal pregnancy outcomes were not reported following exposure to pravastatin or fluvastatin. Furthermore, higher doses than commonly prescribed in humans were used in the animal studies in which congenital anomalies were associated with exposure to statins, and post marketing surveillance of lovastatin and simvastatin has not found any adverse pregnancy outcomes in subjects with an early exposure to these drugs. A recent systematic review and meta-analysis concluded that statins are unlikely to be teratogenic in humans.

Pravastatin, a 3-hydroxy-3-methyl-glutaryl-coenzyme-A reductase inhibitor, is a cholesterol-lowering agent. This agent has been used to lower blood cholesterol and reduce the risk of acute coronary syndrome, stroke and death due to atherosclerotic vascular disease in non-pregnant subjects. In animal models of PE, pravastatin has been shown to reverse imbalances in angiogenic/anti-angiogenic factors, ameliorate high blood pressure, improve vascular function as assessed by in vitro carotid artery vascular reactivity, decrease circulating sVEGFR-1 and sEng as well as increase PlGF and VEGF concentrations. Animal studies reported increased serum concentrations of PlGF, as well as a decrease in sVEGFR-1 and mRNA expression of hypoxic inducible factor-1a by trophoblasts in response to pravastatin. Pravastatin also stimulates VEGF synthesis in endothelial and vascular smooth muscle cells and improves endothelial cell function (without significant changes in cholesterol concentration) through increased bioavailability of endothelial nitric oxide synthase, up-regulation of heme-oxygenase-1 enzyme (which reduces oxidative stress and improves placental angiogenesis), reduction of inflammation, and inhibition of complement, as well as activation of tissue factor.

The pharmacokinetics of pravastatin also favors its use during pregnancy, because this drug, unlike other statins that are lipophilic, is water soluble, and therefore, penetrates the placental barrier slowly. In an experimental model using dually perfused term human placental lobule, 14% of pravastatin was retained by the placental tissue, 68% remained in the maternal circuit, and only 18% was transferred to the fetal circuit. There was a higher transfer of pravastatin from the fetal to the maternal compartment than the reverse.

Fluvastatin is used to treat hypercholesterolemia and to prevent cardiovascular disease. Lovastatin is a naturally occurring drug used to lower cholesterol in those with hypercholesterolemia to reduce risk of cardiovascular disease. Simvastatin is a lipid lowering medication, and is used to decrease the risk of heart problems in those at high risk.

One embodiment includes a method of treating obstetrical complications associated with an angiogenic and anti-angiogenic imbalance in a pregnant subject including administering pravastatin to the pregnant subject. In one embodiment, the method also includes administering heparin and aspirin to the pregnant subject. In one embodiment, the method includes assessing the presence or risk of obstetrical complications by assaying maternal plasma concentrations of angiogenic factors and anti-angiogenic factors. In one embodiment, the method includes assessing the presence of an angiogenic and anti-angiogenic imbalance in the pregnant subject. In one embodiment, the risk of obstetrical complications is assessed between the 26th week of pregnancy and the 40th week of pregnancy.

EXAMPLES

The Examples below are included to demonstrate particular embodiments of the disclosure. Those of ordinary skill in the art should recognize in light of the present disclosure that many changes can be made to the specific embodiments disclosed herein and still obtain a like or similar result without departing from the spirit and scope of the disclosure.

Example 1. Identification of Subjects at Risk for Stillbirth At or Near Term and Severe Late PE Using Maternal Plasma Concentrations of Angiogenic/Anti-angiogenic Factors in the Third Trimester of Pregnancy The objective of this example was to determine if maternal plasma concentrations of PlGF, sEng, sVEGFR-1 and their ratios at 30-34 weeks of gestation could be used to identify subjects at risk for obstetrical complications, such as stillbirth, late PE, severe late PE, or SGA without PE.
Methods.

Study Design. The study was designed with a cohort of women who had a venipuncture between 30-34 weeks of gestation, and outcome data to examine the value of PlGF, sVEGFR-1, and sEng in the identification of subjects who subsequently developed late PE, severe late PE, stillbirth, and SGA. Subsequent to this cohort study, a case-control study was performed to determine if these biomarkers and their ratios could identify subjects at risk for stillbirth at, or near, term in a different population.

Cohort Study. A prospective longitudinal cohort study was conducted to identify biological markers for the prediction of PE, SGA, and stillbirth. Subjects were enrolled in the prenatal clinic and followed until delivery. Inclusion criteria were: 1) singleton gestation; and 2) 6-22 weeks of gestation. Exclusion criteria were: 1) preterm labor, preterm prelabor rupture of membranes, PE, or impaired fetal growth at the time of recruitment; 2) known major fetal anomaly or fetal demise; 3) active vaginal bleeding; and 4) serious medical illness (renal insufficiency, congestive heart disease, chronic respiratory insufficiency, or active hepatitis). At enrollment and each subsequent visit, subjects underwent a venipuncture for the collection of maternal blood. The protocol consisted of collecting samples every 4 weeks until 24 weeks, and every 2 weeks thereafter until delivery.

The diagnostic performance of angiogenic/anti-angiogenic factors at 6-15 weeks and 20-25 weeks of gestation, as well as UtADV at 20-25 weeks of gestation in the prediction of PE from this cohort study has previously been reported. In summary, 2,998 consecutive women were enrolled during the study period mentioned above; 2,495 women had a plasma sample collected in early pregnancy. Of those, 1,917 women had an additional plasma sample obtained in the mid-trimester. Subsequently, an additional 204 subjects without results of UADV in the second trimester were excluded. Ninety-one subjects were lost to follow-up; the remaining 1,622 subjects had been included in a previous publication examining the role of angiogenic/anti-angiogenic factors at 6-15 weeks and 20-25 weeks of gestation. The current study involved a subset of this cohort, which excluded subjects who delivered at or before 34 weeks of gestation (n=27), as well as those who did not have a plasma sample collected between 30-34 weeks of gestation (n=326) to examine the role of angiogenic/anti-angiogenic factors at 30-34 weeks for the identification of adverse pregnancy outcomes after 34 weeks of gestation.

All women provided written informed consent before participating in the study. The use of clinical and ultrasound data and collection and utilization of maternal blood for research purposes was approved by the relevant Institutional Review Boards.

Outcomes of the Study. The outcomes of the study included late PE, severe late PE, SGA without PE and stillbirth. PE was defined as new-onset hypertension that developed after 20 weeks of gestation and proteinuria. Hypertension was defined as systolic≥140 and/or diastolic blood pressure≥90 mm Hg, measured at two occasions, 4 hours to 1 week apart. Proteinuria was defined as a urine protein of ≥300 mg in a 24-hour urine collection, or two random urine specimens, obtained 4 hours to 1 week apart, showing ≥1+ by dipstick or one dipstick demonstrating ≥2+ protein. Late PE was defined as subjects with PE who delivered after 34 weeks of gestation. Severe PE was diagnosed based on American College of Obstetricians and Gynecologists (ACOG) criteria. The ACOG criteria for severe PE is the presence of one or more of the following criteria: blood pressure of 160 mm Hg systolic or higher, or 110 mm Hg diastolic or higher on two occasions at least 6 hours apart while the subject is on bed rest; proteinuria of 5 g or higher in a 24-hour urine specimen, or 3+ or greater on two random urine samples collected at least 4 hours apart; oliguria of less than 500 mL in 24 hours; cerebral or visual disturbances; pulmonary edema or cyanosis; epigastric or right upper-quadrant pain; impaired liver function; thrombocytopenia; and fetal growth restriction.

The SGA was defined as a birthweight<$10^{th}$ percentile for GA according to the local birthweight distribution of the population. Stillbirth was defined as death of a fetus prior to delivery which is not a consequence of an induced termination of pregnancy (including intrapartum and antepartum stillbirth). Abnormal UADV was defined as the mean UtA Doppler pulsatility index (PI)>1.45.

Sample collection and immunoassays. Blood was obtained by venipuncture and collected into tubes containing EDTA. Samples were centrifuged and stored at −70° C. Maternal plasma concentrations of sVEGFR-1, PlGF, and sEng were determined by sensitive and specific immunoassays (R&D Systems). The inter- and intra-assay coefficients of variation (CV) were: 1.4% and 3.9% for sVEGFR-1, 2.3% and 4.6% for sEng, and 6.02% and 4.8%, respectively, for PlGF. The sensitivity of the assays was 16.97 μg/ml for sVEGFR-1, 0.08 ng/ml for sEng, and 9.52 μg/ml for PlGF. The laboratory personnel performing the assays were blinded to the clinical information.

Statistical analysis. Differences in distributions of dichotomous and categorical variables were tested using Chi-square or Fisher's Exact Test where appropriate; continuous parameters were compared by analysis of variance (ANOVA) or Friedman's two-way nonparametric ANOVA test with Bonferroni correction for multiple comparisons depending on the distribution of data. Normality was assessed using the Kolmogorov-Smirnov test and visual plot inspection.

Quantile regression was used to calculate median analyte ratio concentrations (PlGF/sVEGFR-1, PlGF/sEng) conditional upon GA among uncomplicated pregnancies (n=886). MoM values were calculated for both analyte ratios for each subject. MoM cutoffs were calculated based on inspection of receiver operating characteristic (ROC) curves calculated for each outcome (stillbirth, late PE, severe late PE, and SGA without PE). Prognostic logistic regression models were constructed for each outcome, including the MoM cutoff and clinical risk factors. Covariables included in adjusted models were selected based on clinical knowledge. Model reduction was performed additionally based on the plausibility of regression coefficients, association with independent variables and the magnitude of change in the main effect parameter estimates. To account for potential model over-fitting, when van Houwelingen and le Cessie's heuristic shrinkage estimator fell below 0.85 (indicator of instability), bootstrap estimated linear shrinkage factors and Firth's penalized maximum likelihood estimation were used to calculate conservative estimates less likely to be affected by over-fitting.

Diagnostic performance metrics were also calculated for each outcome. Paired sample non-parametric statistical techniques were used to compare area under the ROC curves (AUC) of models constructed using logistic regression for the identification of selected pregnancy outcomes. A McNemar's test was also used to test for differences in sensitivity at a fixed false positive rate of 15%. A 5% threshold for type I error was used to determine statistical significance. Statistical analyses were performed using SAS version 9.3 (Cary, NC, USA).

Case-Control Study for Stillbirth. Participants were identified from a cohort of 5,828 singleton pregnancies who were enrolled in a similar longitudinal protocol and another cross-sectional protocol. Stillbirth was defined as death of a fetus prior to delivery (which is not a consequence of an induced termination of pregnancy). In the longitudinal study, plasma samples were obtained from the first or early second trimester and at the time of each prenatal visit, scheduled every 4 weeks until 24 weeks, and every 2 weeks thereafter until delivery. In the cross-sectional study, subjects were enrolled when they presented to the labor and delivery unit with a suspicion of spontaneous preterm labor or medically indicated preterm birth. Among 31 cases of stillbirth at 234 weeks of gestation, five had a plasma sample collected between 30-34 weeks of gestation and were included. Controls were identified from uncomplicated pregnancies who delivered an appropriate weight for GA neonate at term, and had a plasma sample collected between 30 and 34 weeks of gestation. Controls were matched to cases at a ratio of 6 to 1 on GA at venipuncture, parity, ethnicity, tobacco use and body mass index (BMI). Maternal plasma concentrations of sVEGFR-1, sEng and PlGF were determined by sensitive and specific immunoassays similar to those used in the cohort as described above.

All women provided written informed consent before participating in the study. The use of clinical and ultrasound data and collection and utilization of maternal blood for research purposes was approved by the Institutional Review Boards.

Statistical Analysis for Case-Control Study. Differences among cases and controls were tested using the Chi-square, Fisher's Exact or Mann-Whitney U tests where appropriate. AUC was calculated and sensitivities and specificities were determined using absolute value thresholds for each biomarker ratio derived from inspection of ROG curves.

Results.

Figure 1:
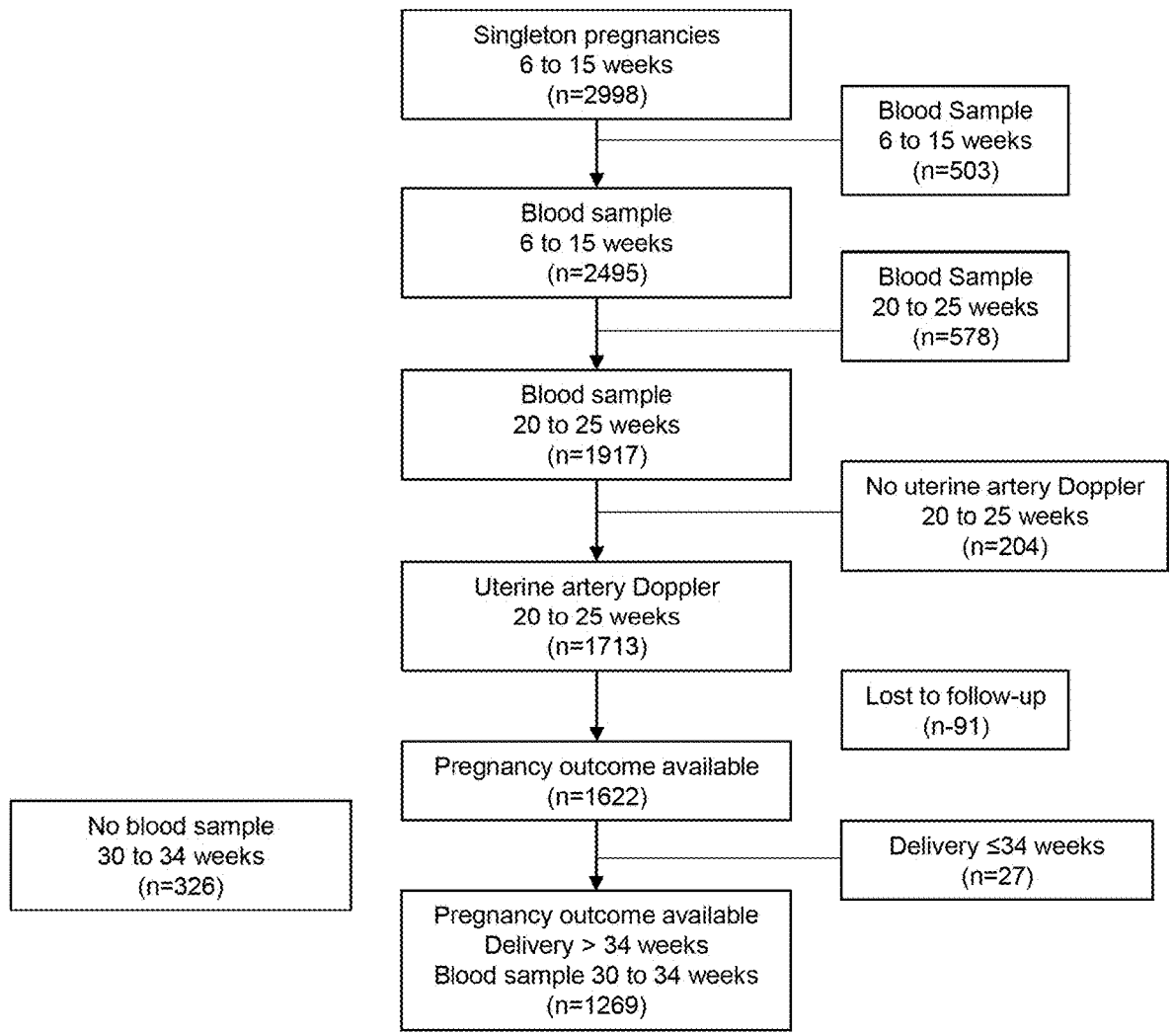
FIG. 1 is a flow diagram of subjects enrolled in a study using maternal plasma concentrations of angiogenic/anti-angiogenic factors in the third trimester of pregnancy to identify subjects at risk for stillbirth at or near term and severe late preeclampsia (PE).

The cohort study included 1,269 pregnant women (FIG. 1). The prevalence of late PE, severe late PE, stillbirth and SGA without PE was 3.2% (n=40), 1.8% (n=23); 0.4% (n=5), and 8.5% (n=108), respectively. Among 23 subjects who were diagnosed with severe PE, 6 experienced severe high blood pressure and severe proteinuria, 4 had severe high blood pressure, 4 had severe high blood pressure with severe proteinuria with SGA fetuses, 3 had SGA fetuses, 2 had severe headache with severe proteinuria, 2 had severe proteinuria, 1 had severe high blood pressure and the last one had severe proteinuria and pulmonary edema. Table 1 displays the demographic and obstetrical characteristics of subjects with SGA, PE, stillbirth, other complications (see table note) and those without any of these complications (uncomplicated pregnancy). There were no significant differences in the mean GA at venous sampling or mean duration of sample storage among the four groups. The distribution of baseline characteristics did not significantly differ between subjects included in this Example compared to the overall cohort. Similarly, there were no significant differences in the risk of stillbirth or SGA between the entire cohort and sub-cohort. However, by design, participants in the sub-cohort were more likely to deliver after 34 weeks of gestation. Subjects in this sub-cohort had a lower frequency of PE than those in the entire cohort (3.2% vs. 4.8%; p=0.03). There were three subjects diagnosed with gestational hypertension prior to venipuncture at 30-34 weeks of gestation. However, none subsequently developed PE. The median MoM plasma concentration of PlGF/sVEGFR-1 and PlGF/sEng was significantly lower in subjects with subsequent stillbirth, PE and SGA than those without these conditions (p<0.05 for each comparison; see Table 1)

TABLE 1

Demographic and obstetrical characteristics of study population.

| Subject Characteristics | Uncomplicated Pregnancy (n = 886) | SGA (n = 108) | PE (n = 40) | Stillbirth (n = 5) | Other complications (n = 230) |
|---|---|---|---|---|---|
| Maternal age (years) | 26.2 + 5.9 | 26.5 + 7.1 | 23.6 + 5.4* | 27 + 10 | 28 + 6.5 |
| Tobacco use | 10.5% (93) | 18.50% (20) | 12.50% (5) | 0 | 12.2% (28) |
| Nulliparous | 40.2% (356) | 44.4% (48) | 70%* (28) | 40% (2) | 33.0 (76) |
| Multiparous with previous history of PE | 2.1% (19) | 0.9% (1) | 7.5%* (3) | 0 | 6.1% (14) |
| Multiparous without previous history of PE | 57.7% (511) | 54.60% (59) | 22.50%* (9) | 60% (3) | 60.9% (140) |
| Body mass index (Kg/m$^2$) | 24.6 + 4.2 | 24 + 4.3 | 27.4 + 8 | 22.4 + 1.6 | 27.3 + 6 |
| GA at venipuncture (weeks) | 32.2 + 1.1 | 32.2 + 1.1 | 32.2 + 1.2 | 32 + 0.9 | 32.2 + 1.2 |
| Storage time (years) | 6.8 + 0.7 | 6.8 + 0.8 | 6.9 + 1.1 | 6.6 + 0.6 | 6.8 + 0.7 |
| GA at delivery (weeks) | 39.6 + 1.1 | 39.4 + 1.1 | 38.48* + 1.6 | 36.5* + 2.3 | 38.6 + 1.7 |
| Birthweight (grams) | 3505 + 399 | 2710* + 230 | 3096* + 550 | 2896 + 642 | 3366 + 521 |
| PIGF/SVEGFR-1 MoM (median (IQR)) | 1.00 (0.51-1.83) | 0.53* (0.21-1.22) | 0.21* (0.08-0.50) | 0.08* (0.07-0.1) | 0.73 (0.33-1.27) |
| PIGF/sEng MoM (median (IQR)) | 1.00 (0.56-1.78) | 0.59* (0.26-1.10) | 0.27* (0.11-0.63) | 0.18* (0.1-0.3) | 0.74 (0.35-1.18) |

Value expressed as percent (number), mean ± standard deviation or median (interquartile range-IQR);
*indicated significant difference (p < 0.05) compared to combined 'other + uncomplicated pregnancy' categories;
Medians were calculated among uncomplicated pregnancies (n = 886) by quantile regression
PIGF/sVEGFR-1 Median = 1.8863 + (−0.0508 * gestational week)
PIGF/sEng Median = 354.3280 + (−8.9791 * week)
Other complications include spontaneous preterm delivery (3%; n = 38), chronic hypertension (2.2%; n = 28), gestational hypertension (6.8%; n = 86); gestational and pregestational diabetes (4.6%; n = 58), placental abruption (0.4%; n = 5), cholestasis of pregnancy (0.9%; n = 12) and placenta previa (0.2%; n = 3)

Table 2 displays the magnitude of association between abnormal biomarker profiles and late PE (overall and severe), SGA (birthweight<10%, <3%) as well as stillbirth. Subjects with plasma PIGF/sEng or PIGF/sVEGFR-1 ratio concentrations<0.3 MoM were significantly more likely to develop late PE (adjusted odds ratio (aOR) 7.1; 95% confidence interval (CI) 3.6-13.8 and aOR 6.1; 95% CI 3.1-11.8; respectively) and severe late PE (aOR 16.1; 95% CI 5.8-44.6 and aOR 12.2; 95% CI 4.6-32; respectively) than those with MoM at or above the threshold (Table 2). The likelihood ratio (LR) of a positive test and sensitivity for either PIGF/sEng or PIGF/sVEGFR-1 ranged from 4.5-4.8 and 74%-78%, respectively; both had a specificity of 84% for the identification of subjects with severe late PE (Table 3).

TABLE 2

Likelihood (unadjusted and adjusted) of subsequent stillbirth, PE and SGA neonate by PIGF/sVEGFR-1 and PIGF/sEng MoM threshold

| Dependent Ratio & MOM Threshold Variable, Analyte | Others % (n/N) | Outcome % (n/N) | Unadjusted OR | 95% CI | | Adjusted* OR | 95% CI | |
|---|---|---|---|---|---|---|---|---|
| PE (n = 40) | | | | | | | | |
| PIGF/SVEGFR-1 <0.3 MOM | 16.2% (199/1229) | 57.5% (23/40) | 7.9 | 4.1 | 15.2 | 6.1 | 3.1 | 11.8 |
| PIGF/sEng <0.3 MoM | 15.9% (196/1229) | 60.0% (24/40) | 5.9 | 1.9 | 18.7 | 7.1 | 3.6 | 13.8 |
| Severe PE (n = 23) | | | | | | | | |
| PIGF/sVEGFR-1 <0.3 MOM | 16.5% (205/1246) | 73.9% (17/23) | 11.9 | 2.2 | 66 | 12.2 | .6 | 32 |
| PIGF/sEng <0.3 MoM | 16.3% (202/1246) | 78.3% (18/23) | 11.7 | 2.1 | 64.6 | 16.1 | 5.8 | 44.6 |
| SGA <10th % (n = 108) | | | | | | | | |
| PIGF/sVEGFR-1 <0.3 MOM | 15.8% (184/1161) | 35.2% (38/108) | 4.2 | 2.4 | 7.3 | 3 | 2 | 4.7 |
| PIGF/sEng <0.3 MoM | 16.3% (189/1161) | 28.7% (31/108) | 3.6 | 2 | 6.4 | 2 | 1.3 | 3.1 |
| SGA <3rd % (n = 23) | | | | | | | | |
| PIGF/SVEGFR-1 <0.3 MOM | 16.9% (210/1246) | 52.2% (12/23) | 6.9 | 2.4 | 19.4 | 5.5 | 2.3 | 13.1 |

TABLE 2-continued

Likelihood (unadjusted and adjusted) of subsequent stillbirth, PE and SGA neonate by PlGF/sVEGFR-1 and PlGF/sEng MoM threshold

| Dependent Ratio & MOM Threshold Variable, Analyte | Others % (n/N) | Outcome % (n/N) | Unadjusted | | | Adjusted* | | |
|---|---|---|---|---|---|---|---|---|
| | | | OR | 95% CI | | OR | 95% CI | |
| PlGF/sEng <0.3 MoM Stillbirth (n = 5) | 16.8% (209/1246) | 47.8% (11/23) | 7 | 2.5 | 19.8 | 4.4 | 1.8 | 10.4 |
| PlGF/SVEGFR-1 <0.12 MOM | 5.6% (71/1264) | 80% (4/5) | 20.1 | 4.8 | 84.3 | 23.1 | 5.6 | 95.4 |
| PlGF/sEng <0.2 MoM | 10.8% (137/1264) | 60% (3/5) | 8.4 | 2 | 35.1 | 9.1 | 2.2 | 37.2 |

OR = Odds Ratio,, ORs represent the likelihood of outcome in subjects with abnormal analyte ratio concentrations (above/below MoM cutoff) relative to subjects with normal analyte ratio concentration MoM. Medians were calculated among uncomplicated pregnancies (n = 886) by quantile regression (PlGF/sVEGFR-1 Median = 1.8863 + (−0.0508 *gestational week); PlGF/sEng Median = 354.3280 + (−8.9791*week)), cutoffs were selected based on inspection of ROC curves.
*Prediction of stillbirth adjusted for GA at venipuncture (continuous);
Prediction of PE and SGA adjusted for: maternal age (continuous), combined parity & history of PE, pre-pregnancy body mass index (continuous), tobacco use.
PlGF/sVEGFR-1 MoM cutoff <0.12 (or $5^{th}$-$6^{th}$ percentile of uncomplicated pregnancies) for stillbirth, <0.3 (or $17^{th}$ percentile of uncomplicated pregnancies) for PE and SGA.
PlGF/sEng MoM cutoff <0.2 (or $11^{th}$ percentile of uncomplicated pregnancies) for stillbirth, <0.3 (or $17^{th}$ percentile of uncomplicated pregnancies) for PE and SGA.

TABLE 3

Diagnostic performance of maternal plasma concentrations of angiogenic & anti-angiogenic factors for stillbirth and PE screening according to PlGF/sVEGFR-1 and PlGF/sEng MoM threshold.

| Diagnostic Performance Metrics | PE | | | | Stillbirth (n = 5) | |
|---|---|---|---|---|---|---|
| | Overall (n = 40) | | Severe (n = 23) | | | |
| | Estimate | 95% CI | Estimate | 95% CI | Estimate | 95% CI |
| PlGF/SVEGFR-1 | | | | | | |
| Sensitivity (%) | 58 | (40-73) | 74 | (52-90) | 80 | (28-100) |
| Specificity (%) | 83 | (82-86) | 84 | (81-86) | 94 | (93-96) |
| +predictive value (%) | 10 | (6-15) | 8 | (5-12) | 5 | (1-13) |
| −predictive value (%) | 98 | (97-99) | 99 | (99-100) | 100 | (99-100) |
| False + probability (%) | 16 | (14-18) | 16 | (14-19) | 6 | (4-7) |
| False − probability (%) | 43 | (27-59) | 26 | (10-48) | 20 | (0.5-72) |
| +LR | 3.6 | (2.6-4.8) | 4.5 | (3.4-5.9) | 14.2 | (8.7-23.3) |
| −LR | 0.5 | (0.4-0.7) | 0.3 | (0.2-0.6) | 0.2 | (0.04-1.22) |
| PlGF/sEng | | | | | | |
| Sensitivity (%) | 60 | (43-75) | 78 | (56-93) | 60 | (15-95) |
| Specificity (%) | 84 | (82-86) | 84 | (82-86) | 89 | (87-91) |
| +predictive value (%) | 11 | (7-16) | 8 | (5-13) | 2 | (0.4-6) |
| −predictive value (%) | 98 | (97-99) | 99 | (99-100) | 99 | (99-100) |
| False + probability (%) | 16 | (14-18) | 16 | (14-18) | 11 | (9-13) |
| False − probability (%) | 40 | (25-57) | 22 | (7-44) | 40 | (5-85) |
| +LR | 3.8 | (2.8-5.0) | 4.8 | (3.8-6.2) | 5.5 | (2.7-11.5) |
| −LR | 0.5 | (0.3-0.7) | 0.3 | (0.1-0.6) | 0.4 | (0.2-1.3) |

Medians were calculated among uncomplicated pregnancies (n = 886) by quantile regression (PlGF/sVEGFR-1 Median = 1.8863 + (−0.0508 *gestational week); PlGF/sEng Median = 354.3280 + (−8.9791*week)), cutoffs were selected based on inspection of ROC curves.
PlGF/sVEGFR-1 MoM cutoff <0.12 (or $5^{th}$-$6^{th}$ percentile of uncomplicated pregnancies) for stillbirth, <0.3 (or $17^{th}$ percentile of uncomplicated pregnancies) for PE.
PlGF/sEng MoM cutoff <0.2 (or $11^{th}$ percentile of uncomplicated pregnancies) for stillbirth, <0.3 (or $17^{th}$ percentile of uncomplicated pregnancies) for PE.

Figure 2A:
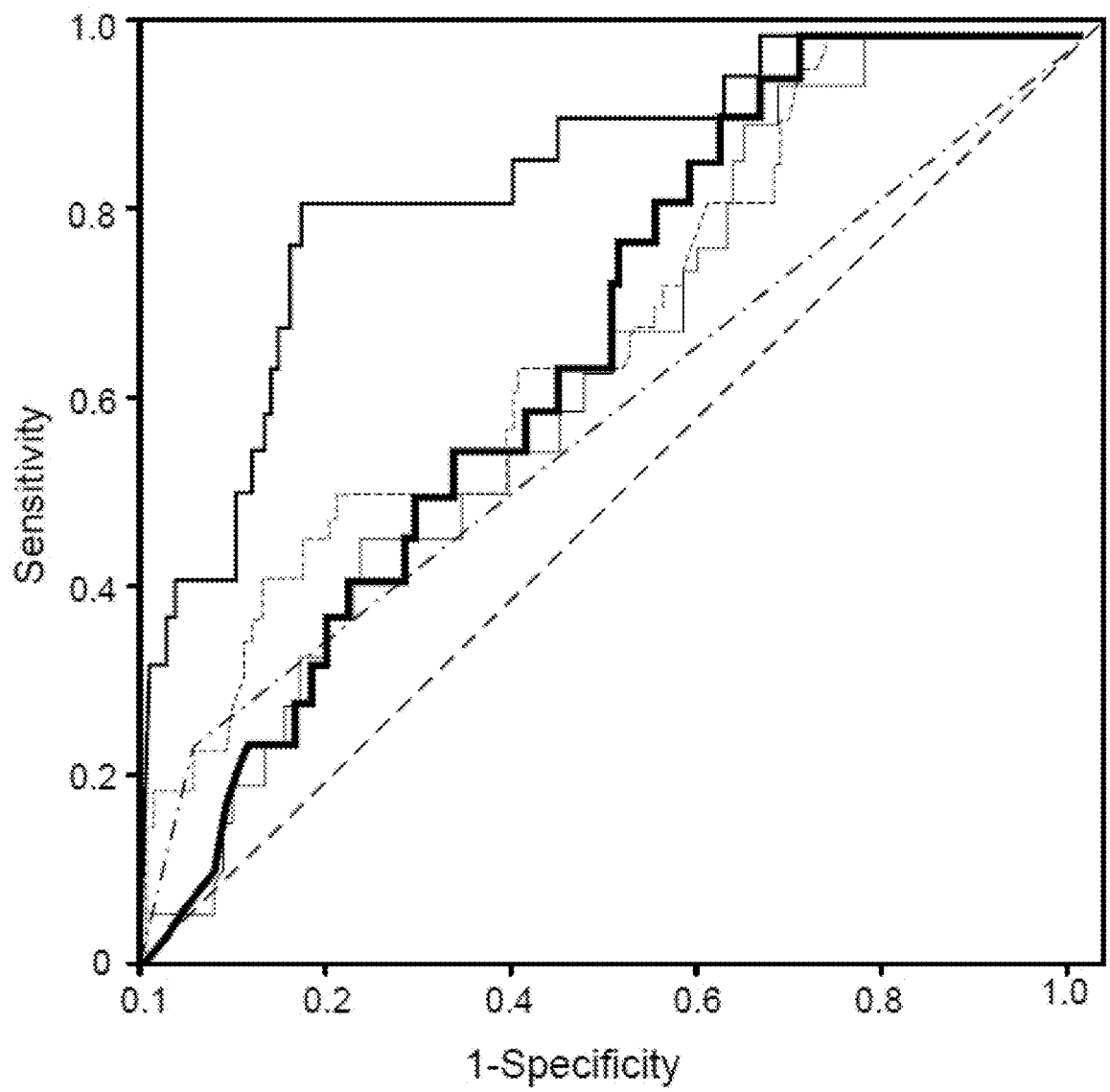
FIG. 2A and FIG. 2B show a comparison of receiver-operating characteristic (ROC) curves for the identification of severe late PE using Multiples of the Median (MoM) of the ratio of plasma concentrations of PlGF/sEng (FIG. 2A) or PlGF/sVEGFR-1 (FIG. 2B) at 6-15, 20-25, and 30-34 weeks of gestation and uterine artery Doppler velocimetry (UtADV) at 20-25 weeks of gestation.
Figure 2B:
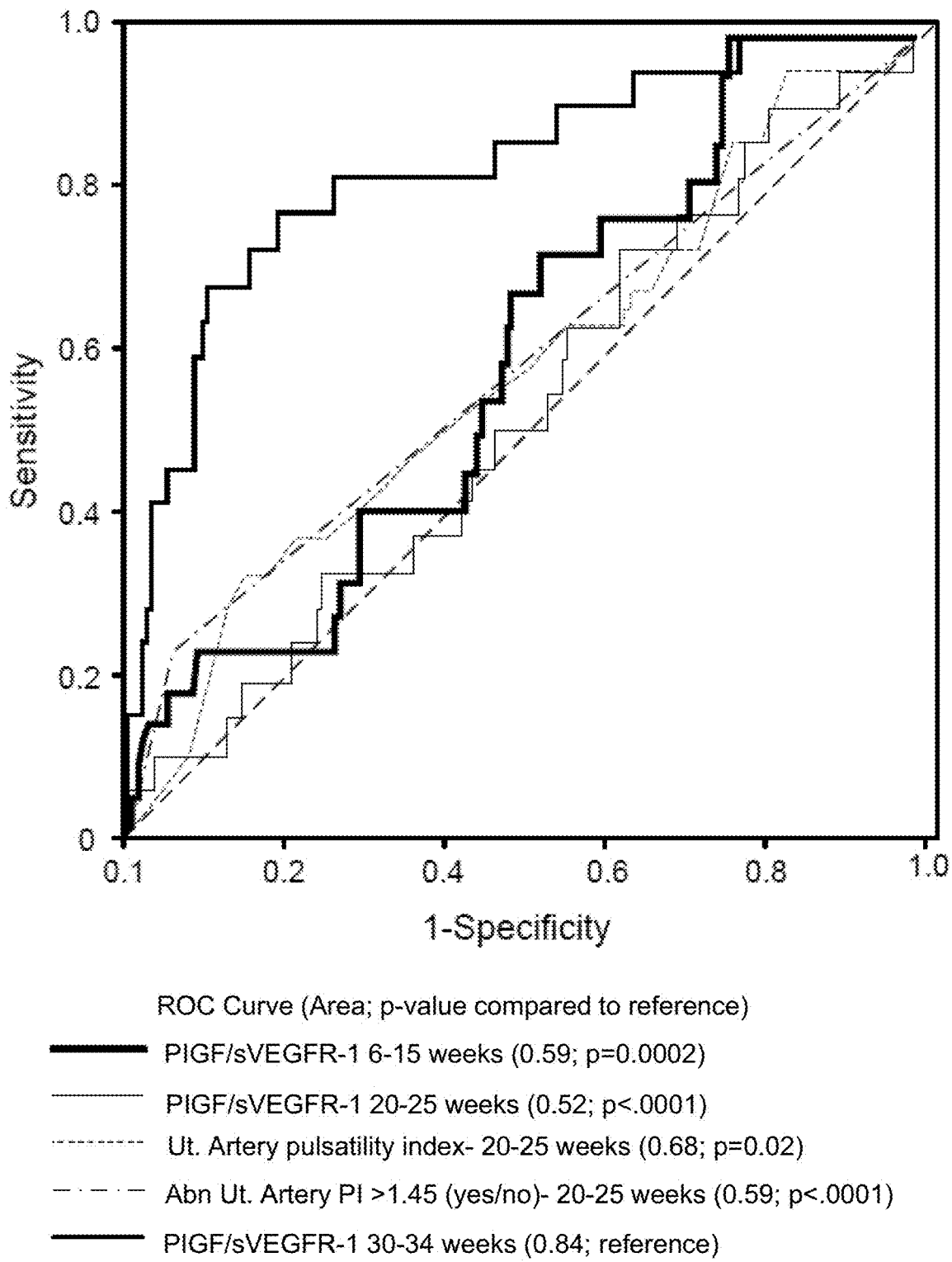

The addition of the PlGF/sEng or PlGF/sVEGFR-1 ratio to the clinical risk factors increased the AUC from 0.76 to 0.88 and 0.86, respectively, for the prediction of severe late PE (p=0.03 and p=0.06). With a fixed false positive rate of 15%, both the PlGF/sEng ratio and PlGF/sVEGFR-1 ratios achieved a sensitivity of 74% in predicting severe PE. These biomarkers in the third trimester outperformed those obtained previously at 6-15 and 20-25 weeks of gestation, and UADV assessed at 20-25 weeks of gestation for the prediction of severe late PE (each p50.02; FIG. 2). Further, the addition of the PlGF/sVEGFR-1 or the PlGF/sEng ratio measured in the $3^{rd}$ trimester to clinical risk factors (age, BMI, combined parity and history of PE, and tobacco use) yielded significantly greater sensitivity at a fixed false positive rate of 15% compared to a model using the same biomarker ratios measured in the $2^{nd}$ trimester, clinical risk factors, and abnormal UADV obtained at 20-25 weeks of gestation (74% vs. 50%; p=0.008 and p=0.03, respectively). The direction, magnitude and significance of these associations also persisted during sensitivity analyses performed excluding subjects having a history of PE (n=37) based on their elevated a-priori risk in the current pregnancy.

While subjects with plasma PlGF/sVEGFR-1 or PlGF/sEng ratio concentrations<0.3 MoM were more likely to develop SGA without PE (aOR 2-3; Table 2), adding these biomarkers to demographic/perinatal data did not improve the AUC (0.64 vs. 0.62; p=0.2 and p=0.6; respectively). Subgroup analysis focusing on subjects with severe SGA (birthweight<3$^{rd}$ centile; n=23) indicated that the adjusted odds ratio of subjects with PlGF/sVEGFR-1 or PlGF/sEng ratio<0.3 MoM to develop severe SGA ranged from 4.4 to 5.5 (Table 2). However, the addition of these biomarkers to clinical risk factors did not significantly improve the AUC (p>0.05).

Figure 3:
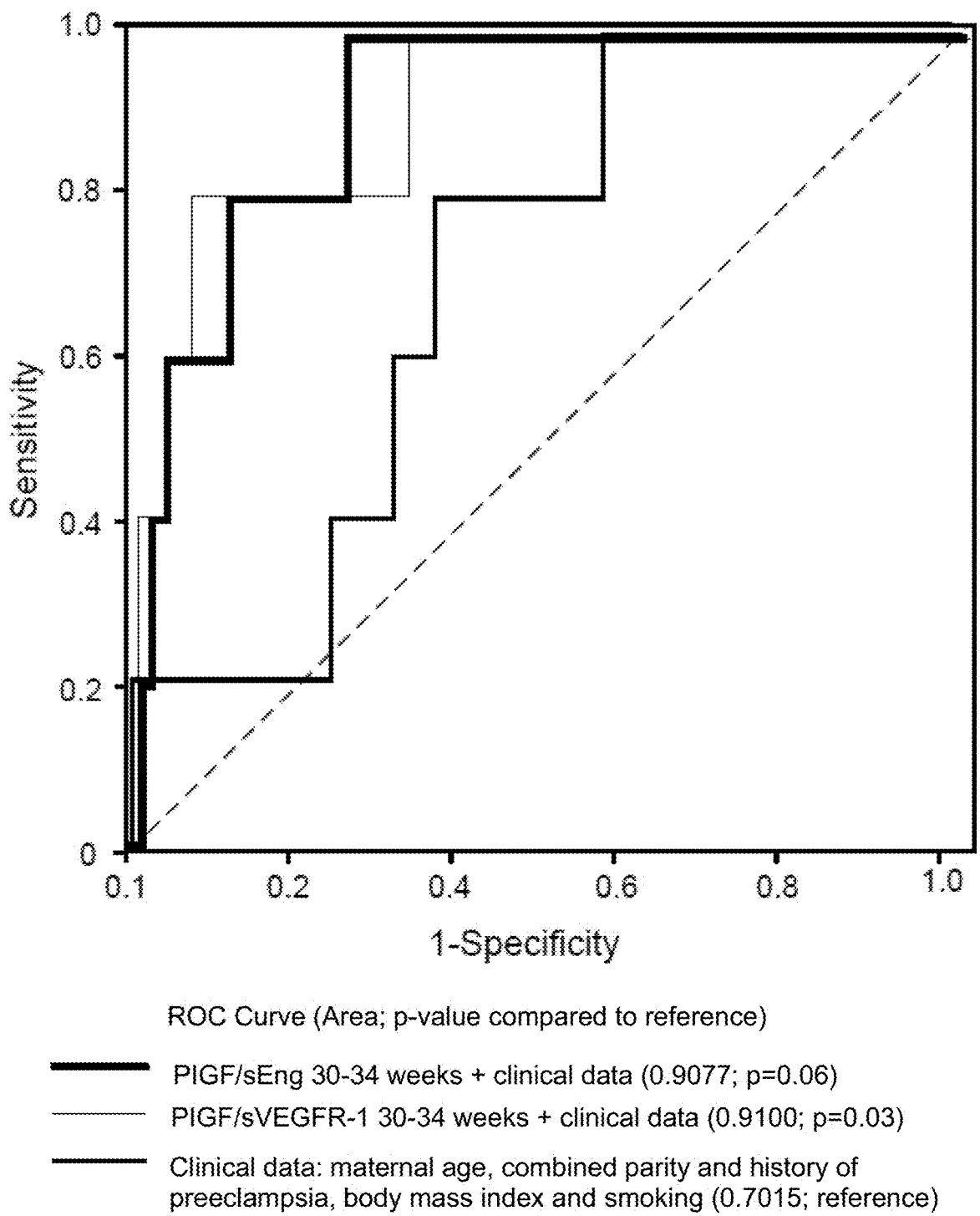
FIG. 3 shows comparisons of ROC curves for the identification of stillbirth using MoM of the ratio of plasma concentrations of PlGF/sVEGFR-1 or PlGF/sEng at 30-34 weeks gestation in addition to clinical data compared to clinical data alone.
Figure 4:
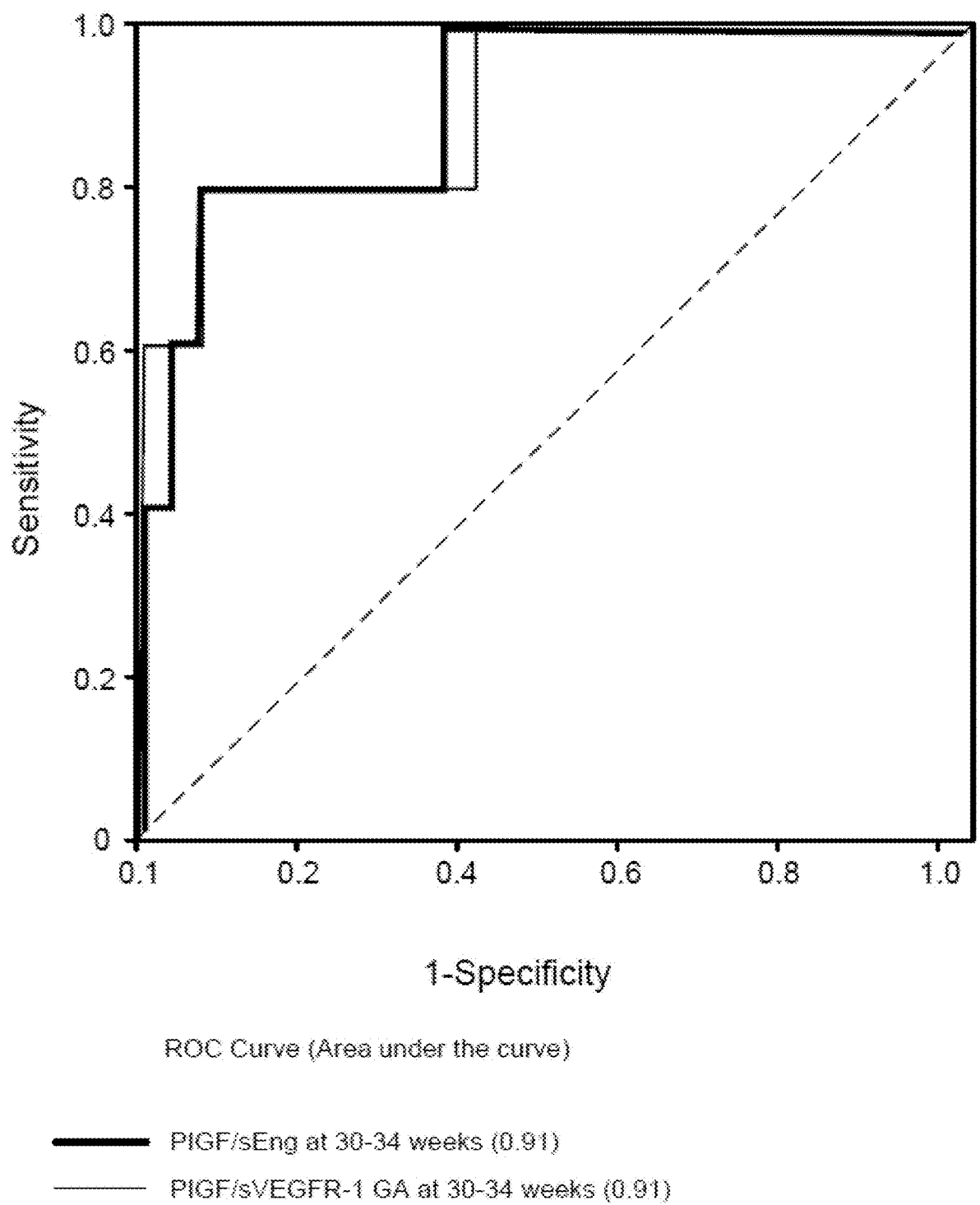
FIG. 4 shows ROC curves for the identification of subsequent stillbirth in case-control study participants using maternal plasma concentrations of PlGF/sVEGFR-1 or PlGF/sEng at 30-34 weeks of gestation. Area under the ROC curves=0.91 for both biomarkers.

Subjects with a PlGF/sVEGFR-1 ratio<0.12 MoM were significantly more likely to have a stillbirth than subjects with a MoM ratio at or above the threshold (aOR 23.1; 95% CI 5.6-95.4). This cut-off had a sensitivity of 80%, specificity of 94%, and a LR of a positive test of 14.2 for the identification of a subsequent stillbirth after 34 weeks of gestation (Table 3). Compared to a model including only clinical data (maternal age, combined parity and history of PE, BMI and tobacco use), addition of the PlGF/sVEGFR-1 ratio or the PlGF/sEng ratio to clinical data increased the AUC from 0.7 to 0.91 (p=0.03 and p=0.06, respectively; FIG. 3). The association between an abnormal ratio of angiogenic/anti-angiogenic factors and stillbirth at or near term was also observed in the subsequent case-control study performed in a different population (Table 4). A maternal plasma concentration of PlGF/sVEGFR-1 ratio≤0.046 or PlGF/sEng ratio≤11.7 µg/ng at 30-34 weeks had a sensitivity of 80% and a specificity of 93% for the identification of subsequent stillbirth (FIG. 4).

TABLE 4

Demographic and obstetrical characteristics of the population in the case-control study

|  | Normal Pregnancies (n = 30) | FD (n = 5) | p |
|---|---|---|---|
| Maternal age (years) | 21.5 (19.8-23.2) | 26 (21.5-36.0) | 0.154 |
| GA at venipuncture (weeks) | 32.9 (32.1-33.6) | 33.4 (32-33.7) | 0.493 |

TABLE 4-continued

Demographic and obstetrical characteristics of the population in the case-control study

|  | Normal Pregnancies (n = 30) | FD (n = 5) | p |
|---|---|---|---|
| Body mass index (Kg/m$^2$) | 26.1 (21.1-35.8) | 24.6 (17.9-44.5) | 0.873 |
| Nulliparity | 53.3%(16) | 60% (3) | 0.585 |
| Tobacco Use | 0 | 0 | — |
| African American | 80% (24) | 80% (4) | 0.90 |
| GA at delivery (weeks) | 39.5 (38.9-40.6) | 37.7 (34.7-38.9) | 0.047 |
| Birthweight (grams) | 3273 (3165-3478) | 2305 (1635-3360) | 0.030 |
| PlGF (pg/ml) | 646 (279-1108) | 97 (63-640) | 0.016 |
| SVEGFR-1 (pg/ml) | 2779 (1822-4349) | 6333 (3740-6908) | 0.016 |
| sEng (ng/ml) | 7.5 (5.7-10.1) | 23.8 (14.4-33.4) | 0.002 |
| PlGF/sVEGFR-1 ratio | 0.25 (0.09-0.5) | 0.02 (0.009-0.1) | 0.002 |
| PlGF/sEng ratio (pg/ng) | 96 (28-167) | 6.9 (2.3-28) | 0.002 |

Value expressed as median (interquartile range) or percentage (number)

Table 5 displays the obstetrical events at delivery, GA at venipuncture, and placental pathology of each subject with stillbirth in the cohort and the case-control study. Among subjects with a stillbirth in the cohort study, the interval from venipuncture to the diagnosis of stillbirth ranged from 2.2 to 6.1 weeks (median 4.5 weeks). One subject was diagnosed to have gestational diabetes mellitus and another had an abruptio placentae. Three subjects had histologic placental lesions consistent with maternal vascular underperfusion according to the criteria of the Society for Pediatric Pathology. Chronic chorioamnionitis and hyalinized avascular villi, consistent with fetal thrombotic vasculopathy, were observed in the other two cases. None of the cases included in the cohort study had a fetal autopsy performed. Of five cases included in the case-control study, two were diagnosed with diabetes mellitus, one was diagnosed with severe PE, one was diagnosed with chronic hypertension and another with Marfan's syndrome. The interval from venipuncture to the diagnosis of stillbirth ranged from 2.4 to 5.4 weeks (median 4 weeks). All four cases of stillbirth included in the case-control study who had a plasma concentration of angiogenic/anti-angiogenic factor ratio below the above cut-off had lesions in the placenta suggestive of maternal vascular underperfusion. Two stillbirths had a karyotype performed and they were 46 XY. Among four cases with available fetal autopsy results, one had lesions in the fetal brain consistent with acute hypoxic/ischemic damage in the grey matter.

TABLE 5

Obstetrical events at delivery, GA at venipuncture, and placental pathology of subjects with stillbirth

| Case | Obstetrical events at delivery | PlGF/SVEGFR-1 ratio (MoM) | GA at venous sampling (weeks) | GA at delivery (weeks) | Birth-weight in grams (%) | Placental lesions consistent with maternal vascular under-perfusion | Placenta pathology | Fetal Autopsy |
|---|---|---|---|---|---|---|---|---|
| Cohort study | | | | | | | | |
| 1 | Normal blood pressure | 0.07 | 32 1/7 | 34 3/7 | 2200 (50%) | Yes | Diffuse chronic villitis, Persistent muscularization of basal plate arteries | Not Available |
| 2 | GDM non-compliance with care | 0.10 | 31 3/7 | 34 4/7 | 2280 (58%) | Yes | Increased syncytial knot | Not Available |
| 3 | Blood pressure 140/90, urine protein dipstick negative, | 0.04 | 31 | 35 4/7 | 3000 (92%) | No | Chronic chorioamnionitis | Not Available |

TABLE 5-continued

Obstetrical events at delivery, GA at venipuncture, and placental pathology of subjects with stillbirth

| Case | Obstetrical events at delivery | PlGF/ sVEGFR-1 ratio (MoM) | GA at venous sampling (weeks) | GA at delivery (weeks) | Birth-weight in grams (%) | Placental lesions consistent with maternal vascular under-perfusion | Placenta pathology | Fetal Autopsy |
|---|---|---|---|---|---|---|---|---|
| | placental abruption | | | | | | | |
| 4 | Normal blood pressure, decreased fetal movement, thick meconium stained amniotic fluid | 0.08 | 33 3/7 | 39 3/7 | 3650 (74%) | Yes | Increased intervillous fibrin, Prominent nucleated RBC, absence of physiologic change of the spiral arteries | Not Available |
| 5 | Normal blood pressure | 0.78 | 32 2/7 | 38 3/7 | 3350 (60.5%) | No | Hyalinized avascular villi, Fetal thrombotic vasculopathy | Not Available |
| | | | | Case-control study | | | | |
| 1 | Gestational diabetes mellitus class A2-poorly controlled glucose | 0.02 | 33 5/7 | 37 5/7 | 3620 (81.5%) | Yes | Microscopic chorionic pseudocysts in placental membranes | No congenital anomalies; No etiology found |
| 2 | Pre-gestational diabetes mellitus class B-poorly controlled glucose | 0.04 | 33 5/7 | 39 1/7 | 3100 (28.1%) | Yes | Recent villous infarction, persistent muscularization of basal plate arteries | Acute hypoxic/ ischemic gray matter damage & Subarachnoid hemorrhage; No congenital anomalies |
| 3 | Severe PE | 0.01 | 31 3/7 | 34 2/7 | 2040 (15%) | Yes | Recent villous infarction | No congenital anomalies; No etiology found |
| 4 | Chronic hypertension | 0.005 | 32 4/7 | 35 | 1231 (1%) | Yes | Remote villous infarction, increased syncytial knots | Not available |
| 5 | Marfan's syndrome | 0.19 | 33 3/7 | 38 4/7 | 2305 (1%) | No | Normal | No congenital anomalies; No etiology found |

GDM = gestational diabetes;

Discussion.

This is the first prospective cohort study evaluating the diagnostic performance of angiogenic/anti-angiogenic factors in the third trimester for the identification of subjects with late PE, severe late PE, SGA without PE and stillbirth. The principal findings are: 1) a maternal plasma concentration of PlGF/sEng<0.3 MoM at 30-34 weeks was associated with late PE (aOR 7) and severe late PE (aOR 16). With a fixed false positive rate of 15%, both the PlGF/sEng and PlGF/sVEGFR-1 ratios achieved a sensitivity of 74% for the identification of severe late PE; 2) the ratio of PlGF/sEng or PlGF/sVEGFR-1 in the third trimester outperformed those obtained at 6-15 and 20-25 weeks of gestation and abnormal UADV obtained at 20-25 weeks of gestation for the identification of severe late PE (comparisons of AUC; each p≤0.02); and 3) a maternal plasma concentration of PlGF/sVEGFR-1 ratio<0.12 MoM at 30-34 weeks was significantly associated with a subsequent stillbirth (aOR 23). This cut-off had a sensitivity of 80%, a specificity of 94%, and a LR of a positive result of 14 for the identification of subjects destined to have a stillbirth; and 4) while a low maternal plasma concentration of the PlGF/sVEGFR-1 and PlGF/Eng ratio was associated with a significant increase in the likelihood of developing SGA, these biomarkers did not improve the identification of SGA from the models using clinical factors alone.

In the described cohort, there was no intra-partum stillbirth case. Among eight stillbirths identified with these biomarkers from the cohort and the case-control studies, seven had lesions in the placenta suggestive of maternal vascular underperfusion. These lesions, although could be observed in 15% of uncomplicated pregnancy at term, have been shown to be more frequently found in PE (relative risk 2-3). Another subject with a stillbirth had chronic chorioamnionitis, a lesion associated with evidence of maternal anti-fetal rejection and FD. Although the precise mechanisms responsible for stillbirth are unknown, the biomarkers investigated in this Example may be able to identify a large fraction of stillbirths resulting from placental rather than non-placental related etiologies (such as cord accident, fetal thrombosis, or feto-maternal hemorrhage). This interpretation is consistent with the findings from a recent study which demonstrated an association between stillbirth at, or near term and UADV in the second trimester, indicating that an increase in impedance to blood flow to the placenta is one of the major risk factors for stillbirth at term. Moreover, because markers of placental dysfunction, such as high maternal serum alpha-fetoprotein or beta human chorionic gonadotropin are associated with an increased risk of unexplained stillbirth and other pregnancy complications such as PE or SGA, it is possible that a subset of unexplained stillbirth, PE, and SGA are different clinical manifestations of a similar placental response from insults at different GAs. Evidence in support of this hypothesis is that rats subjected to reduced utero-placental perfusion by applying clips to the abdominal aorta at different GAs had a different magnitude of change in the angiogenic/anti-angiogenic imbalance, fetal growth restriction and the severity of placental ischemia-induced systemic hypertension.

Example 2. Identification of Late FD with Placental Lesions Suggestive of Maternal Vascular Underperfusion by Assaying Maternal Plasma Concentrations of Angiogenic/Anti-Angiogenic Factors at 24-28 Weeks of Gestation In a prospective cohort study of women with singleton pregnancies, an imbalance of angiogenic and anti-angiogenic factor concentrations at 30-34 weeks of gestation identified 80% of women destined to have a late FD, with a false positive rate of 5%. Similar findings were observed in a parallel case-control study. Seven of the eight FD that were correctly identified as at risk in these two independent study populations had placental lesions suggestive of maternal vascular underperfusion (MVU).

In this Example, whether an imbalance in maternal plasma concentrations of angiogenic/anti-angiogenic factors at 24-28 weeks of gestation can identify women who subsequently had late FD with histopathological evidence consistent with MVU of the placenta was examined.
Methods.
Study Design & Participants. A two-stage case-cohort sampling strategy was used to select participants from among 4,006 women who participated in a longitudinal study to identify biomarkers for several obstetrical complications. These women were enrolled between 6 and 22 weeks of gestation and followed until delivery. Exclusion criteria were multiple gestation, active vaginal bleeding, obstetrical complications, serious medical illness (renal insufficiency, congestive heart disease, and chronic respiratory insufficiency), chronic hypertension requiring medication, asthma requiring systemic steroids, requirement of anti-platelet or non-steroidal anti-inflammatory drugs, active hepatitis, or fetal anomalies identified at enrollment.

In the first sampling stage, 1,000 women were randomly selected from among 2,893 who had venipuncture samples collected in at least three of seven pre-defined GA intervals (8-15.9, 16-19.9, 20-23.9, 24-27.9, 28-31.9, 32-36.9 and ≥37 weeks).

In the second sampling stage, all remaining women who had any of the following diagnoses at delivery were selected from among the 3,006 women who were not selected in the first stage of sampling: PE; PTL; FD; preterm PROM; and delivery of a newborn weighing less than the 5$^{th}$ centile for GA (SGA<5%). The most centrally located venipuncture sample within each of the seven intervals defined by GA for each subject was used for analysis, and in cases of a tie, the first sample obtained was selected.

Data from all subjects selected in the first sampling stage, and from women who had FD in the second sampling stage were used for analysis. All subjects provided written informed consent and the use of clinical data and biological specimens for research purposes was approved by the Institutional Review Board.

Sample Collection and Immunoassays. Blood was obtained by venipuncture and collected into tubes containing EDTA at enrollment and every four weeks until the 24th week of gestation, as well as bi-weekly thereafter until delivery. Samples were centrifuged and stored at −70° C. Maternal plasma concentrations of sVEGFR-1, PlGF, and sEng were determined by immunoassays. The inter- and intra-assay coefficients of variation (CV) of the assays were: 1.4% and 3.9% for sVEGFR-1, 2.3% and 4.6% for sEng, and 6.02% and 4.8%, respectively, for PlGF. The sensitivities of the assays were 16.97 µg/ml for sVEGFR-1, 0.08 ng/ml for sEng, and 9.52 µg/ml for PlGF. Laboratory personnel performing the assays were blinded to the clinical information.

Doppler velocimetry of the umbilical and uterine arteries. Pulse wave and color Doppler ultrasound examinations were performed on the umbilical artery (UA) and both uterine arteries (UtA) using a 3.5- or 5-MHz curvilinear probe. Transducers were directed toward the iliac fossa; the external iliac artery was imaged in a longitudinal section, and the UtA was mapped with color Doppler as it crossed the external iliac artery. Pulsed wave Doppler of both UtAs was performed. After three similar consecutive waveforms were obtained, the PI of the right and left UtA was measured and the mean PI of the two vessels was calculated. The Doppler signal of the UA was obtained from a free-floating loop of the umbilical cord during the absence of fetal breathing and body movement. After three similar consecutive waveforms were obtained, the PI was measured. The inter- and intra-observer CV for UtA Doppler measurement were 11.6% and 5.4%, and for UA, 9.5% and 7%, respectively.

Histological Examination. Placentas were examined histologically according to standardized protocols by perinatal pathologists blinded to clinical diagnoses and obstetrical outcomes. Three to nine sections of the placenta were examined histologically, including at least two full thickness sections of the placental disc, two cord sections, and one membrane roll from the extraplacental membranes. At least one full thickness section was randomly taken from the center of the placenta, others have been taken from the placental margin. Placental lesions consistent with MVU were diagnosed using criteria established by the Perinatal Section of the Society for Pediatric Pathology.

Statistical Analysis. Proportions and 95% CI or medians and interquartile ranges were calculated for categorical and arithmetic variables. Pearson correlation coefficients were used to characterize bivariate relation among arithmetic variables. Quantile regression models were fitted to estimate expected medians of biochemical analyte concentrations and Doppler velocimetry PI as a function of gestational week at examination for women with uncomplicated term pregnancies. MoM were calculated for each biomarker (biochemical and sonographic) for each subject.

Simple and multivariable logistic regression models were fitted to estimate the risk of FD as a function of biochemical, ultrasonographic and/or clinical factors (age, smoking, nulliparity, and pre-pregnancy BMI). Each observation was weighted by the inverse sampling probability generated by the study design. Prognostic performance metrics were calculated to characterize the ability of each model to discriminate subjects destined to have FD from those who would not have a FD. Sensitivity was estimated at increments of fixed specificity by calculating the survival function of the population with FD at the estimated thresholds for 85%, 90%, and 95% quantiles of the sample population without FD. These thresholds were then used to calculate positive and negative predictive values (PPV and NPV, respectively) and LR+ and LR−, respectively. ROC curves were also constructed and non-parametric paired analyses were performed to test for differences in the AUC. Statistical significance was defined using a 5% threshold for Type I error. Statistical analyses were performed using SAS version 9.3 (Cary, NC, USA).

Results.

Study Participants. This study included 1,018 women which represented the cohort of 4,006 with singleton pregnancies. Table 6 shows the characteristics of women with and without FD. Of the 24 total FD included in this study, six occurred among the 1,000 women selected in the first sampling stage, and the remaining 18 cases were selected into the study during the second stage of sampling. Women who had a FD delivered earlier and had lower median birthweight than those who did not have a FD.

TABLE 6

Characteristics of women with and without FD

| Characteristic | No FD (n = 994) | | | FD (n = 24) | | |
|---|---|---|---|---|---|---|
| | N (%) | LCL | UCL | N (%) | LCL | UCL |
| Maternal age, years (Median, IQR) | 23 | 20-27 | | 22.5 | 20-29.5 | |
| Smoker | 206 (20.8) | 18.3 | 23.4 | 5 (20.8) | 7.1 | 42.2 |
| Nulliparity | 381 (38.7) | 35.3 | 41.5 | 8 (33.3) | 15.6 | 55.3 |
| African Americans | 921 (92.7) | 90.9 | 94 | 23 (95.8) | 78.9 | 99.9 |
| Pre-Pregnancy BMI (Median, IQR) | 26.6 | 22.5-32.5 | | 26.8 | 23.2-33.3 | |
| GA at delivery (Median, IQR) | 39.1 | 37.9-40.1 | | 28.3 | 23-31.5 | |
| Baby Weight | 3172.5 | 2800-3485 | | 924.5 | 493.5-1400 | |

IQR: Interquartile range.
Values are expressed as number (percentage), Lower confidence limit (LCL) and upper confidence limit (UCL) or median (interquartile range).
Missing data are:
Parity, n = 1;
Smoker, n = 2;
BMI, n = 16.

Seven of the 24 FDs (29%) occurred before 24 weeks of gestation, 5 (21%) occurred between 24 and 28 weeks of gestation, and 12 (50%) were diagnosed at or after the 28th week of gestation. Placental lesions consistent with MVU were present in 42% (5/12) of the placentas delivered by women who had a FD prior to 28 weeks of gestation, and in 75% (9/12) of those delivered by women who had a FD at or after 28 weeks of gestation.

The latest interval in which ten or more women had venipuncture samples collected before clinical diagnosis of FD was at 24-28 weeks of gestation. Among the 11 women from whom such samples were collected, 72% (n=8) had histologic evidence suggestive of MVU, of which one additionally had lesions consistent with fetal vascular thrombo-occlusive disease (FVTOD). The median interval from venipuncture to the diagnosis of $FD^{up}$ was two weeks (15.5 days) and ranged from one to more than seven weeks. Of the three subjects who subsequently had late FD without histologic lesions consistent with MVU, one had lesions consistent with FVTOD, another had small intervillous thrombi with focal acute chorionitis in the extraplacental membranes, and the remaining subject had focal decidual hemorrhage with acute subchorionitis. All of these cases were antepartum FDs.

Predictive performance at 24-28 weeks of gestation. The sensitivities of plasma angiogenic and anti-angiogenic factor concentrations measured at 24-28 weeks of gestation, in identifying subjects who subsequently had a FD with placental lesions consistent with maternal vascular underperfusion ($FD^{up}$), for different false positive values, is shown in Table 7. For example, at a false positive rate of 10%, the proportions of the subsequent of $FD^{up}$ predicted by the PlGF/sVEGFR1 ratio, the PlGF/sEng ratio, and the sEng were 87.5%, 87.5%, and 75%, respectively. The NPV was greater than 99% for each of the biomarkers studied at each of the three fixed false positive rates at which it was evaluated (5%, 10%, and 15%), in part, reflecting Filed on May 10, 2023 the low prevalence of $FD^{up}$. Among the women who had false positive PlGF/sVEGFR-1 or PlGF/sEng ratios at specificities of 90% or 95%, 49%-61% were diagnosed with PE (25%-45%), SGA (26%-36%), PTL (2%-7%) and/or preterm PROM (0%-4%).

TABLE 7

Prognostic performance of MoM maternal plasma pro-and anti-angiogenic factor concentrations determined at 24-<28 weeks of gestation for the identification of IUFD with evidence suggestive of placental underperfusion

| Biomarker MoM | Subsequent IUFD with evidence of placental underperfusion (n = 8) | | | | | | | | | | | | | | | |
|---|---|---|---|---|---|---|---|---|---|---|---|---|---|---|---|---|
| Fixed Specificity | MoM Cutoff | Se. | LCL | UCL | PPV | LCL | UCL | NPV | LCL | UCL | LR+ | LCL | UCL | LR− | LCL | UCL |
| SVEGFR-1 | | | | | | | | | | | | | | | | |
| 85 | 1.774 | 75 | 35 | 97 | 5 | 2 | 10 | 99.7 | 99.0 | 100 | 5.0 | 3.2 | 7.7 | 0.3 | 0.1 | 1.0 |
| 90 | 2.015 | 75 | 35 | 97 | 7 | 2 | 14 | 99.7 | 99.0 | 100 | 7.4 | 4.7 | 11.6 | 0.3 | 0.1 | 0.9 |
| 95 | 2.631 | 50 | 16 | 84 | 9 | 2 | 21 | 99.5 | 98.7 | 99.9 | 9.9 | 4.7 | 21.0 | 0.5 | 0.3 | 1.1 |
| sEng | | | | | | | | | | | | | | | | |
| 85 | 1.231 | 75 | 35 | 97 | 5 | 2 | 10 | 99.7 | 99.0 | 100 | 5.0 | 3.2 | 7.7 | 0.3 | 0.1 | 1.0 |
| 90 | 1.31 | 75 | 35 | 97 | 7 | 3 | 14 | 99.7 | 99.0 | 100 | 7.5 | 4.8 | 11.8 | 0.3 | 0.1 | 0.9 |
| 95 | 1.55 | 75 | 35 | 97 | 13 | 5 | 26 | 99.8 | 99.1 | 100 | 15.2 | 9.2 | 25.1 | 0.3 | 0.1 | 0.9 |

TABLE 7-continued

Prognostic performance of MoM maternal plasma pro-and anti-angiogenic factor concentrations determined at 24-<28 weeks of gestation for the identification of IUFD with evidence suggestive of placental underperfusion

| Biomarker MoM | | Subsequent IUFD with evidence of placental underperfusion (n = 8) | | | | | | | | | | | | | | |
|---|---|---|---|---|---|---|---|---|---|---|---|---|---|---|---|---|
| Fixed Specificity | MoM Cutoff | Se. | LCL | UCL | PPV | LCL | UCL | NPV | LCL | UCL | LR+ | LCL | UCL | LR− | LCL | UCL |
| PLGF | | | | | | | | | | | | | | | | |
| 85 | 0.388 | 87.5 | 47 | 100 | 5 | 2 | 11 | 99.9 | 99.2 | 100 | 5.8 | 4.3 | 7.9 | 0.1 | 0.02 | 0.9 |
| 90 | 0.319 | 62.5 | 25 | 92 | 6 | 2 | 13 | 99.6 | 98.8 | 99.9 | 6.2 | 3.5 | 11.0 | 0.4 | 0.2 | 1.0 |
| 95 | 0.25 | 62.5 | 25 | 92 | 11 | 4 | 23 | 99.6 | 98.9 | 99.9 | 12.4 | 6.7 | 22.8 | 0.4 | 0.2 | 1.0 |
| PLGF/SVEGFR-1 | | | | | | | | | | | | | | | | |
| 85 | 0.375 | 87.5 | 47 | 100 | 5 | 2 | 11 | 99.9 | 99.2 | 100 | 5.8 | 4.3 | 7.9 | 0.1 | 0.02 | 0.9 |
| 90 | 0.326 | 87.5 | 47 | 100 | 8 | 3 | 15 | 99.9 | 99.3 | 100 | 8.7 | 6.2 | 12.1 | 0.1 | 0.02 | 0.9 |
| 95 | 0.196 | 75 | 25 | 92 | 13 | 5 | 26 | 99.8 | 99.1 | 100 | 15.2 | 9.2 | 25.1 | 0.3 | 0.1 | 0.9 |
| PLGF/sEng | | | | | | | | | | | | | | | | |
| 85 | 0.3989 | 87.5 | 47 | 100 | 5 | 2 | 11 | 99.9 | 99.2 | 100 | 5.8 | 4.3 | 7.9 | 0.1 | 0.02 | 0.9 |
| 90 | 0.336 | 75 | 35 | 97 | 7 | 2 | 14 | 99.7 | 99.0 | 100 | 7.4 | 4.7 | 11.6 | 0.3 | 0.1 | 0.9 |
| 95 | 0.25 | 75 | 35 | 97 | 13 | 5 | 25 | 99.8 | 99.1 | 100 | 14.9 | 9.0 | 24.4 | 0.3 | 0.1 | 0.9 |

Note.
Se., sensitivity; Venipuncture samples were collected for 840 women during this interval.

For the cut off at a 10% false positive rate, the positive LR of these biomarkers for the identification of $FD^{up}$ ranged from 6.2 for PIGF to 8.7 for PIGF/sVEGFR-1. At a cut off at a 5% false positive rate, the positive LR ranged from 9.9 for sVEGFR-1 to 15.2 for PIGF/sVEGFR-1 (Table 7).

Figure 6A:
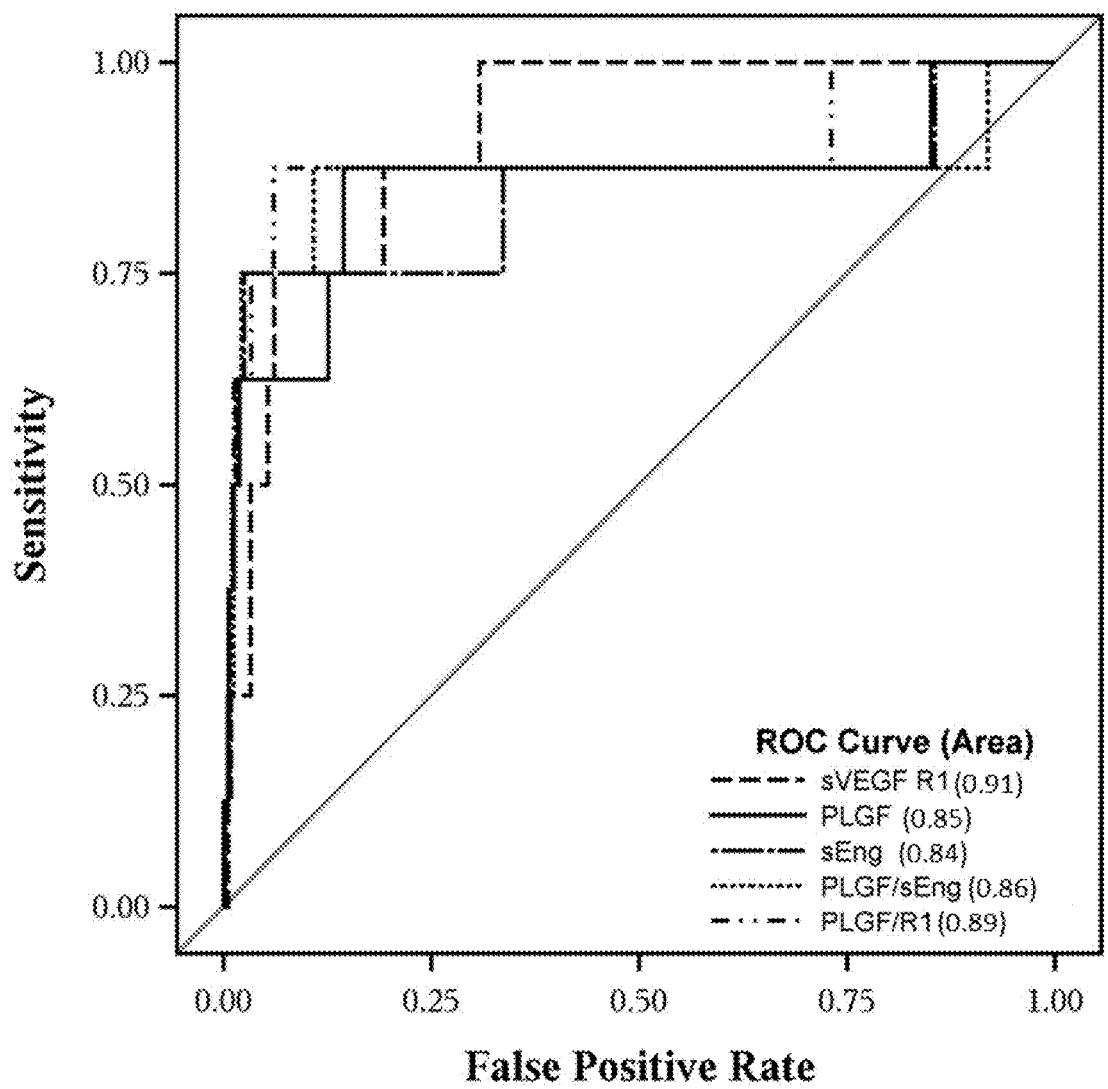
FIGS. 6A-6C show ROC curves for the identification of fetal death (FD) with placental lesions consistent with maternal vascular underperfusion ($FD^{up}$) after 28 weeks of gestation.

The ROC curves for each angiogenic and anti-angiogenic factor and the two concentration ratios, PIGF/sVEGFR-1 MoM or PIGF/sEng MoM, for the identification of women who subsequently had a $FD^{up}$ is shown in FIG. 6A. The ROC curves for the two biochemical marker ratios contrasted with the ROC curve for a combination of selected clinical factors (age, smoking, nulliparity, BMI) and, separately, against UtA PI and UaA PI in FIGS. 6B and 6C, respectively.

Figure 6B:
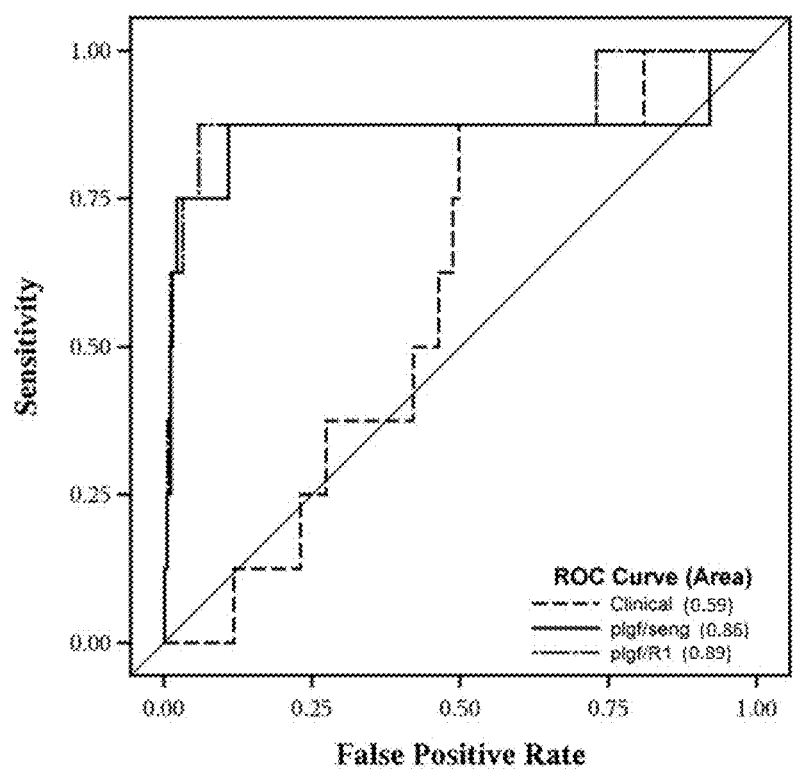
Figure 6C:
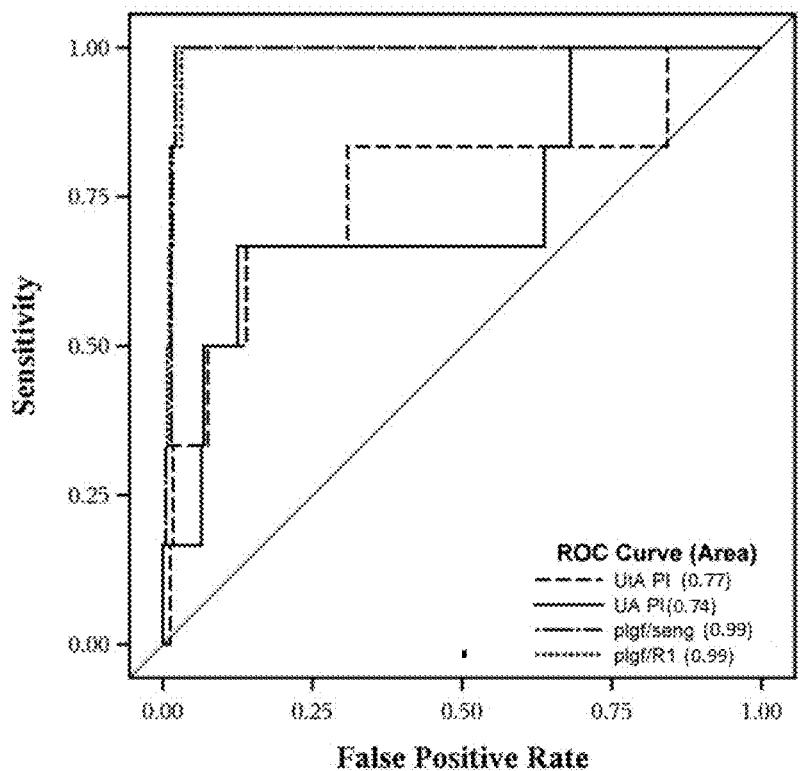

The AUC was between 0.84 and 0.91 for each of the three angiogenic and anti-angiogenic factors and the two angiogenic/anti-angiogenic factor ratios studied (FIG. 6A). The AUC for PIGF/sVEGFR-1 (0.89; 95% CI 0.72-1.0) was significantly greater than that of a combination of basic clinical factors (0.59; 95% CI 0.4-0.7; p=0.02; FIG. 6B). Among the 579 subjects who had Doppler velocimetry results at 24-<28 weeks of gestation, the AUC for PIGF/sVEGFR-1 for identifying $FD^{up}$ was 0.99 (95% CI 0.98-1.0), significantly greater than the AUC for UA PI (0.74; 95% CI 0.49-0.99; p=0.04), and marginally greater than the AUC for UtA PI (0.77; 95% CI 0.51-1.0; p=0.06; FIG. 6C).

The AUC was 0.84 and 0.91 for each of the three angiogenic and anti-angiogenic factors and the two angiogenic/anti-angiogenic factor ratios studied. The AUC for PIGF/sVEGFR-1 (0.89; 95% CI 0.72-1.0) was significantly greater than that of a combination of basic clinical factors (0.59; 95% CI 0.4-0.7; p=0.02). Among the 579 subjects who had Doppler velocimetry results at 24-<28 weeks of gestation, the AUC for PIGF/sVEGFR-1 for identifying $FD^{up}$ was 0.99 (95% CI 0.98-1.0), significantly greater than the AUC for UA PI (0.74; 95% CI 0.49-0.99; p=0.04), and marginally greater than the AUC for UtA PI (0.77; 95% CI 0.51-1.0; p=0.08).

FIG. 7 shows the correlations among plasma concentrations of angiogenic and anti-angiogenic factors and UtA and UA PI among the subset of subjects who did (n=8) and did not (n=585) subsequently have a $FD^{up}$ after 28 weeks of gestation. Each correlation was stronger among subjects who subsequently had a $FD^{up}$ than among those who did not. Among women with subsequent $FD^{up}$, plasma concentrations of anti-angiogenic factors (sVEGFR-1 or sEng) had a strong correlation with UA Doppler PI (Pearson correlation coefficient 0.88 and 0.95 respectively), while those of angiogenic factor (PIGF) had a moderate inverse correlation with mean UtA Doppler PI (Pearson correlation coefficient −0.58). However, the ratios of angiogenic/anti-angiogenic factors had a moderate inverse correlation with both mean UtA and UA Doppler PI (for PIGF/sVEGFR-1: Pearson correlation coefficient −0.58 for UtA and −0.47 for UA Doppler PI and for PIGF/sEng: (Pearson correlation coefficient −0.45 and −0.47, respectively).

sEng and PIGF/sVEGFR-1 each had a sensitivity of 73% (95% CI 39%–94%) at a fixed specificity of 85% for the identification of women who subsequently had any FD (i.e., with or without histologic evidence of MVU). The other angiogenic and anti-angiogenic factors studied identified 45%–64% of the women destined to have a FD at fixed false-positive rates of 10%-15%.

Clinical features and placental histological findings of women with $FD^{up}$. Table 8 describes the clinical presentation, plasma concentration of PIGF/sVEGFR-1 ratio MoM, PIGF/sEng ratio MoM and histological findings of the placentas for women who had a $FD^{up}$ and venipuncture between 24 and 28 weeks of gestation. PE was diagnosed in 3 out of 8 subjects who subsequently had $FD^{up}$. The only subject who subsequently had a $FD^{up}$ whose plasma concentrations of angiogenic and anti-angiogenic factors were above the cutoffs also had histological evidence of FVTOD, which may be a more proximal antecedent than MVU in this case.

TABLE 8

Clinical courses, histological findings and autopsy for subjects who had FD with placental lesions consistent with maternal vascular underperfusion and had venipuncture between 24 and 28 weeks of gestation

| Case | Maternal characteristics Current obstetrics history, Obstetrics events at delivery | PE | GA at Blood Draw (weeks) | PlGF/ SVEG FR-1 (MoM) | PlGF/ sEng (MoM) | GA at diagnosis (weeks) | BW in grams (percentile) | Placental lesions (maternal vascular under-perfusion) | Other placental lesions | Autopsy |
|---|---|---|---|---|---|---|---|---|---|---|
| 1 | 20 y/o, G2P0010 Presented with severe abdominal pain and decreased fetal movement BP 142/98 mmHg, urine protein: negative | No | $24^{+5}$ | 0.037 | 0.057 | $29^{+3}$ | 1270 (39.4) | Yes (placental infarct, acute atherosis of basal plate arteries, decidua basalis blood vessels with absence of physiologic remodeling, focal sclerotic avascular villi arterioles) | Focal acute subchorionitis, separate blood clot consistent with clinical history of placental abruption | N/A |
| 2 | 21 y/o G1P0 Normotensive | No | $25^{+6}$ | 0.152 | 0.132 | $32^{+4}$ | 1530 (12) | Yes (increased intervillous fibrin) | | Stillborn premature fetus, maceration and visceral autolysis, no congenital anomaly |
| 3 | 41 y/o, G8P6107 Chronic hypertension with SPE, placental previa, IUGR ($<5^{th}$ percentile) and abnormal UA Doppler velocimetry, karyotype 46, XX | Yes | 26 | 0.003 | 0.002 | 28 | 530 (2.3) | Yes (remote villous infarct, increased syncytial knots, acute atherosis of basal plate arteries and/or decidual arterioles) | Velamentous insertion of umbilical cord | Stillborn premature fetus with IUGR, CNS: microscopic immature heterotopia at leptomeninges and cerebellum, lymphocyte depletion in thymus and spleen, visceral congestion and intraparenchymal hemorrhage |
| 4 | 33 y/o G9P1162 BP 169/109 mmHg, urine protein 3+ | Yes | $26^{+4}$ | 0.061 | 0.030 | $34^{+3}$ | 2040 (15) | Yes (multiple placental infarction) | Focal depression of maternal surface, decidual hemorrhage, and separate blood clot, consistent with placental abruption, chronic deciduitis with plasma cells | Stillborn premature fetus, no congenital anomaly |
| 5 | 19 y/o G2P0100 Normotensive | No | $26^{+6}$ | 0.232 | 0.349 | $28^{+3}$ | 930 (23.3) | Yes (increased intervillous fibrin) | Overcoiled cord | Stillborn premature fetus, narrowing of the umbilical cord at the fetal insertion |
| 6 | 20 y/o, G2P0101 Vaginal bleeding and contraction BP 148/108 mmHg, urine protein: negative | No | 27 | 0.012 | 0.014 | $28^{+4}$ | 919 (22.2) | Yes (increased syncytial knots, increased intervillous fibrin) | Acute inflammation, and organizing thrombi. Acute subchorionitis, small subchorionic thrombus FVTOD | Stillborn premature male fetus, CNS: grade II germinal matrix hemorrhage, focal petechial hemorrhage in internal capsule, bilateral postaxial polydactyly in upper extremities, |

TABLE 8-continued

Clinical courses, histological findings and autopsy for subjects who had FD with placental lesions consistent with maternal vascular underperfusion and had venipuncture between 24 and 28 weeks of gestation

| Case | Maternal characteristics Current obstetrics history, Obstetrics events at delivery | PE | GA at Blood Draw (weeks) | PIGF/ SVEG FR-1 (MoM) | PIGF/ sEng (MoM) | GA at diagnosis (weeks) | BW in grams (percentile) | Placental lesions (maternal vascular under-perfusion) | Other placental lesions | Autopsy |
|---|---|---|---|---|---|---|---|---|---|---|
| 7 | 30 y/o G6P3113 Chronic hypertension with SPE, BP 162/95 mmHg, urine protein 24 hours 875 mg | Yes | $27^{+4}$ | 0.023 | 0.029 | $30^{+1}$ | 1120 (12.5) | Yes (extensive recent villous infarct, increased syncytial knots, villous agglutination, distal villous hypoplasia, atherosis) | Chronic decuduitis without plasma cells, acute chrorioamnionitis, retroplacental hematoma with depression of the placenta consistent with placental abruption | maceration and severe visceral autolysis N/A |
| 8 | 20 y/o G3P1011 Normotensive | No | $27^{+5}$ | 1.274 | 2.169 | $29^{+4}$ | 1260 (38.6) | Yes (increased intervillous fibrin) | FVTOD | Stillborn premature male fetus, severe maceration and visceral autolysis |

BW: birthweight; y/o: years old; BP: blood pressure; SPE: superimposed PE; IUGR: intrauterine growth restriction; CNS: central nervous system; N/A: Not available Discussion.

At 24–28 weeks of gestation, the sensitivity for a ratio of maternal plasma concentrations of angiogenic and anti-angiogenic factors (PIGF/sVEGFR-1 ratio MoM) in identifying subjects who subsequently had a $FD^{up}$ was 88% at a fixed false-positive rate of 10%, 45%–64% of women who did not have a $FD^{up}$ but who had abnormal risk scores, were diagnosed with PE, SGA, PTL and/or preterm PROM. Plasma angiogenic and anti-angiogenic factor concentrations MoM correlated more strongly with UtA and UA PI at 24–28 weeks of gestation in women who subsequently had a $FD^{up}$ than among those who did not. These findings support the view that the majority of women destined to have a late FD accompanied by histopathological evidence suggestive of MVU can be identified with a false positive rate of 10% or less, using maternal plasma concentrations of angiogenic and anti-angiogenic factors measured at 24-<28 weeks of gestation.

Risk assessment and prevention of FD have been neglected areas of prenatal care. This is partly attributable to the complexity of this disease, which does not often have a single cause, and multiple factors are implicated in its pathogenesis in most cases. A substantial fraction of FDs are preceded or accompanied by evidence suggestive of placental underperfusion and/or dysfunction, including: 1) increased impedance to uteroplacental blood flow as determined by abnormal UtA Doppler velocimetry in the first or second trimester; 2) low pregnancy-associated plasma protein (PAPP)-A measured in the first trimester or high maternal serum alpha-fetoprotein or human chorionic gonadotropin measured in the second trimester of pregnancy); and 3) histopathological placental lesions consistent with MVU. Maternal plasma angiogenic and anti-angiogenic factor concentrations measured at 30-34 weeks of gestation identified 80% of subsequent late FDs. Moreover, nearly all (n=8/10) of the correctly identified cases had placental lesions consistent with MVU. We accordingly hypothesized that the studied biochemical markers could identify the majority of late FDs, presumably those attributable to placental dysfunction, apart from FDs resulting more so from other pathways (e.g., cord accidents).

An imbalance in angiogenic/anti-angiogenic factor concentrations measured in maternal plasma at 24-28 weeks of gestation correctly identified all but a single case of late $FD^{up}$ with a false positive rate of only 10%. Moreover, the single case that was not correctly identified by the test additionally had placental lesions consistent with FVTOD and, thus, may have resulted from factors unrelated to placental dysfunction associated with MVU. The majority of women with positive tests who did not have $FD^{up}$ had other obstetrical syndromes previously associated with an imbalance in angiogenic and anti-angiogenic factors, including PE, SGA offspring, and PTL.

Each correlation between plasma concentration of either angiogenic or anti-angiogenic factors and mean UtA or UA Doppler PI was stronger among subjects who subsequently had a $FD^{up}$ than among those who did not (FIG. 7). A reduction in uteroplacental blood flow or an abnormality in the placental villous tree has been implicated in the pathogenesis of FD. The finding of a significant relationship between Doppler PI in the uterine or umbilical circulations and plasma concentrations of angiogenic or anti-angiogenic factors, respectively, adds further evidence to support this view. However, the ratios between angiogenic and anti-angiogenic factors had only modest correlation with either mean UtA or UA Doppler PI. This may explain why plasma concentrations of the ratios of angiogenic/anti-angiogenic factors performed better than UtA or UA Doppler PI in the identification of subsequent $FD^{up}$.

Collectively, our findings indicate that, because of their high sensitivities at a fixed false positive rate of 10%, the studied biomarkers could be used to perform risk assessment for late FD$^{up}$. Indeed, it seems that our predictive strategy could be used to reduce the number of subjects considered to be at-risk during the late second trimester by 90% (e.g., with the 10$^{th}$ percentile cut-off, from 4,000 down to 400).

Using a simple blood test performed at 24-28 weeks of gestation to measure maternal plasma concentrations of angiogenic and anti-angiogenic factors, risk assessment for late FD with placental lesions consistent with MVU is possible.

Figure 5A:
FIG. 5A and FIG. 5B show a histopathological examination of the placenta from a previous pregnancy showed fibrinoid deposition (arrow) in the intervillous space surrounding more than 50% of the villi in some full thickness sections (H&E; ×40) (FIG. 5A) and absence of physiologic transformation of a spiral artery, i.e. persistent muscularization (circle) in the basal plate (H&E, ×100) (FIG. 5B).
Figure 5B:
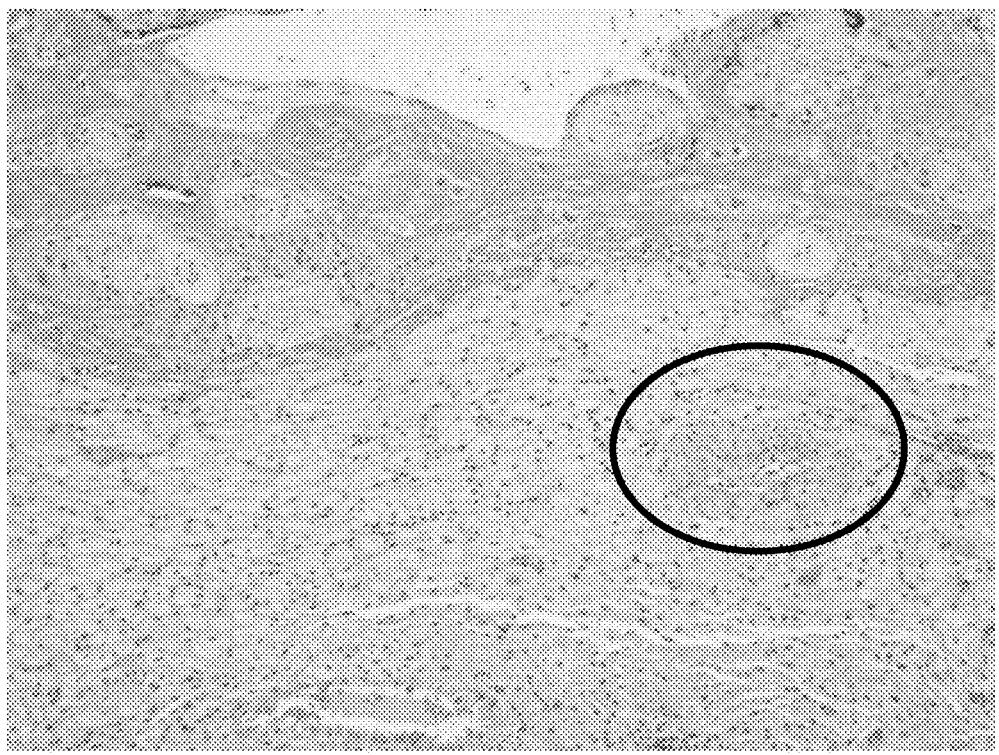

Example 3. Early Identification of an Angiogenic and Anti-Angiogenic Imbalance and Treatment with Pravastatin Prevents Recurrent FD A 38-year old woman with a history of four early pregnancy loses, presented for consultation at 15 weeks and 4 days of gestation. Her first and third pregnancies ended in spontaneous abortion between 9 and 10 weeks of gestation. Her second pregnancy was complicated by anhydramnios, placental abnormalities, elevated alpha feto-protein (AFP) (4.7 MoM), and fetal demise at 18 weeks of gestation. Acetylcholine esterase at 18 weeks was normal as was the fetal karyotype (46XX). The fourth pregnancy was terminated at 19 weeks of gestation, and the placenta showed marked fibrin deposition in a sub-chorionic location and the intervillous space. Due to the history of the three consecutive pregnancy losses, the subject was started on aspirin (81 mcg) preconceptionally and heparin (7500 ml twice per week) at five weeks, which continued during her fourth pregnancy. Vaginal progesterone suppositories were administered starting at eight weeks of gestation. Pregnancy-associated plasma protein-A (PAPP-A) concentration was low (0.1 percentile) at 12 weeks, and maternal serum AFP was elevated (9.26 MoM) in the second trimester. Ultrasound examination at 16 weeks gestation revealed thickened placenta with numerous large placental lakes. The subject had a fetal demise at 20 weeks of gestation associated with anhydramnios and severe early-onset fetal growth restriction, which was treated by dilation and evacuation. Fetal autopsy revealed bilateral club feet without other anatomical anomalies. Cytogenetic study of the fetal skin and placenta showed a normal karyotype. Histopathologic examination of the placenta revealed MPFD or MFI, and failure of physiologic transformation in the decidual segment of the spiral arteries (FIGS. 5A and 5B).

In this Example, maternal plasma concentrations of sVEGFR-1 were above the 95th percentile from 13 weeks of gestation. This is consistent with previous observation that early elevation of sVEGFR-1 in the second trimester, especially from 14-16 weeks of gestation, without a change in PlGF appears to be suggestive of MFI.

Thrombophilia workup for protein C deficiency, protein S deficiency, homocysteinemia, antithrombin III deficiency, prothrombin gene mutations, factor V Leiden mutation, and antiphospholipid syndrome (anti-cardiolipin antibodies and lupus anti-coagulant) were all negative. The paternal genotype analysis revealed the presence of HLA-A25 antigen, and an antibody to this antigen was present in maternal serum. The subject had been receiving aspirin and heparin, and was given intravenous immunoglobulin (IVIG).

The subject received subcutaneous 5000 units of heparin twice a day, 81 mg aspirin tablet daily, and IVIG 1 mg/kg every four weeks from the beginning of the current pregnancy. At 12 weeks and 2 days gestation, maternal PAPP-A concentration was low (1st percentile). At 15 weeks and 4 days ultrasound evaluation showed normal fetal anatomy with appropriate fetal growth (66th percentile). However, bilateral UtA notching (mean UtA PI 2.23 (95th percentile)) was noted, and the plasma angiogenic/anti-angiogenic factor ratio concentrations were low. See FIG. 8A-8D. At 13, 15, and 17 weeks of gestation, plasma concentrations of sVEGFR-1 and sEng were extremely high (96th-98th percentile; see Table 9 and FIGS. 8A and 8C)), and those of PlGF were within normal limits (59th-62nd percentile; Table 9, FIG. 8B). The PlGF/sVEGFR-1 concentration ratios were low, in the 4th, 6th, and 10th percentiles, respectively (see FIG. 8D).

TABLE 9

Plasma concentrations (percentile for GA) of angiogenic and anti-angiogenic factors

| GA (weeks + days) | SVEGFR-1 (pg/mL) (percentile) | PlGF (pg/mL) (percentile) | sEng (ng/mL) (percentile) | PlGF/ SVEGFR-1 (percentile) |
|---|---|---|---|---|
| 13 + 3 | 5664 (98) | 60 (59) | 9.8 (96) | 0.01 (4) |
| 15 + 4 | 4897 (98) | 100 (60) | 11.8 (98) | 0.02 (6) |
| 17 + 4 | 4480 (96) | 157 (62) | 11.3 (98) | 0.03 (10) |
| 19 + 5 | 4148 (93) | 306 (76) | 13.1 (98) | 0.07 (23) |
| 21 + 6 | 1889 (56) | 644 (93) | 8.7 (94) | 0.34 (90) |
| 25 + 3 | 2854 (80) | 768 (79) | 8.8 (94) | 0.27 (51) |
| 27 + 4 | 3881 (90) | 869 (74) | 9.9 (95) | 0.22 (34) |
| 29 + 4 | 4684 (93) | 821 (65) | 12.7 (97) | 0.18 (25) |
| 31 + 4 | 6370 (97) | 536 (44) | 9.6 (85) | 0.08 (10) |
| 33 + 5 | 11202 (99) | 528 (46) | 12.7 (85) | 0.04 (6) |

Percentile distribution was based on a published reference range (Whitten et al., Am J Obstet Gynecol. 208: 310 e311-310 e311, 2013).

FIGS. 8A-8D show the maternal plasma concentrations. (log base e) of sVEGFR-1 (FIG. 8A), PlGF (FIG. 8B), sEng (FIG. 8C), and the ratio of PlGF/sVEGFR-1 (FIG. 8D) throughout pregnancy in the case report, plotted against reference ranges at 2.5th 5th, 10th, 50th, 90th, 95th, and 97.5th percentile of uncomplicated pregnancies.

The subject was informed of these findings, of the poor prognosis associated with extremely high plasma sVEGFR-1 concentrations, and of the likelihood that this pregnancy, like her previous one, could be affected by MF. After being counseled extensively about the potential adverse events and issues of safety of pravastatin administration during pregnancy, and informed that there was little evidence from animal experiments that pravastatin could reverse angiogenic/anti-angiogenic factor imbalances, the subject was offered and opted to receive pravastatin 20 milligrams once daily at 17 weeks and 4 days of gestation. At 21 weeks of gestation, the plasma concentrations of sVEGFR-1 decreased to the normal range (56th percentile) while that of PlGF increased to 93rd percentile. Plasma sEng remained high, at the 94th percentile.

Ultrasonographic evaluation at 24 weeks of gestation revealed an appropriate fetal weight for GA (66th percentile). Plasma concentrations of sVEGFR-1 increased from 80th percentile at 25 weeks to 99th percentile at 33 weeks of gestation, whereas those of PlGF decreased from 79th percentile at 25 weeks to 46th percentile at 33 weeks. During this period, the plasma concentrations of sEng remained unchanged and were at 85th-94th percentile.

The subject developed preterm pre-labor rupture of membranes and was induced at 34 weeks of gestation. A male neonate weighing 2220 grams, APGAR scores 8 and 8 at 1 and 5 minutes, respectively, was delivered vaginally. The neonate was discharged home without major complications in 7 days. His weight, height, and developmental milestones at age two are normal.

Histopathological examination of the placenta revealed fibrinoid deposition in the intervillous space (20%), distal villous hypoplasia (consistent with MVU) and persistent muscularization of the spiral arteries in the basal plate (FIGS. 9A-9D).

Discussion.

The subject took heparin, aspirin, and IVIG from the first trimester of the current pregnancy, yet still had abnormal plasma concentrations of PAPP-A (1st percentile) and sVEGFR-1 (above the 95th percentiles), suggesting that these interventions may not have been effective in reversing the pathologic process. Evidence from meta-analysis and the most recent randomized controlled trial concluded that there is no significant benefit from IVIG in subjects with recurrent miscarriages. The beneficial effects of IVIG in preventing recurrent pregnancy loss, like those of heparin and aspirin, appear to be confined to subjects who have evidence of antiphospholipid syndrome or increased NK cell activity.

In the present case, maternal plasma concentrations of sVEGFR-1 were above the 95th percentile starting at 13 weeks of gestation. This observation was consistent with previous findings that an early elevation of sVEGFR-1 in the second trimester, especially from 14-16 weeks of gestation, without a change in PlGF, appears to be suggestive of MFI. The plasma concentrations of sEng were above the 95th percentile from 13 weeks of gestation. The concomitant elevation of sVEGFR-1 and sEng suggest a serious derangement.

The subject described in this Example decided to take pravastatin after extensive counseling about potential benefits, side effects, and the possibility of unknown effects on the fetus. After taking pravastatin for 2 weeks, plasma concentrations of sVEGFR-1 started to decrease from the 96th percentile to the 93rd percentile, and further decreased to the 56th percentile after 4 weeks of treatment. In contrast, plasma concentrations of PlGF started to increase from the 62nd percentile to 76th percentile after 2 weeks, and rose to the 93rd percentile after 4 weeks of treatment. The subject continued taking pravastatin, yet, plasma sVEGFR-1 concentrations became abnormal again in the third trimester, probably due to increase in the size of the placenta, which is a major source of this anti-angiogenic proteins.

Pravastatin treatment has been shown to reduce plasma concentrations of sEng and placental mRNA expression of transforming growth factor-03 in animal experiments. Yet, plasma sEng concentrations in the instant case remained high throughout pregnancy.

These findings suggest that pravastatin can reverse an angiogenic and anti-angiogenic imbalance without correcting the underlying cause of the disease because the subject's placenta had pathological findings similar, but less severe, to those found in her previous pregnancy that ended in fetal demise. It appears that pravastatin acts more distally along the pathophysiological chain that culminates in fetal demise to reverse the angiogenic and anti-angiogenic imbalance, and prevent fetal demise or delay the need for delivery until viability.

Example 4

This retrospective longitudinal case-control study included MPFD cases (n=10) and control subjects (n=175) with uncomplicated pregnancies who were enrolled in a longitudinal study and delivered at term. Serial plasma concentrations of PlGF, sEng, and sVEGFR-1 and -2 were determined by ELISA (cases, n=28 samples; controls, n=751 samples). Individual analyte concentrations were averaged across gestational length at specimen collection intervals. Linear mixed models were used to test for differences in log transformed mean analyte concentrations both overall and as a function of time.

A longitudinal retrospective case-control study was conducted by reviewing placenta pathology records of subjects from 2006 to 2011. Cases consisted of subjects with placental pathology meeting the diagnostic requirements for MPFD, which was defined as a placenta with perivillous fibrinoid material (either limited to the maternal floor of the placenta or extending from maternal to fetal surfaces) encasing at least 50% of the villi on a minimum of one slide. Controls were women without MPFD in the placenta, who had uncomplicated pregnancies, delivered a term neonate whose birth weight was appropriate for GA (10th-90th percentiles) and had plasma samples available for at least five of the following GA intervals: 6-9.9, 10-14.9, 15-19.9, 20-23.9, 24-27.9, 28-31.9, 32.-36.9, and ≥37 weeks. These subjects were enrolled in a longitudinal protocol to identify biological markers for the prediction of PE, SGA, and stillbirth. Venous samples were collected every four weeks until 24 weeks and every two weeks thereafter until delivery. Exclusion criteria were 1) multiple gestations and 2) congenital fetal anomaly.

All women provided written informed consent before participating in the study and the use of clinical data and collection.

Sample Collection and Immunoassays. Venipuncture was performed serially at regular prenatal visits and admissions to the hospital for all normal and MPFD affected pregnancies. Blood was collected into tubes containing EDTA. Samples were centrifuged and stored at −70° C. until used for assay. Sensitive and specific immunoassays (R&D systems, Minneapolis, MN) were used to determine maternal plasma concentrations of PlGF, sEng, sVEGFR-1 and -2. All immunoassays utilized the quantitative sandwich enzyme immunoassay technique, and their concentrations in maternal plasma were determined by interpolation from the standard curves. The inter- and intra-assay coefficients of variation (CV) obtained in the laboratory were as follows: PlGF, 6.02 and 4.8%, respectively; s-Eng, 2.3 and 4.6%, respectively; sVEGFR-1, 1.4 and 3.9%, respectively; and sVEGFR-2, 2 and 4%, respectively. The sensitivity of the assays was as follows: PlGF, 9.52 µg/mL; s-Eng, 0.08 ng/mL; sVEGFR-1, 16.97 pg/mL; and sVEGFR-2, 19.01 µg/mL.

Statistical Analysis. Demographic and obstetrical characteristics. Comparisons between continuous variables were performed by Mann-Whitney U tests. Proportions were compared using either Fisher exact or Chi-square tests as appropriate. A p-value<0.05 was considered statistically significant. Descriptive analysis was performed using SPSS Version 15.0 (SPSS, Inc., Chicago, IL, USA).

Longitudinal analysis of angiogenic/anti-angiogenic factor concentrations. Individual analyte concentrations (PlGF, sEng, sVEGFR-1, and sVEGFR2) and their ratios (PlGF/sEng and PlGF/sVEGFR-1) were averaged across four intervals defined by gestational length at venipuncture (<14 weeks, 14–16 weeks, 17–19 weeks, and 20–30 weeks). Linear mixed models were used to test for differences in $\log_{10}$ transformed mean analyte concentrations overall and as a function of time using a robust covariance matrix estimator. Covariables included in adjusted models were selected based on clinical knowledge and factors associated with MPFD and/or analyte concentrations. These included GA at venipuncture, BMI, maternal age, African American ethnicity and nulliparity. Model reduction was additionally performed based on the plausibility of regression coefficients, association with independent/dependent variables, magnitude of change in the main effect parameter estimates and model fit as indicated by the Bayesian Information Criteria (BIC). Linear combinations of model parameters comparing differences between cases and controls at each GA interval were used to determine the timing of changes in angiogenic/anti-angiogenic factors. Longitudinal analyses were performed using SAS version 9.3 (SAS Institute, Inc., Cary, NC, USA).

Results.

Clinical Characteristics. During the study period, 10 pregnancies with MPFD and 175 controls were identified. Table 10 describes the clinical and demographic characteristics of the study population. As expected, the median GA at delivery and the median birthweights were lower in the MPFD affected pregnancies than those in uncomplicated pregnancies (each p<0.001; see Table 10). Pregnancy complications in cases with MPFD included miscarriage in the second trimester (n=4), fetal growth restriction (n=4) with abnormal UA Doppler velocimetry (n=3), second and third trimester fetal demise (in-utero: n=5; intrapartum: n=1), and abruptio placentae (n=2). With the exception of one subject who delivered at term, all MPFD cases delivered before 31 weeks of gestation and only two had viable neonates (see Table 11). Three pregnancies have been evaluated for the presence of anticardiolipin antibody and lupus anticoagulant and all of these tests were negative.

TABLE 10

Demographics and clinical characteristics of the study population

|  | Uncomplicated pregnancies (n = 175) | MPFD (n = 10) | p-value |
|---|---|---|---|
| Maternal Age (years) | 23 (20-26) | 31 (26-35) | <0.001 |
| African American | 151 (86%) | 10 (100%) | 0.4 |
| Nulliparity | 63 (35%) | 0 (0%) | 0.03 |
| BMI (kg/m$^2$) | 27 (23-32) | 29 (28-35) | 0.04 |
| GA at Delivery (weeks) | 39 (39-40) | 23 (17-29) | <0.001 |
| Birth weight (grams) | 3330 (3150-3555) | 277 (175-605) | <0.001 |
| Stillbirth (>20 weeks) | 0 | 4 (40%) | — |
| Miscarriage in the Second Trimester (<20 weeks) | 0 | 4 (40%) | — |
| Fetal Growth Restriction | 0 | 4 (40%) | — |
| Placental Abruption | 0 | 2 (20%) | — |

Data are expressed as median (interquartile range) or number (percent).

TABLE 11

Clinical and obstetrical characteristics of subjects with MPFD

| Case No. | Age | Gravida, Parity | GA at delivery (weeks + days) | Clinical Description | Birth Weight (grams, percentile for GA) | Pre-labor Rupture of Membranes | Fetal Growth Restriction | Fetal Demise | Second Trimester Miscarriage |
|---|---|---|---|---|---|---|---|---|---|
| 1 | 24 | G 4 P 2-0-1-2 | 15 + 6 | Presented with ruptured membranes and was induced for inevitable abortion. | 150 | Yes | No | No | Yes |
| 2 | 27 | G 3 P 0-0-2-0 | 30 + 0 | Presented with fetal growth restriction, heavy vaginal bleeding/clinical placental abruption and emergent cesarean delivery was performed. | 755 (1%) | No | Yes | No | No |
| 3 | 22 | G2 P 0-0-1-0 | 22 + 3 | Short cervix was noted at 20 weeks; membranes ruptured with spontaneous labor at 22 weeks and delivery of a stillborn infant. | 448 (34%) | Yes | No | Yes | No |
| 4 | 28 | G 11 P 0-1-9-1 | 23 + 6 | Fetus noted to have thickened placenta, multiple placental lacunae, and oligohydramnios at 18 weeks; abnormal Doppler parameters, fetal demise was diagnosed and the subject was induced | 277 (1%) | No | Yes | Yes | No |
| 5 | 43 | G 13 P 3-3-6-4 | 16 + 4 | Presented with ruptured membranes and fetal demise. | Unknown | Yes | No | Yes | Yes |
| 6 | 35 | G 7 P 0-0-6-0 | 17 + 3 | Cervical length of 0 mm on routine scan; A rescue cerclage was placed but membranes ruptured shortly afterwards. Induction for inevitable abortion. | 160 | Yes | No | No | Yes |
| 7 | 29 | G 3 P 1-1-0-1 | 17 + 2 | Presented with abdominal pain and vaginal bleeding. | 190 | No | No | Yes | Yes |

TABLE 11-continued

Clinical and obstetrical characteristics of subjects with MPFD

| Case No. | Age | Gravida, Parity | GA at delivery (weeks + days) | Clinical Description | Birth Weight (grams, percentile for GA) | Pre-labor Rupture of Membranes | Fetal Growth Restriction | Fetal Demise | Second Trimester Miscarriage |
|---|---|---|---|---|---|---|---|---|---|
| 8 | 35 | G 12 P 8-2-1-8 | 23 + 1 | Fetal demise was diagnosed and the subject was induced. Fetus noted to have decreased growth and progressive deterioration of Doppler parameters starting at 20 weeks gestation. Fetal demise diagnosed at 23 weeks. | 274 (1%) | No | Yes | Yes | No |
| 9 | 34 | G 11 P 8-1-1-8 | 28 + 2 | Fetus noted to have growth restriction and progressive deterioration of Doppler parameters starting at 20 weeks. Fetal demise diagnosed and the subject was induced. | 454 (1%) | No | Yes | Yes | No |
| 10 | 33 | G 10 P 7-1-1-7 | 38 + 1 | Spontaneous labor at term. | 3285 (51.5%) | No | No | No | No |

**Cases #8-10 are pregnancies from the same subject; G = gravida; P = parity

Longitudinal analysis of plasma sVEGFR-1, sVEGFR-2, sEng, and PlGF concentrations. Subjects with MPFD had a significantly lower mean plasma PlGF concentration (p=0.03), but significantly higher mean plasma concentrations of sVEGFR-1 (p<0.01) and sEng (p<0.01) than controls after adjusting for potential confounders (see FIG. 10 and FIG. 11). The mean maternal plasma concentrations of PlGF differed further among subjects who had MPFD and the control group as a function of GA interval (p<0.0001). However, the magnitude of the differences in mean plasma concentrations of sVEGFR-1 and sEng did not change significantly with GA interval (p=0.09, FIG. 10; p=0.11, FIG. 11). There were no significant differences in plasma concentrations of sVEGFR-2 observed overall (p=0.97), or as a function of time (p=0.17) among cases and controls (see FIG. 12).

Subjects with MPFD had significantly lower mean ratio concentrations of PlGF/sVEGFR-1 (p<0.0001) and PlGF/sEng (p<0.001; FIG. 13) after adjustment for potential confounders; both of these relationships differed significantly as a function of GA interval (each p<0.0001; FIG. 13).

As shown in FIG. 10-13, while the differences in mean plasma PlGF concentration among cases and controls became statistically significant at 20-30 weeks of gestation, differences in mean sEng and the ratios of PlGF/sEng and PlGF/sVEGFR-1 among cases and controls became significant from 17-19 weeks of gestation onwards. Consistent changes in the mean plasma sVEGFR-1 concentration in cases compared to controls appear to begin early, at 14-16 weeks gestation. The mean concentration of each angiogenic and anti-angiogenic factor for each GA interval in MPFD subjects and controls are shown in Table 12.

TABLE 12

Mean, standard deviation, median and inter-quartile range plasma analyte concentrations and their ratios by study group and gestational length interval at measurement

| Analyte | Gestational Length Interval | Study Group | $N^2$ | Mean | Std. Dev. | Median | $25^{th}$ centile | $75^{th}$ centile |
|---|---|---|---|---|---|---|---|---|
| PlGF (pg/mL) | I: <14 weeks | Case | 4 | 20 | 7 | 22 | 16 | 24 |
| | | Control | 110 | 40 | 98 | 23 | 16 | 36 |
| | II: 14-16 weeks | Case | 7 | 106 | 45 | 119 | 76 | 152 |
| | | Control | 82 | 106 | 61 | 87 | 59 | 132 |
| | III: 17-19 weeks | Case | 4 | 110 | 63 | 126 | 73 | 148 |
| | | Control | 72 | 201 | 106 | 189 | 125 | 260 |
| | IV: 20-30 weeks | Case | 6 | 125 | 103 | 100 | 43 | 206 |
| | | Control | 172 | 598 | 409 | 516 | 320 | 775 |
| sEng (ng/mL) | I: <14 weeks | Case | 4 | 20 | 7 | 22 | 16 | 24 |
| | | Control | 110 | 40 | 98 | 23 | 16 | 36 |
| | II: 14-16 weeks | Case | 7 | 106 | 45 | 119 | 76 | 152 |
| | | Control | 82 | 106 | 61 | 87 | 59 | 132 |
| | III: 17-19 weeks | Case | 4 | 110 | 63 | 126 | 73 | 148 |
| | | Control | 72 | 201 | 106 | 189 | 125 | 260 |
| | IV: 20-30 weeks | Case | 6 | 125 | 103 | 100 | 43 | 206 |
| | | Control | 172 | 598 | 409 | 516 | 320 | 775 |
| sVEGFR-1 (pg/ml) | I: <14 weeks | Case | 4 | 2200 | 1165 | 2487 | 1510 | 2891 |
| | | Control | 110 | 1697 | 1276 | 1513 | 986 | 1930 |

TABLE 12-continued

Mean, standard deviation, median and inter-quartile range plasma analyte concentrations and their ratios by study group and gestational length interval at measurement

| Analyte | Gestational Length Interval | Study Group | $N^2$ | Mean | Std. Dev. | Median | $25^{th}$ centile | $75^{th}$ centile |
|---|---|---|---|---|---|---|---|---|
| | II: 14-16 weeks | Case | 7 | 2972 | 1439 | 3006 | 1305 | 4102 |
| | | Control | 82 | 1912 | 1022 | 1661 | 1249 | 2355 |
| | III: 17-19 weeks | Case | 4 | 4955 | 2961 | 5664 | 2799 | 7111 |
| | | Control | 72 | 2276 | 2707 | 1737 | 1295 | 2660 |
| | IV: 20-30 weeks | Case | 6 | 28526 | 56386 | 4209 | 1695 | 16377 |
| | | Control | 172 | 2092 | 1610 | 1727 | 1173 | 2456 |
| SVEGFR-2 (ng/ml) | I: <14 weeks | Case | 4 | 10.3 | 1.4 | 10.2 | 9.2 | 11.5 |
| | | Control | 110 | 10.1 | 2.0 | 9.9 | 8.8 | 11.1 |
| | II: 14-16 weeks | Case | 7 | 10.7 | 1.7 | 11.1 | 9.7 | 11.8 |
| | | Control | 82 | 10.3 | 1.8 | 10.2 | 9.0 | 11.2 |
| | III: 17-19 weeks | Case | 4 | 11.2 | 1.3 | 11.1 | 10.2 | 12.3 |
| | | Control | 72 | 10.6 | 1.9 | 10.3 | 9.3 | 12.0 |
| | IV: 20-30 weeks | Case | 6 | 9.9 | 2.5 | 10.5 | 7.6 | 11.9 |
| | | Control | 172 | 10.9 | 2.0 | 10.7 | 9.7 | 12.2 |
| PlGF/sEng (pg/ng) | I: <14 weeks | Case | 4 | 2.4 | 0.7 | 2.4 | 1.8 | 2.9 |
| | | Control | 110 | 5.9 | 13.7 | 3.7 | 2.6 | 5.2 |
| | II: 14-16 weeks | Case | 7 | 14.1 | 7.3 | 14.3 | 5.6 | 20.6 |
| | | Control | 82 | 16.6 | 9.0 | 14.2 | 9.7 | 22.2 |
| | III: 17-19 weeks | Case | 4 | 11.8 | 8.2 | 11.7 | 6.1 | 17.6 |
| | | Control | 72 | 34.1 | 17.4. | 33.6 | 21.3 | 49.2 |
| | IV: 20-30 weeks | Case | 6 | 14.1 | 15.2 | 9.8 | 1.2 | 23.7 |
| | | Control | 172 | 1024 | 67.8 | 98.1 | 55.3 | 125.4 |
| PlGF/sVEGFR-1 | I: <14 weeks | Case | 4 | 0.01 | 0.01 | 0.01 | 0.01 | 0.02 |
| | | Control | 110 | 0.02 | 0.03 | 0.02 | 0.01 | 0.03 |
| | II: 14-16 weeks | Case | 7 | 0.04 | 0.03 | 0.03 | 0.03 | 0.03 |
| | | Control | 82 | 0.07 | 0.04 | 0.06 | 0.03 | 0.09 |
| | III: 17-19 weeks | Case | 4 | 0.02 | 0.00 | 0.02 | 0.02 | 0.03 |
| | | Control | 72 | 0.13 | 0.11 | 0.10 | 0.07 | 0.15 |
| | IV: 20-30 weeks | Case | 6 | 0.04 | 0.05 | 0.03 | 0.00 | 0.05 |
| | | Control | 172 | 0.36 | 0.30 | 0.29 | 0.19 | 0.42 |

Note:
*N = number of subjects, not samples

Subjects who developed MPFD had 1) a significantly lower mean plasma concentration of PlGF than controls at 20-30 weeks of gestation; 2) a higher mean plasma concentration of sVEGFR-1 than the control group from 14-16 weeks of gestation; and 3) a higher mean sEng concentration, but a lower mean PlGF/VEGFR-1 ratio and PlGF/sEng ratio concentration, than those with uncomplicated pregnancies starting from 17-19 weeks onwards.

Angiogenic Profile of MPFD Compared to Other Pregnancy Complications. In MPFD, maternal plasma concentrations of sVEGFR-1 were higher across GA intervals (marginal difference as a function of time, p=0.09) while that of PlGF was significantly lower than uncomplicated pregnancies after 20 weeks of gestation. The early elevation of sVEGFR-1 in the second trimester especially from 14-16 weeks of gestation without a change in PlGF has never been observed in other pregnancy complications, and appears to be characteristic of MPFD thus far.

An elevation of plasma concentration of sVEGFR-1 is not specific to PE since none of the subjects with MPFD developed new-onset hypertension and proteinuria. Although an imbalance of angiogenic/anti-angiogenic factors has been observed in several obstetrical syndromes, the clinical presentation of the disorders may differ depending on the GA at which this perturbation occurs. For example, subjects destined to develop preterm and term PE have higher plasma concentrations of sVEGFR-1 starting from 26 and 30 weeks of gestation, respectively, and lower plasma concentrations of PlGF starting from 10-11 weeks of gestation compared with those in uncomplicated pregnancies. Different profiles of angiogenic/anti-angiogenic factors have also been reported in pregnancies with spontaneous preterm labor, small-for-gestational-age neonates and stillbirth. The change in plasma concentrations of angiogenic/anti-angiogenic factors in MPFD was observed prior to the diagnosis of an abnormal pregnancy outcome, and thus, provides an opportunity for the diagnosis and enrollment of these subjects for interventional trials especially in subjects with a history of MPFD. Sonography may also assist in the prenatal diagnosis of MPFD.

Prevention of Recurrence of MPFD. In many cases included in the current study, subjects had prior poor pregnancy outcomes, although placental pathology was not available for review. The strong association between MPFD and serious adverse pregnancy outcomes such as FD, fetal growth restriction, or recurrent miscarriage strengthens the value of placental pathologic examination in such cases. If MPFD is diagnosed, subsequent pregnancies are also at risk for these complications. The novel identification of abnormal concentrations of angiogenic and anti-angiogenic factors in the current study indicates that an angiogenic and anti-angiogenic imbalance may be a mechanism of disease in MPFD. This has implications because recent observations suggest that there may be therapeutic interventions to reverse an angiogenic and anti-angiogenic imbalance during pregnancy including the administration of pravastatin, VEGF or extracorporeal removal of sVEGFR-1.

Exemplary Embodiments—Set 1

1. A method of assessing the presence or risk of obstetrical complications in a subject including:
   obtaining a sample derived from the subject;
   assaying the sample for the concentration of one or more markers selected from PlGF, sVEGFR-1, and sEng;

determining a MoM maternal plasma concentration ratio of PIGF/sVEGFR-1 and/or a MoM maternal plasma concentration ratio of PIGF/sEng in the sample;

comparing the MoM maternal plasma concentration ratio to a threshold of 0.4; and identifying the presence or risk of obstetrical complications in the subject based on a MoM maternal plasma concentration ratio<0.4.

2. A method of embodiment 1 wherein the obstetrical complications are associated with an angiogenic and anti-angiogenic imbalance.

3. A method of any one of embodiments 1 or 2 wherein the sample is obtained after a 25th week of pregnancy, after a 26th week of pregnancy, after a 27th week of pregnancy, after a 28th week of pregnancy, after a 29th week of pregnancy, after a 30th week of pregnancy, after a 33rd week of pregnancy, after a 34th week of pregnancy, after a 35th week of pregnancy, after a 36th week of pregnancy, after a 37th week of pregnancy, after a 38th week of pregnancy, after a 39th week of pregnancy, or after a 40th week of pregnancy.

4. A method of any one of embodiments 1, 2 or 3 wherein the sample is blood or serum.

5. A method of any one of embodiments 1, 2, 3, or 4 wherein the MoM maternal plasma concentration ratio of PIGF/sVEGFR-1 and/or a MoM maternal plasma concentration ratio of PIGF/sEng<0.3 indicates the presence or risk of one or more obstetrical complications selected from PE, severe PE, severe late PE, and SGA.

6. A method of any one of embodiments 1, 2, 3, 4, or 5 wherein the MoM maternal plasma concentration ratio of PIGF/sVEGFR-1<0.12 indicates the presence or risk of obstetrical complications of FD or placental lesions suggestive of maternal vascular underperfusion.

7. A method of any one of embodiments 1, 2, 3, 4, or 5 wherein the MoM maternal plasma concentration ratio of PIGF/sEng<0.2 indicates the presence or risk of obstetrical complications of FD and/or placental lesion suggestive of maternal vascular underperfusion.

8. A method of any one of embodiments 1, 2, 3, 4, 5, 6, or 7 wherein the sample is obtained in a third trimester of pregnancy.

9. A method of any one of embodiments 1, 2, 3, 4, 5, 6, or 7 wherein the sample is obtained between a 30th week of pregnancy and a 34th week of pregnancy.

10. A method of any one of embodiments 1, 2, 3, or 4 wherein the MoM maternal plasma concentration ratio of PIGF/sVEGFR-1<0.375 indicates the presence or risk of obstetrical complications of FD and/or placental lesion suggestive of maternal vascular underperfusion.

11. A method of any one of embodiments 1, 2, 3, or 4 wherein the MoM maternal plasma concentration ratio of PIGF/sEng<0.3989 indicates the presence or risk of obstetrical complications of FD and/or placental lesion suggestive of maternal vascular underperfusion.

12. A method of any one of embodiments 1, 2, 3, 4, 5, 6, 7, 8, 9, 10, or 11 wherein the sample is obtained in a second trimester.

13. A method of any one of embodiments 1, 2, 3, 4, 5, 6, 7, 8, 9, 10, 11, or 12 wherein the sample is obtained between a 24th week of pregnancy and a 28th week of pregnancy.

14. A method of any one of embodiments 6, 7, 8, 9, 10, 11, 12, or 13 wherein the FD is associated with placental abruption, is associated with fetal growth restriction, or is idiopathic.

15. A method of any one of embodiments 6, 7, 10, 11, 12, 13, or 14 wherein the FD is not associated with congenital abnormalities or infection.

16. A method of preventing or reducing the risk of obstetrical complications or treating an obstetrical complication associated with an angiogenic and anti-angiogenic imbalance in a subject including administering an effective amount a water-soluble statin to the subject thereby preventing or reducing the risk of obstetrical complications or treating an obstetrical complication in the subject.

17. A method of embodiment 16 wherein the water-soluble statin is pravastatin.

18. A method of any one of embodiments 16 or 17 further including administering heparin and aspirin to the subject.

19. A method of embodiment 16, 17, or 18 wherein the risk of obstetrical complications is assessed using maternal plasma concentrations of angiogenic factors and anti-angiogenic factors.

20. A method of any one of embodiments 16, 17, 18, or 19 wherein the risk of obstetrical complications is assessed between a 13th week of pregnancy and a 17th week of pregnancy.

21. A method of any one of embodiments 16, 17, 18, 19, or 20 wherein the risk of obstetrical complications is assessed using a method of any one of embodiments 1, 2, 3, 4, 5, 6, 7, 8, 9, 10, 11, 12, 13, 14, or 15.

Exemplary Embodiments—Set 2

1. A method of assessing the presence or risk of an angiogenic and anti-angiogenic imbalance in a subject including:
    obtaining a sample derived from a subject;
    assaying the sample for the concentration of one or more markers selected from PIGF, sVEGFR-1, and sEng;
    analyzing the concentrations by assessing a ratio of PIGF/sVEGFR-1 and/or PIGF/sEng in the sample;
    determining a MoM maternal plasma concentration ratio of PIGF/sVEGFR-1 and/or a MoM maternal plasma concentration ratio of PIGF/sEng;
    comparing the MoM maternal plasma concentration ratio to a threshold; and identifying a presence or risk of an angiogenic and anti-angiogenic imbalance based on the comparison of the MoM maternal plasma concentration ratio to the threshold, wherein a MoM concentration of <0.12 for PIGF/sVEGFR-1 is indicative of an angiogenic and anti-angiogenic imbalance and a MoM concentration of <0.3 for PIGF/sEng is indicative of an angiogenic and anti-angiogenic imbalance.

2. A method of embodiment 1 including assessing a ratio of PIGF/sVEGFR-1 and a ratio of PIGF/sEng in the sample.

3. A method of any one of embodiments 1 or 2 wherein the presence of an angiogenic and anti-angiogenic imbalance is predictive of obstetrical complications.

4. A method of any one of embodiments 1, 2, or 3 wherein the obstetrical complications include one or more of PE, a SGA neonate, FD, preterm labor, early-onset fetal growth restriction, placental massive perivillous fibrin deposition or maternal floor infarction, maternal vascular underperfusion, placental lesions, placental abruption, mirror syndrome, molar pregnancy, or twin-to-twin transfusion syndrome.
5. A method of any one of embodiments 1, 2, 3, or 4 wherein the sample is obtained in a 30th week of pregnancy and a 34th week of pregnancy.
6. A method of any one of embodiments 1, 2, 3, 4, or 5 wherein the PIGF/sVEGFR-1 MoM concentration of <0.12 is indicative of a risk for severe late PE and/or FD.
7. A method of any one of embodiments 1, 2, 3, 4, 5, or 6 wherein the PIGF/sEng MoM concentration of <0.3 is indicative of a risk for severe late PE or late PE.
8. A method of any one of embodiments 1, 2, 3, 4, 5, 6, or 7 wherein the PIGF/sVEGFR-1 MoM concentration of <0.12 is indicative of a risk for delivery of an SGA neonate.
9. A method of any one of embodiments 1, 2, 3, 4, 5, 6, 7, or 8 wherein the PIGF/sEng MoM concentration of <0.3 is indicative of a risk for delivery of an SGA neonate.
10. A method of any one of embodiments 1, 2, 3, 4, 6, 7, 8, or 9 wherein the sample is obtained between a 24th week of pregnancy and a 28th week of pregnancy.
11. A method of any one of embodiments 1, 2, 3, 4, 6, 7, 8, 9, or 10 wherein an anti-angiogenic PIGF/sVEGFR-1 ratio is indicative of a risk for stillbirth, PE, delivery of an SGA neonate, pre-term labor, or pre-term PROM.
12. A method of any one of embodiments 1, 2, 3, 4, 5, 6, 7, 8, 9, 10, or 11 wherein the sample is blood or serum.
13. A method of any one of embodiments 1, 2, 3, 4, 5, 6, 7, 8, 9, 11, or 12 wherein the sample is obtained during the third trimester of a pregnancy.
14. A method of treating an angiogenic and anti-angiogenic imbalance in a subject including administering an effective amount of a water-soluble statin to the subject thereby treating the angiogenic and anti-angiogenic imbalance.
15. A method of embodiment 14 wherein the treating of the anti-angiogenic and anti-angiogenic imbalance prevents an obstetrical complication.
16. A method of embodiment 15 wherein the obstetrical complication is FD.
17. A method of embodiment 16 wherein the FD is associated with MFI or placental lesions consistent with maternal vascular underperfusion.
18. A method of any one of embodiments 14, 15, 16, or 17 wherein the water-soluble statin is pravastatin.
19. A method of embodiment 18 wherein the effective amount of pravastatin is 20 mg/day.
20. A method of any one of embodiments 14, 15, 16, 17, 18, or 19 further including administering heparin and aspirin to the pregnant subject.

Exemplary Embodiments—Set 3

1. A kit for assessing the presence or risk of an angiogenic and anti-angiogenic imbalance in a subject including protein and/or nucleotide sequences that bind to PIGF, sVEGFR-1, and sEng in a sample derived from a subject and directs diagnosis of the presence or risk of an angiogenic and anti-angiogenic imbalance based on a concentration of the bound protein and/or nucleotide sequences.

2. A kit of embodiment 1 further including a detectable marker.
3. A kit of embodiment 2 wherein the detectable marker is a radioactive isotope, enzyme, dye, fluorescent dye, magnetic bead, or biotin.
4. A kit of any one of embodiments 1, 2, or 3 further including reagents to perform an wherein the kit comprises reagents to perform an ELISA, a RIA, a Western blot, an immunoprecipitation, an immunohistochemical staining, flow cytometry, FACS, an enzyme substrate color method, and/or an antigen-antibody agglutination.
5. A kit of any one of embodiments 1, 2, 3, or 4 further including instructions.
6. A kit of any one of embodiments 1, 2, 3, 4, or 5 further including instructions to calculate MoM maternal plasma concentration ratio and/or threshold values.

As will be understood by one of ordinary skill in the art, each embodiment disclosed herein can comprise, consist essentially of, or consist of its particular stated element, step, ingredient or component. Thus, the terms "include" or "including" should be interpreted to recite: "comprise, consist of, or consist essentially of." As used herein, the transition term "comprise" or "comprises" means includes, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients or components and to those that do not materially affect the embodiment. As used herein, a material effect would cause a statistically significant reduction in the specificity of the assessment of the presence or risk of an obstetrical complication and/or the efficacy of the treatment of an obstetrical complication.

Unless otherwise indicated, all numbers used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e. denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to publications, patents and/or patent applications (collectively "references") throughout this specification. Each of the cited references is individually incorporated herein by reference for their particular cited teachings.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

Definitions and explanations used in the present disclosure are meant and intended to be controlling in any future construction unless clearly and unambiguously modified in the examples or when application of the meaning renders any construction meaningless or essentially meaningless. In cases where the construction of the term would render it meaningless or essentially meaningless, the definition should be taken from Webster's Dictionary, 3rd Edition or a dictionary known to those of ordinary skill in the art, such as the Oxford Dictionary of Biochemistry and Molecular Biology (Ed. Anthony Smith, Oxford University Press, Oxford, 2004).

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A method of treating an imbalance of angiogenic factor(s) and anti-angiogenic factor(s) in a pregnant female human subject, comprising;
   identifying the subject as having or at risk of the imbalance of angiogenic factors and anti-angiogenic factors, wherein the angiogenic factors comprise placental growth factor (PlGF), and/or the anti-angiogenic factors comprise soluble vascular endothelial growth factor receptor-1 (sVEGFR-1) and/or soluble endoglin (sEng); and
   administering to the subject an effective amount of a water-soluble statin, thereby treating the imbalance of angiogenic factors and anti-angiogenic factors.

2. The method of claim 1, wherein treating of the imbalance of angiogenic factors and anti-angiogenic factors treats an obstetrical complication.

3. The method of claim 2, wherein the obstetrical complication comprises one or more of preeclampsia (PE), a small for gestational age (SGA) neonate, fetal death (FD), preterm labor, early-onset fetal growth restriction, anhydramnios, placental perivillous fibrin deposition, maternal floor infarction, maternal vascular underperfusion, placental lesions, placental abruption, mirror syndrome, molar pregnancy, or twin-to-twin transfusion syndrome.

4. The method of claim 3 wherein the obstetrical complication is FD.

5. The method of claim 4 wherein the FD is associated with maternal floor infarction or placental lesions consistent with maternal vascular underperfusion.

6. The method of claim 1, wherein the water-soluble statin is pravastatin.

7. The method of claim 6, wherein the effective amount of pravastatin is 20 mg/day.

8. The method of claim 6, further comprising administering heparin and aspirin to the subject.

9. The method of claim 1, wherein identifying the subject as having or at risk of the imbalance of angiogenic factors and anti-angiogenic factors comprises:
   obtaining a blood or serum sample derived from a subject;
   assaying the sample for the concentration of one or more markers selected from the group consisting of placental growth factor (PlGF), soluble vascular endothelial growth factor receptor-1 (sVEGFR-1), and soluble endoglin (sEng);
   analyzing the concentrations by assessing a ratio of PlGF/sVEGFR-1 and/or PlGF/sEng in the sample;
   determining a MoM maternal plasma concentration ratio of PlGF/sVEGFR-1 and/or a MoM maternal plasma concentration ratio of PlGF/sEng;
   comparing the determined MoM maternal plasma concentration ratio to a threshold;
   identifying a presence or risk of an imbalance of angiogenic factors and anti-angiogenic factors based on the comparison of the MoM maternal plasma concentration ratio to the threshold, wherein a MoM concentration of <0.12 for PlGF/sVEGFR-1 is indicative of an angiogenic and anti-angiogenic imbalance and a MoM concentration of <0.3 for PlGF/sEng is indicative of an angiogenic and anti-angiogenic imbalance.

10. The method of claim 9, comprising determining a ratio of PlGF/sVEGFR-1 and a ratio of PlGF/sEng.

11. The method of claim 9, wherein the sample is obtained:
   during the third trimester of pregnancy; or
   between a 30th week and a 34th week of pregnancy.

12. The method of claim 11 wherein:
   the MoM maternal plasma concentration ratio of PlGF/sVEGFR-1 of <0.12 is indicative of a risk for severe late PE and/or FD; or
   the MoM maternal plasma concentration ratio of PlGF/sEng of <0.3 is indicative of a risk for severe late PE or late PE; or
   the MoM maternal plasma concentration ratio of PlGF/sVEGFR-1 of <0.12 is indicative of a risk for delivery of an SGA neonate; or
   the MoM maternal plasma concentration ratio of PlGF/sEng of <0.3 is indicative of a risk for delivery of an SGA neonate.

13. The method of claim 9 wherein the sample is obtained between a 24th week of pregnancy and a 28th week of pregnancy.

14. The method of claim 13 wherein an anti-angiogenic PlGF/sVEGFR-1 ratio is indicative of a risk for stillbirth, PE, delivery of an SGA neonate, or pre-term labor.

* * * * *